United States Patent
Hansen, Jr. et al.

(10) Patent No.: US 6,951,889 B2
(45) Date of Patent: Oct. 4, 2005

(54) 2-AMINO-2-ALKYL-5 HEPTENOIC AND HEPTYNOIC ACID DERIVATIVES USEFUL AS NITRIC OXIDE SYNTHASE INHIBITORS

(75) Inventors: Donald W. Hansen, Jr., Skokie, IL (US); Ronald Keith Webber, St. Charles, MO (US); Barnett S. Pitzele, Skokie, IL (US); James Sikorski, Atlanta, GA (US); Mark A. Massa, Ballwin, MO (US); Timothy J. Hagen, Gurnee, IL (US); Margaret Grapperhaus, Troy, IL (US); Lijuan Jane Wang, Wildwood, MO (US); Arija A. Bergmanis, Des Plaines, IL (US); Steven W. Kramer, Des Plaines, IL (US); E. Ann Hallinan, Evanston, IL (US)

(73) Assignee: Pharmacia Corporation, St. Louis, MO (US)

( * ) Notice: Subject to any disclaimer, the term of this patent is extended or adjusted under 35 U.S.C. 154(b) by 127 days.

(21) Appl. No.: 09/953,049

(22) Filed: Sep. 15, 2001

(65) Prior Publication Data

US 2002/0132849 A1 Sep. 19, 2002

Related U.S. Application Data

(60) Provisional application No. 60/232,683, filed on Sep. 15, 2000.

(51) Int. Cl.[7] .................... A61K 31/195; C07C 251/00
(52) U.S. Cl. ...................... 514/564; 562/560
(58) Field of Search ............... 562/560, 574; 514/564

(56) References Cited

U.S. PATENT DOCUMENTS

| | | | |
|---|---|---|---|
| 5,132,453 A | 7/1992 | Griffith | 562/560 |
| 5,854,251 A | 12/1998 | Hallinan et al. | 514/256 |
| 5,945,408 A | 8/1999 | Webber et al. | 514/63 |
| 5,981,556 A | * 11/1999 | Hansen, Jr. et al. | |
| 5,994,391 A | 11/1999 | Lee et al. | 514/431 |

FOREIGN PATENT DOCUMENTS

| | | | |
|---|---|---|---|
| EP | 521471 | 6/1992 | ......... C07D/239/42 |
| WO | WO 9313055 | 7/1993 | ......... C07C/257/14 |
| WO | WO 9316055 | 8/1993 | ......... C07D/281/10 |
| WO | WO 9525717 | 9/1995 | ......... C07C/257/14 |
| WO | WO 9706802 | 2/1997 | ......... A61K/31/495 |
| WO | WO 0024719 | 5/2000 | ......... C07D/237/14 |

OTHER PUBLICATIONS

Misko, et al., *European Journal of Pharmacology*; 233: 119–125 (1993).
Moncada, S. & Higgs, E., *FASEB Journal*; 9: 1319–1330 (1995).
Lee, et al, *Bioorganic Med. Chemistry*; 7(6): 1097–1104 (1999).
Young et al., *Bioorganic Med. Chemistry Letters*; 10(6): 597–600 (2000).
Greene, Theodora & Wuts, Peter. *Protective Groups in Organic Synthesis, 3rd Edit.*; John Wiley & Sons, New York, (1999), pp. 494–653.
Jenmalm, A., et al., *Journal of Organic Chemistry*; 59: 1139–1148 (1994).
Harold, Mohr & Tan, *Helvetica Chimica Acta*; 66(2): 744–754 (1983).
Bredt & Snyder, *Proceedings of the National Academy of Science USA*; 87: 682–685 (1990).
Moore et al., *Journal of Medicinal Chemistry*; 39(3): 669–672 (1996).
Rodi et al., *The Biology of Nitric Oxide, Part 4: Enzymology, Biochemsitry, & Immunology*: Moncada, S; Freelisch, M; Busse, R; Higgs, E, Eds.; Portland Press Ltd., London (1995) pp 447–450.
Misko, et al., *Analytical Biochemistry*; 214(1): 11–16 (1993).
Chirchilla et al., *Synthesis*; 4: 704–717 (1999).

* cited by examiner

Primary Examiner—Paul A. Zucker
(74) Attorney, Agent, or Firm—Philip B. Polster, II

(57) ABSTRACT

The present invention relates to 2-amino-2-alkyl-5 heptenoic and heptynoic acid derivatives and their use in therapy, in particular their use as nitric oxide synthase inhibitors.

217 Claims, No Drawings

2-AMINO-2-ALKYL-5 HEPTENOIC AND HEPTYNOIC ACID DERIVATIVES USEFUL AS NITRIC OXIDE SYNTHASE INHIBITORS

CROSS REFERENCE TO RELATED APPLICATIONS

This application claims the benefit of U.S. Provisional Application Ser. No. 60/232,683, filed Sep. 15, 2000.

FIELD OF THE INVENTION

The present invention relates to 2-amino-2-alkyl-5 heptenoic and heptynoic acid derivatives and their use in therapy, in particular their use as nitric oxide synthase inhibitors.

RELATED ART

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed, this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase, such consequences including hypertension and possible thrombosis and tissue damage. In particular, in the case of the therapeutic use of L-NMMA (a non-selective NO synthase inhibitor) for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

PCT International Publication No. WO 93/13055 and U.S. Pat. No. 5,132,453, the disclosure of which are hereby incorporated by reference in their entirety as if written herein, disclose compounds that inhibit nitric oxide synthesis and preferentially inhibit the inducible isoform of nitric oxide synthase.

PCT International Publication No. WO 95/25717 discloses certain amidino derivatives as being useful in inhibiting inducible nitric oxide synthase.

Various attempts have been made to improve the potency and selectivity of NOS inhibitors by adding one or more rigidifying elements to the inhibitor's structure. Publications by Y. Lee et al (*Bioorg. Med. Chem.* 7, 1097 (1999)) and R. J. Young et al (*Bioorg. Med. Chem. Lett.* 10, 597 (2000)) teach that imposing conformational rigidity with one or more carbon-carbon double bonds is not a favorable approach to impart selectivity for NOS inhibitors.

SUMMARY OF THE INVENTION

Compounds have now been found which have the advantage of being very efficacious in the human cartilage explant assay, a model for osteoarthritis.

The present invention demonstrates that a carbon-carbon double bond can be used as a rigidifying element, and the resulting compounds have unexpected potency and selectivity for inhibition of inducible NOS.

Moreover, the publication by Y. Lee et al (*Bioorg. Med. Chem.* 7, 1097 (1999)) teaches that when a carbon-carbon double bond is used to constrain the arginine backbone, the geometric isomer placing the carbon framework in a cis or Z orientation produces a less favorable interaction with NOS. In contrast, olefinic derivatives of arginine placing the carbon framework in the trans or E configuration are better substrates. The present invention demonstrates that a carbon-carbon double bond imparts a favorable interaction with inducible NOS, such that the resulting compounds have unexpected potency and selectivity for inhibition of inducible NOS over the constitutive isoforms.

Further, compounds of the present invention have the advantage of being very efficacious as iNOS inhibitors in the human cartilage explant assay, a model for osteoarthritis. At the same time the compounds of the present invention are surprisingly less able to penetrate certain non-target organs in test systems, especially in comparison to the compounds of WO 93/13055. This surprising differentiation in expected access between the target organ (cartilage) and other organs is an unexpected advantage for the compounds of the present invention.

In a broad aspect, compounds of the present invention are represented by:

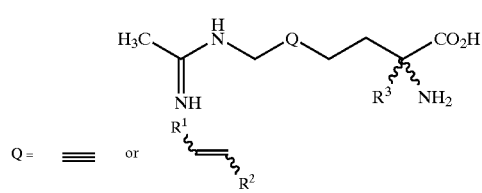

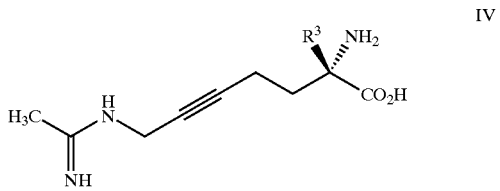

or a pharmaceutically acceptable salt thereof, wherein:
$R^1$ is, halo, $C_1$–$C_5$ alkyl or $C_1$–$C_5$ alkyl substituted by alkoxy or one or more halo;
$R^2$ is hydrogen, halo, $C_1$–$C_5$ alkyl or $C_1$–$C_5$ alkyl substituted by alkoxy or one or more halo; and $R^3$ is $C_1$–$C_5$ alkyl or $C_1$–$C_5$ alkyl be substituted by alkoxy or one or more halo.

In an embodiment represented by Formula I, the invention is represented to a compound of formula I:

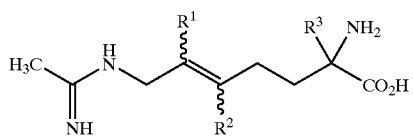

or a pharmaceutically acceptable salt thereof, wherein:
$R^1$ is hydrogen, halo, or $C_1$–$C_5$ alkyl, said $C_1$–$C_5$ alkyl optionally substituted by halo or alkoxy, said alkoxy optionally substituted by one or more halo;
$R^2$ is hydrogen, halo, or $C_1$–$C_5$ alkyl, said $C_5$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy, said alkoxy optionally substituted by one or more halo In an embodiment represented by Formula II, the invention relates to:

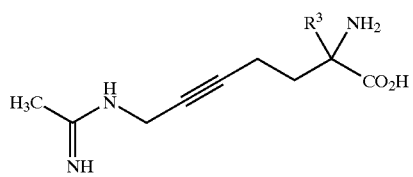

or a pharmaceutically acceptable salt thereof, wherein:
$R^3$ is $C_1$–$C_5$ alkyl, said $C_1$–$C_5$ alkyl optionally substituted by halo or alkoxy, said alkoxy optionally substituted by one or more halo.

In an embodiment represented by Formula III, the invention relates to:

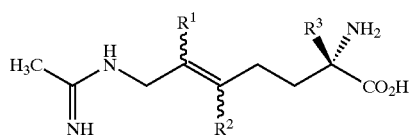

or a pharmaceutically acceptable salt thereof, wherein:
$R^1$ is hydrogen, halo, or $C_1$–$C_5$ alkyl, said $C_1$–$C_5$ alkyl optionally substituted by halo or alkoxy, said alkoxy optionally substituted by one or more halo;
$R^2$ is hydrogen, halo, or $C_1$–$C_5$ alkyl, said $C_1$–$C_5$ alkyl optionally substituted by halo or alkoxy, said alkoxy optionally substituted by one or more halo; and $R^3$ is $C_1$–$C_5$ alkyl, said $C_1$–$C_5$ alkyl optionally substituted by halo or alkoxy, said alkoxy optionally substituted by one or more halo.

In an embodiment represented by Formula IV, the invention relates to:

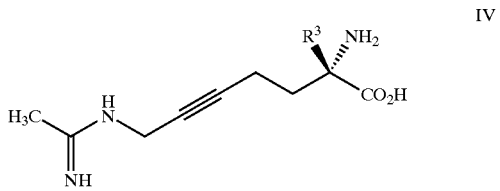

or a pharmaceutically acceptable salt thereof, wherein:
$R^3$ is $C_1$–$C_5$ alkyl, said $C_1$–$C_5$ alkyl optionally substituted by halo or alkoxy, said alkoxy optionally substituted by one or more halo.

In an embodiment represented by Formula V, the invention relates to:

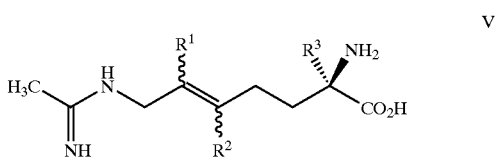

or a pharmaceutically acceptable salt thereof, wherein:
$R^1$ is hydrogen, halo, or $C_1$–$C_5$ alkyl, said $C_1$–$C_5$ alkyl optionally substituted by halo or alkoxy, said alkoxy optionally substituted by one or more halo;
$R^2$ is hydrogen, halo, or $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy, said alkoxy optionally substituted by one or more halo In an embodiment represented by Formula VI, the invention relates to:

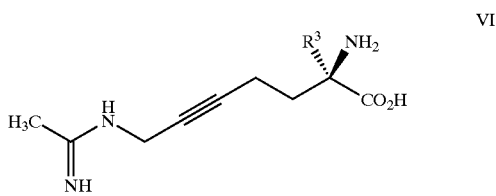

or a pharmaceutically acceptable salt thereof, wherein:
$R^3$ is $C_1$–$C_5$ alkyl, said $C_1$–$C_5$ alkyl optionally substituted by halo or alkoxy, said alkoxy optionally substituted by one or more halo.

In a broad aspect, the present invention is directed to novel compounds, pharmaceutical compositions, process for preparing novel compounds, process for preparing pharmaceutical compositions, and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part.

Compounds of the present invention will be useful for treating, among other things, inflammation in a subject, or for treating other nitric oxide synthase-mediated disorders, such as, as an analgesic in the treatment of pain and headaches. The compounds of the present invention will be useful in the treatment of pain including somatogenic (either nociceptive or neuropathic), both acute and chronic, and could be used in a situation including neuropathic pain for which a common NSAID, opioid analgesic or certain anticonvulsants would traditionally be administered.

Conditions in which the compounds of the present invention will provide an advantage in inhibiting NO production from L-arginine include arthritic conditions. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and post-operative inflammation including inflammation from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis.

Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. These compounds would also be useful in the treatment of allergic rhinitis, respiratory distress syndrome, endotoxin shock syndrome, and atherosclerosis. The compounds would also be useful in the treatment of pain, including but not limited to postoperative pain, dental pain, muscular pain, pain caused by temperoramandibular joint syndrome, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals and other vertebrates. More preferred animals include horses, dogs, and cats.

The present compounds may also be used in co-therapies, partially or completely, in place of other conventional anti-inflammatory therapies, such as together with steroids, NSAIDs, COX-2 selective inhibitors, matrix metalloproteinase inhibitors, 5-lipoxygenase inhibitors, $LTB_4$ antagonists and $LTA_4$ hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia, such as, for example pre-senile dementia, and AIDS-related dementia, cachexia, Sydenham's chorea, Huntington's disease, Amyotrophic Lateral Sclerosis, Korsakoff s disease, imbecility relating to a cerebral vessel disorder, sleeping disorders, schizophrenia, depression, depression or other symptoms associated with Premenstrual Syndrome (PMS), anxiety and septic shock.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

Compounds of the invention are useful for the prevention or treatment of cancer, such as colorectal cancer, and cancer of the breast, lung, prostate, bladder, cervix and skin. The present invention is further directed to the use of the compounds of the present invention for the treatment and prevention of neoplasias. The neoplasias that will be treatable or preventable by the compounds and methods of the present invention include brain cancer, bone cancer, a leukemia, such as, for example chronic lymphocytic leukemia, a lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, urogenital cancers, such as ovary cancer, cervical cancer, vulvar cancer, and lung cancer, breast cancer and skin cancer, such as squamous cell, melanoma, and basal cell cancers, prostate cancer, renal cell carcinoma, and other known cancers that effect epithelial cells throughout the body. Compounds of the present invention will be effective as well for treatment of mesenchymal derived neoplasias. Preferably, the neoplasia to be treated is selected from gastrointestinal cancer, liver cancer, bladder cancer, pancreas cancer, ovary cancer, prostate cancer, cervical cancer, vulvar cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHIP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1,; esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-81 10, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglurnide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation; latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid).

A further embodiment provides a therapeutic combination of a compound of the present invention with an opioid compound. Opioid compounds useful in this combination include without limitation morphine, methadone, hydromorphone, oxymorphone, levorphanol, levallorphan, codeine, dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, nor-binaltorphimine, naltrindole, DPDPE, [D-la$^2$, glu$^4$]deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

DETAILED DESCRIPTION OF THE INVENTION

In a broad aspect, compounds of the present invention are represented by:

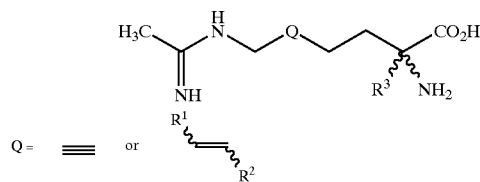

or a pharmaceutically acceptable salt thereof, wherein:
$R^1$ is hydrogen, halo, $C_1$–$C_5$ alkyl or $C_1$–$C_5$ alkyl substituted by alkoxy or one or more halo;
$R^2$ is hydrogen, halo, $C_1$–$C_5$ alkyl or $C_1$–$C_5$ alkyl substituted by alkoxy or one or more halo; and $R^3$ is $C_1$–$C_5$ alkyl or $C_1$–$C_5$ alkyl substituted by alkoxy or one or more halo.

In an embodiment represented by Formula I, the invention is represented to a compound of formula I:

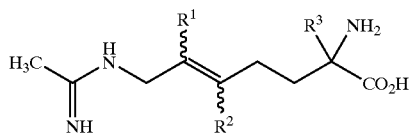

or a pharmaceutically acceptable salt thereof, wherein:
$R^1$ is hydrogen, halo, or $C_1$–$C_5$ alkyl, said $C_1$–$C_5$ alkyl optionally substituted by halo or alkoxy, said alkoxy optionally substituted by one or more halo;
$R^2$ is hydrogen, halo, or $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy, said alkoxy optionally substituted by one or more halo In one embodiment of the present invention represented by Formula I, the compound is the Z isomer.

In another embodiment of the present invention represented by Formula I, the compound is the E isomer.

In yet another embodiment of the present invention represented by Formula I, $R^1$ is hydrogen, halo, or $C_1$–$C_5$ alkyl, said $C_1$–$C_5$ alkyl optionally substituted by halo or alkoxy, said alkoxy optionally substituted by one or more halo; $R^2$ is hydrogen, halo or $C_1$–$C_5$ alkyl, said $C_1$–$C_5$ alkyl optionally substituted by halo or alkoxy, said alkoxy optionally substituted by one or more halo; and $R^3$ is $C_1$–$C_5$ alkyl, said $C_1$–$C_5$ alkyl optionally substituted by halo or alkoxy.

In another embodiment of the present invention represented by Formula I, $R^1$ is hydrogen, halo, or $C_1$–$C_3$ alkyl; $R^2$ is hydrogen, halo or $C_1$–$C_3$ alkyl; and $R^3$ is $C_1$–$C_5$ alkyl, said $C_1$–$C_5$ alkyl optionally substituted by fluorine or alkoxy.

In a further embodiment of the present invention represented by Formula I, $R^1$ is hydrogen, halo, or $C_1$–$C_3$ alkyl; $R^2$ is hydrogen, halo or $C_1$–$C_3$ alkyl; and $R^3$ is $C_1$–$C_3$ alkyl.

In another embodiment of the present invention represented by Formula I, $R^1$ is hydrogen; $R^2$ is hydrogen, halo or $C_1$–$C_3$ alkyl; and $R^3$ is $C_1$–$C_3$ alkyl.

In a still further embodiment of the present invention represented by Formula I, $R^1$ is hydrogen; $R^2$ is hydrogen or halo; and $R^3$ is $C_1$–$C_3$ alkyl.

In another embodiment of the present invention represented by Formula I, $R^1$ is hydrogen; $R^2$ is hydrogen or fluorine; and $R^3$ is $C_1$–$C_3$ alkyl.

In another embodiment of the present invention represented by Formula I, $R^1$ is hydrogen; $R^2$ is hydrogen or fluorine; and $R^3$ is methyl.

In another embodiment of the present invention represented by Formula I, $R^1$ is hydrogen; $R^2$ is hydrogen; and $R^3$ is methyl.

In a further embodiment of the present invention represented by Formula I, $R^1$ is hydrogen; $R^2$ is fluorine; and $R^3$ is methyl.

In another embodiment of the present invention represented by Formula I, $R^1$ is halo; $R^2$ is hydrogen, halo or $C_1$–$C_3$ alkyl; and $R^3$ is $C_1$–$C_3$ alkyl.

In a further embodiment of the present invention represented by Formula I, $R^1$ is halo; $R^2$ is halo; and $R^3$ is $C_1$–$C_3$ alkyl.

In another embodiment of the present invention represented by Formula I, $R^1$ is fluorine; $R^2$ is fluorine; and $R^3$ is methyl.

In another embodiment of the present invention represented by Formula I, $R^1$ is fluorine; $R^2$ is hydrogen or $C_1$–$C_3$ alkyl; and $R^3$ is methyl.

In a further embodiment of the present invention represented by Formula I, $R^1$ is fluorine; $R^2$ is hydrogen; and $R^3$ is methyl.

In another embodiment of the present invention represented by Formula I, $R^1$ is methyl; $R^2$ is hydrogen; and $R^3$ is methyl.

In a further embodiment of the present invention represented by Formula I, $R^1$ is hydrogen; $R^2$ is methyl; and $R^3$ is methyl.

In another embodiment of the present invention represented by Formula I, $R^1$ is methyl; $R^2$ is methyl; and $R^3$ is methyl.

In yet another embodiment of the present invention represented by Formula I, $R^1$ is hydrogen, halo or $C_1$–$C_5$ alkyl, said $C_1$–$C_5$ alkyl optionally substituted by alkoxy or one or more fluorine; $R^2$ is hydrogen, halo or $C_1$–$C_5$ alkyl, said $C_1$–$C_5$ alkyl optionally substituted by alkoxy or one or more fluorine; and $R^3$ is methyl optionally substituted by one or more alkoxy or halo.

In a further embodiment of the present invention represented by Formula I, $R^1$ is hydrogen or fluorine; $R^2$ is $C_1$–$C_3$ alkyl substituted by one or more halo; and $R^3$ is methyl.

In another embodiment of the present invention represented by Formula I, $R^1$ is hydrogen; $R^2$ is $CH_2F$; and $R^3$ is methyl.

In still another embodiment of the present invention represented by Formula I, $R^1$ is $CH_2F$; $R^2$ is hydrogen; and $R^3$ is methyl.

In a further embodiment of the present invention represented by Formula I, R¹ is hydrogen; R² is hydrogen; and R³ is CH₂F.

In another embodiment of the present invention represented by Formula I, R¹ is hydrogen; R² is methoxymethyl; and R³ is methyl.

In a further embodiment of the present invention represented by Formula I, R¹ is methoxymethyl; R² is hydrogen; and R³ is methyl.

In another embodiment of the present invention represented by Formula I, R¹ is hydrogen; R² is hydrogen; and R³ is methoxymethyl.

In an embodiment represented by Formula II, the invention relates to:

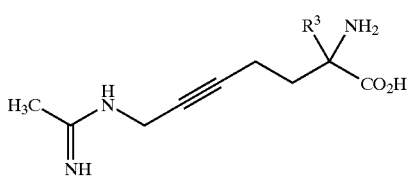

II or a pharmaceutically acceptable salt thereof, wherein:
R³ is $C_1$–$C_5$ alkyl, said $C_1$–$C_5$ alkyl optionally substituted by halo or alkoxy, said alkoxy optionally substituted by one or more halo.

In another embodiment of the present invention represented by Formula II, R³ is $C_1$–$C_5$ alkyl substituted by one or more halo.

In a further embodiment of the present invention represented by Formula II, R³ is $C_1$–$C_5$ alkyl substituted by one or more fluorine.

In still another embodiment of the present invention represented by Formula II, R³ is methyl substituted by one or more halo.

In yet another embodiment of the present invention represented by Formula II, R³ is methyl substituted by one or more fluorine.

In another embodiment of the present invention represented by Formula II, R³ is CH₂F.

In still another embodiment of the present invention represented by Formula II, R³ is $C_1$–$C_5$ alkyl substituted by alkoxy.

In a further embodiment of the present invention represented by Formula II, R³ is methoxy methyl.

In yet another embodiment of the present invention represented by Formula II, R³ is $C_1$–$C_5$ alkyl.

In another embodiment of the present invention represented by Formula II, R³ is methyl.

In an embodiment represented by Formula Im, the invention relates to:

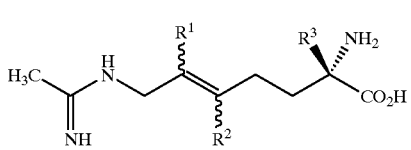

III or a pharmaceutically acceptable salt thereof, wherein:
R¹ is hydrogen, halo, or $C_1$–$C_5$ alkyl, said $C_1$–$C_5$ alkyl optionally substituted by halo or alkoxy, said alkoxy optionally substituted by one or more halo;
R² is hydrogen, halo, or $C_1$–$C_5$ alkyl, said $C_1$–$C_5$ alkyl optionally substituted by halo or alkoxy, said alkoxy optionally substituted by one or more halo; and R³ is $C_1$–$C_5$ alkyl, said $C_1$–$C_5$ alkyl optionally substituted by halo or alkoxy, said alkoxy optionally substituted by one or more halo.

In one embodiment of the present invention represented by Formula III, the compound is the Z isomer.

In another embodiment of the present invention represented by Formula III, the compound is the E isomer.

In yet another embodiment of the present invention represented by Formula III, R¹ is hydrogen, halo, or $C_1$–$C_5$ alkyl, said $C_1$–$C_5$ alkyl optionally substituted by halo or alkoxy, said alkoxy optionally substituted by one or more halo; R² is hydrogen, halo or $C_1$–$C_5$ alkyl, said $C_1$–$C_5$ alkyl optionally substituted by halo or alkoxy, said alkoxy optionally substituted by one or more halo; and R³ is $C_1$–$C_5$ alkyl, said $C_1$–$C_5$ alkyl optionally substituted by halo or alkoxy.

In another embodiment of the present invention represented by Formula III, R¹ is hydrogen, halo, or $C_1$–$C_3$ alkyl; R² is hydrogen, halo or $C_1$–$C_3$ alkyl; and R³ is $C_1$–$C_5$ alkyl, said $C_1$–$C_5$ alkyl optionally substituted by fluorine or alkoxy.

In a further embodiment of the present invention represented by Formula III, R¹ is hydrogen, halo, or $C_1$–$C_3$ alkyl; R² is hydrogen, halo or $C_1$–$C_3$ alkyl; and R³ is $C_1$–$C_3$ alkyl.

In another embodiment of the present invention represented by Formula III, R¹ is hydrogen; R² is hydrogen, halo or $C_1$–$C_3$ alkyl; and R³ is $C_1$–$C_3$ alkyl.

In a still further embodiment of the present invention represented by Formula III, R¹ is hydrogen; R² is hydrogen or halo; and R³ is $C_1$–$C_3$ alkyl.

In another embodiment of the present invention represented by Formula III, R¹ is hydrogen; R² is hydrogen or fluorine; and R³ is $C_1$–$C_3$ alkyl.

In another embodiment of the present invention represented by Formula III, R¹ is hydrogen; R² is hydrogen or fluorine; and R³ is methyl.

In another embodiment of the present invention represented by Formula III, R¹ is hydrogen; R² is hydrogen; and R³ is methyl.

In a further embodiment of the present invention represented by Formula III, R¹ is hydrogen; R² is fluorine; and R³ is methyl.

In another embodiment of the present invention represented by Formula III, R¹ is halo; R² is hydrogen, halo or $C_1$–$C_3$ alkyl; and R³ is $C_1$–$C_3$ alkyl.

In a further embodiment of the present invention represented by Formula III, R¹ is halo; R² is halo; and R³ is $C_1$–$C_3$ alkyl.

In another embodiment of the present invention represented by Formula III, R¹ is fluorine; R² is fluorine; and R³ is methyl.

In another embodiment of the present invention represented by Formula III, R¹ is fluorine; R² is hydrogen or $C_1$–$C_3$ alkyl; and R³ is methyl.

In a further embodiment of the present invention represented by Formula III, R¹ is fluorine; R² is hydrogen; and R³ is methyl.

In another embodiment of the present invention represented by Formula III, R¹ is methyl; R² is hydrogen; and R³ is methyl.

In a further embodiment of the present invention represented by Formula III, R¹ is hydrogen; R² is methyl; and R³ is methyl.

In another embodiment of the present invention represented by Formula III, R¹ is methyl; R² is methyl; and R³ is methyl.

In yet another embodiment of the present invention represented by Formula III, R¹ is hydrogen, halo or $C_1$–$C_5$ alkyl, said $C_1$–$C_5$ alkyl optionally substituted by alkoxy or one or more fluorine; $R^2$ is hydrogen, halo or $C_1$–$C_5$ alkyl, said $C_1$–$C_5$ alkyl optionally substituted by alkoxy or one or more fluorine; and $R^3$ is methyl optionally substituted by one or more alkoxy or halo.

In a further embodiment of the present invention represented by Formula III, $R^1$ is hydrogen or fluorine; $R^2$ is $C_1$–$C_3$ alkyl substituted by one or more halo; and $R^3$ is methyl.

In another embodiment of the present invention represented by Formula III, $R^1$ is hydrogen; $R^2$ is $CH_2F$; and $R^3$ is methyl.

In still another embodiment of the present invention represented by Formula III, $R^1$ $R^1$ is $CH_2F$; $R^2$ is hydrogen; and $R^3$ is methyl.

In a further embodiment of the present invention represented by Formula III, $R^1$ is hydrogen; $R^2$ is hydrogen; and $R^3$ is $CH_2F$.

In another embodiment of the present invention represented by Formula III, $R^1$ is hydrogen; $R^2$ is methoxymethyl; and $R^3$ is methyl.

In a further embodiment of the present invention represented by Formula III, $R^1$ is methoxymethyl; $R^2$ is hydrogen; and $R^3$ is methyl.

In another embodiment of the present invention represented by Formula III, $R^1$ is hydrogen; $R^2$ is hydrogen; and $R^3$ is methoxymethyl.

In an embodiment represented by Formula IV, the invention relates to:

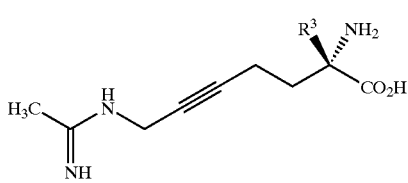

IV or a pharmaceutically acceptable salt thereof, wherein:
$R^3$ is $C_1$–$C_5$ alkyl or $C_1$–$C_5$ alkyl substituted by alkoxy or one or more halo.

In another embodiment of the present invention represented by Formula IV, $R^3$ is $C_1$–$C_5$ alkyl substituted by one or more halo.

In a further embodiment of the present invention represented by Formula IV, $R^3$ is $C_1$–$C_5$ alkyl substituted by one or more fluorine.

In still another embodiment of the present invention represented by Formula IV, $R^3$ is methyl substituted by one or more halo.

In yet another embodiment of the present invention represented by Formula IV, $R^3$ is methyl substituted by one or more fluorine. In another embodiment of the present invention represented by Formula IV, $R^3$ is $CH_2F$.

In still another embodiment of the present invention represented by Formula IV, $R^3$ is $C_1$–$C_5$ alkyl substituted by alkoxy.

In a further embodiment of the present invention represented by Formula IV, $R^3$ is methoxy methyl.

In yet another embodiment of the present invention represented by Formula IV, $R^3$ is $C_1$–$C_5$ alkyl.

In another embodiment of the present invention represented by Formula IV, $R^3$ is methyl.

In an embodiment represented by Formula V, the invention relates to:

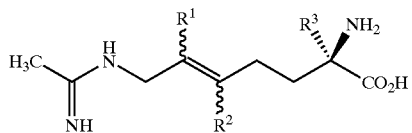

V or a pharmaceutically acceptable salt therof, wherein:
$R^1$ is hydrogen, halo, or $C_1$–$C_5$ alkyl, said $C_1$–$C_5$ alkyl optionally substituted by halo or alkoxy, said alkoxy optionally substituted by one or more halo;

$R^2$ is hydrogen, halo, or $C_1$–$C_5$ alkyl, said $C_1$–$C_5$ alkyl optionally substituted by halo or alkoxy, said alkoxy optionally substituted by one or more halo; and $R^3$ is $C_1$–$C_5$ alkyl, said $C_1$–$C_5$ alkyl optionally substiuted by halo or alkoxy, said alkoxy optionally substituted by one or more halo.

In one embodiment of the present invention represented by Formula V, the compound is the Z isomer.

In another embodiment of the present invention represented by Formula V, the compound is the E isomer.

In yet another embodiment of the present invention represented by Formula V, $R^1$ is hydrogen, halo, or $C_1$–$C_5$ alkyl, said $C_1$–$C_5$ alkyl optionally substituted by halo or alkoxy, said alkoxy optionally substituted by one or more halo; $R^2$ is hydrogen, halo or $C_1$–$C_5$ alkyl, said $C_1$–$C_5$ alkyl optionally substituted by halo or alkoxy, said alkoxy optionally substituted by one or more halo; and $R^3$ is $C_1$–$C_5$ alkyl, said $C_1$–$C_5$ alkyl optionally substituted by halo or alkoxy.

In another embodiment of the present invention represented by Formula V, $R^1$ is hydrogen, halo, or $C_1$–$C_3$ alkyl; $R^2$ is hydrogen, halo or $C_1$–$C_3$ alkyl; and $R^3$ is $C_1$–$C_5$ alkyl, said $C_1$–$C_5$ alkyl optionally substituted by fluorine or alkoxy.

In a further embodiment of the present invention represented by Formula V, $R^1$ is hydrogen, halo, or $C_1$–$C_3$ alkyl; $R^2$ is hydrogen, halo or $C_1$–$C_3$ alkyl; and $R^3$ is $C_1$–$C_3$ alkyl.

In another embodiment of the present invention represented by Formula V, $R^1$ is hydrogen; $R^2$ is hydrogen, halo or $C_1$–$C_3$ alkyl; and $R^3$ is $C_1$–$C_3$ alkyl.

In a still further embodiment of the present invention represented by Formula V, $R^1$ is hydrogen; $R^2$ is hydrogen or halo; and $R^3$ is $C_1$–$C_3$ alkyl.

In another embodiment of the present invention represented by Formula V, $R^1$ is hydrogen; $R^2$ is hydrogen or fluorine; and $R^3$ is $C_1$–$C_3$ alkyl.

In another embodiment of the present invention represented by Formula V, $R^1$ is hydrogen; $R^2$ is hydrogen or fluorine; and $R^3$ is methyl.

In another embodiment of the present invention represented by Formula V, $R^1$ is hydrogen; $R^2$ is hydrogen; and $R^3$ is methyl.

In a further embodiment of the present invention represented by Formula V, $R^1$ is hydrogen; R is fluorine; and $R^3$ is methyl.

In another embodiment of the present invention represented by Formula V, $R^1$ is halo; $R^2$ is hydrogen, halo or $C_1$–$C_3$ alkyl; and $R^3$ is $C_1$–$C_3$ alkyl.

In a further embodiment of the present invention represented by Formula V, $R^1$ is halo; $R^2$ is halo; and $R^3$ is $C_1$–$C_3$ alkyl.

In another embodiment of the present invention represented by Formula V, $R^1$ is fluorine; $R^2$ is fluorine; and $R^3$ is methyl.

In another embodiment of the present invention represented by Formula V, $R^1$ is fluorine; $R^2$ is hydrogen or $C_1$–$C_3$ alkyl; and $R^3$ is methyl.

In a further embodiment of the present invention represented by Formula V, $R^1$ is fluorine; $R^2$ is hydrogen; and $R^3$ is methyl.

In another embodiment of the present invention represented by Formula V, $R^1$ is methyl; $R^2$ is hydrogen; and $R^3$ is methyl.

In a further embodiment of the present invention represented by Formula V, $R^1$ is hydrogen; $R^2$ is methyl; and $R^3$ is methyl.

In another embodiment of the present invention represented by Formula V, $R^1$ is methyl; $R^2$ is methyl; and $R^3$ is methyl.

In yet another embodiment of the present invention represented by Formula V, $R^1$ is hydrogen, halo or $C_1$–$C_5$ alkyl, said $C_1$–$C_5$ alkyl optionally substituted by alkoxy or one or more fluorine; $R^2$ is hydrogen, halo or $C_1$–$C_5$ alkyl, said $C_1$–$C_5$ alkyl optionally substituted by alkoxy or one or more fluorine; and $R^3$ is methyl optionally substituted by one or more alkoxy or halo.

In a further embodiment of the present invention represented by Formula V, $R^1$ is hydrogen or fluorine; $R^2$ is $C_1$–$C_3$ alkyl substituted by one or more halo; and $R^3$ is methyl.

In another embodiment of the present invention represented by Formula V, $R^1$ is hydrogen; $R^2$ is $CH_2F$; and $R^3$ is methyl.

In still another embodiment of the present invention represented by Formula V, $R^1$ is $CH_2F$; $R^2$ is hydrogen; and $R^3$ is methyl.

In a further embodiment of the present invention represented by Formula V, $R^1$ is hydrogen; $R^2$ is hydrogen; and $R^3$ is $CH_2F$.

In another embodiment of the present invention represented by Formula V, $R^1$ is hydrogen; $R^2$ is methoxymethyl; and $R^3$ is methyl.

In a further embodiment of the present invention represented by Formula V, $R^1$ is methoxymethyl; $R^2$ is hydrogen; and $R^3$ is methyl.

In another embodiment of the present invention represented by Formula V, $R^1$ is hydrogen; $R^2$ is hydrogen; and $R^3$ is methoxymethyl.

In an embodiment represented by Formula VI, the invention relates to:

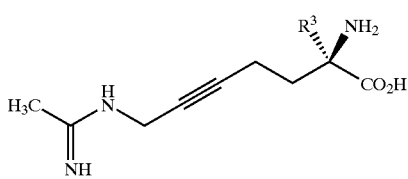

VI or a pharmaceutically acceptable salt thereof, wherein:
$R^3$ is $C_1$–$C_5$ alkyl or $C_1$–$C_5$ alkyl substituted by alkoxy or one or more halo.

In another embodiment of the present invention represented by Formula VI, $R^3$ is $C_1$–$C_5$ alkyl substituted by one or more halo.

In a further embodiment of the present invention represented by Formula VI, $R^3$ is $C_1$–$C_5$ alkyl substituted by one or more fluorine.

In still another embodiment of the present invention represented by Formula VI, $R^3$ is methyl substituted by one or more halo.

In yet another embodiment of the present invention represented by Formula VI, $R^3$ is methyl substituted by one or more fluorine. In another embodiment of the present invention represented by Formula VI, $R^3$ is $CH_2F$.

In still another embodiment of the present invention represented by Formula VI, $R^3$ is $C_1$–$C_5$ alkyl substituted by alkoxy.

In a further embodiment of the present invention represented by Formula VI, $R^3$ is methoxy methyl.

In yet another embodiment of the present invention represented by Formula VI, $R^3$ is $C_1$–$C_5$ alkyl.

In another embodiment of the present invention represented by Formula VI, $R^3$ is methyl.

Another embodiment of the present invention resides in a compound of Formula VII:

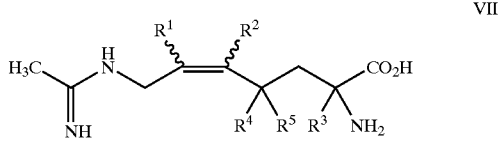

VII or a pharmaceutically acceptable salt thereof, wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
$R^5$ is selected from the group consisting of halo and $C_1$–$C_5$ alkyl, said $C_1$–$C_5$ alkyl optionally substituted by halo or alkoxy, said alkoxy optionally substituted by one or more halo.

In a further embodiment of the present invention represented by Formula VII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and
$R^5$ is selected from the group consisting of halo and $C_1$–$C_5$ alkyl, said $C_1$–$C_5$ alkyl optionally substituted by halo or alkoxy.

In yet another embodiment of the present invention represented by Formula VII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen and halo; and $R^5$ is selected from the group consisting of halo and $C_1$–$C_5$ alkyl, said $C_1$–$C_5$ alkyl optionally substituted by halo or alkoxy.

In another embodiment of the present invention represented by Formula VII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $C_1$–$C_5$ alkyl, said $C_1$–$C_5$ alkyl optionally substituted by halo or alkoxy, said alkoxy optionally substituted by one or more halo.

In a further embodiment of the present invention represented by Formula VII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $C_1$–$C_5$ alkyl, said $C_1$–$C_5$ alkyl optionally substituted by one or more halo In yet another embodiment of the present invention represented by Formula VII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is $C_1$–$C_5$ alkyl, said $C_1$–$C_5$ alkyl optionally substituted by halo or alkoxy, said alkoxy optionally substituted by one or more halo; and $R^5$ is halo.

In a further embodiment of the present invention represented by Formula VII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is $C_1$–$C_5$ alkyl, said $C_1$–$C_5$ alkyl optionally substituted by halo or alkoxy, said alkoxy optionally substituted by one or more halo; and $R^5$ is fluorine.

In another embodiment of the present invention represented by Formula VII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $C_1$–$C_5$ alkyl substituted by halo.

In a further embodiment of the present invention represented by Formula VII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $CH_2F$.

In another embodiment of the present invention represented by Formula VII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is hydrogen; and $R^5$ is $CH_2F$.

In another embodiment of the present invention represented by Formula VII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is halo; and
$R^5$ is halo.

In a further embodiment of the present invention represented by Formula VII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is fluorine; and
$R^5$ is halo.

In another embodiment of the present invention represented by Formula VII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is fluorine; and
$R^5$ is fluorine.

In another embodiment of the present invention represented by Formula VII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is hydrogen; and
$R^5$ is methyl.

Another embodiment of the present invention resides in a compound of Formula VIII:

or a pharmaceutically acceptable salt thereof, wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
$R^5$ is selected from the group consisting of halo and $C_1$–$C_5$ alkyl, said $C_1$–$C_5$ alkyl optionally substituted by halo or alkoxy, said alkoxy optionally substituted by one or more halo.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and
$R^5$ is selected from the group consisting of halo and $C_1$–$C_5$ alkyl, said $C_1$–$C_5$ alkyl optionally substituted by halo or alkoxy.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen and halo; and
$R^5$ is selected from the group consisting of halo and $C_1$–$C_5$ alkyl, said $C_1$–$C_5$ alkyl optionally substituted by halo or alkoxy.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and $R^5$ is $C_1$–$C_5$ alkyl, said $C_1$–$C_5$ alkyl optionally substituted by halo or alkoxy, said alkoxy optionally substituted by one or more halo.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and
$R^5$ is $C_1$–$C_5$ alkyl, said $C_1$–$C_5$ alkyl optionally substituted by one or more halo In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is $C_1$–$C_5$ alkyl, said $C_1$–$C_5$ alkyl optionally substituted by halo or alkoxy, said alkoxy optionally substituted by one or more halo; and
$R^5$ is halo.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is $C_1$–$C_5$ alkyl, said $C_1$–$C_5$ alkyl optionally substituted by halo or alkoxy, said alkoxy optionally substituted by one or more halo; and
$R^5$ is fluorine.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and
$R^5$ is $C_1$–$C_5$ alkyl substituted by halo.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and
$R^5$ is $CH_2F$.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is hydrogen; and
$R^1$ is $CH_2F$.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is halo; and
$R^5$ is halo.

In another embodiment of the present invention represented by Formula VII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is fluorine; and
$R^5$ is halo.

In another embodiment of the present invention represented by Formula VIII:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is fluorine; and
$R^5$ is fluorine.

In another embodiment of the present invention represented by Formula VIII:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is hydrogen; and
$R^5$ is methyl.

Another embodiment of the present invention resides in a compound of Formula IX:

or a pharmaceutically acceptable salt thereof, wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
$R^5$ is selected from the group consisting of halo and $C_1$–$C_5$ alkyl, said $C_1$–$C_5$ alkyl optionally substituted by halo or alkoxy, said alkoxy optionally substituted by one or more halo.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and
$R^5$ is selected from the group consisting of halo and $C_1$–$C_5$ alkyl, said $C_1$–$C_5$ alkyl optionally substituted by halo or alkoxy.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen and halo; and
$R^5$ is selected from the group consisting of halo and $C_1$–$C_5$ alkyl, said $C_1$–$C_5$ alkyl optionally substituted by halo or alkoxy.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and
$R^5$ is $C_1$–$C_5$ alkyl, said $C_1$–$C_5$ alkyl optionally substituted by halo or alkoxy, said alkoxy optionally substituted by one or more halo.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is selected from the group consisting of hydrogen, halo and $C_1$–$C_5$ alkyl, said $C_1$–$C_5$ alkyl optionally substituted by halo or alkoxy; and
$R^5$ is $C_1$–$C_5$ alkyl, said $C_1$–$C_5$ alkyl optionally substituted by one or more halo In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is $C_1$–$C_5$ alkyl, said $C_1$–$C_5$ alkyl optionally substituted by halo or alkoxy, said alkoxy optionally substituted by one or more halo; and
$R^5$ is halo.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is $C_1$–$C_5$ alkyl, said $C_1$–$C_5$ alkyl optionally substituted by halo or alkoxy, said alkoxy optionally substituted by one or more halo; and
$R^5$ is fluorine.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by alkoxy, said alkoxy optionally substituted by one or more halo;
$R^4$ is selected from the group consisting of hydrogen halo and $C_1$–$C_5$ alkyl, said $C_1$–$C_5$ alkyl optionally substituted by halo or alkoxy; and
$R^5$ is $C_1$–$C_5$ alkyl substituted by halo.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by alkoxy, said alkoxy optionally substituted by one or more halo;
$R^4$ is selected from the group consisting of hydrogen halo and $C_1$–$C_5$ alkyl, said $C_1$–$C_5$ alkyl optionally substituted by halo or alkoxy; and
$R^5$ is $CH_2F$.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is hydrogen; and
$R^5$ is $CH_2F$.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is halo; and
$R^5$ is halo.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is fluorine; and
$R^5$ is halo.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;
$R^4$ is fluorine; and
$R^5$ is fluorine.

In another embodiment of the present invention represented by Formula IX:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^3$ is $C_1$–$C_5$ alkyl, said $C_1$–$C_5$ alkyl optionally substituted by halo or alkoxy, said alkoxy optionally substituted by one or more halo;

R⁴ is hydrogen; and

R⁵ is methyl.

The present invention also includes pharmaceutical compositions that comprise a compound of Formula I, II, III, IV, V, VI, VII, VIII or IX.

Methods of using the compounds of Formula I, II, III, IV, V, VI, VII, VIII or IX include the use of inhibiting nitric oxide synthesis in a subject in need of such inhibition by administering a therapeutically effective amount of the present compound, selectively inhibiting nitric oxide synthesis produced by inducible nitric oxide synthase over nitric oxide produced by the constitutive forms of nitric oxide synthase in a subject in need of such inhibition by administering a therapeutically effective amount of a compound of Formula I, II, III, IV, V, or VI, lowering nitric oxide levels in a subject in need of such by administering a therapeutically effective amount of a compound of Formula I, II, III, IV, V, VI, VII, VIH or IX, lowering nitric oxide levels in a subject in need of such by administering a therapeutically effective amount of a pharmaceutical composition comprising a compound of Formula Formula I, II, III, IV, V, VI, VII, VIII or IX Compounds of the present invention will be useful for treating, among other things, inflammation in a subject, or for treating other nitric oxide synthase-mediated disorders, such as, as an analgesic in the treatment of pain and headaches, or as an antipyretic for the treatment of fever. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. Conditions in which the compounds of the present invention will provide an advantage in inhibiting NO production from L-arginine include arthritic conditions.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis. Compounds of the invention would be useful for the prevention or treatment of cancer, such as colorectal cancer, and cancer of the breast, lung, prostate, bladder, cervix and skin. Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, and atherosclerosis. The compounds would also be useful in the treatment of pain, but not limited to postoperative pain, dental pain, muscular pain, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

The compounds of the present invention will also be useful in the treatment of pain including somatogenic (either nociceptive or neuropathic), both acute and chronic. A nitric oxide inhibitor could be used in any situation including neuropathic pain that a common NSAID or opioid analgesic would traditionally be administered.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

The present invention is further directed to the use of the compounds of the present invention for the treatment and prevention of neoplasias. The neoplasias that will be treatable or preventable by the compounds and methods of the present invention include brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. Preferably, the neoplasia is selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATBF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, miitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isomeheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid).

A further embodiment provides a therapeutic combination of a compound of the present invention with an opioid compound. Opioid compounds useful in this combination include without limitation morphine, methadone, hydromorphone, oxymorphone, levorphanol, levallorphan, codeine,dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, nor-binaltorphimine, naltrindole, DPDPE, [D-la$^2$, glu$^4$]deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

Definitions

The term "alkyl", alone or in combination, means an acyclic aliphatic radical, linear or branched, preferably containing from 1 to about 10 carbon atoms and more preferably containing from 1 to about 6 carbon atoms. Alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical, linear or branched, in so much as it contains at least one double bond. Such radicals containing from 2 to about 6 carbon atoms, preferably from 2 to about 4 carbon atoms, more preferably from 2 to about 3 carbon atoms. Alkenyl radicals may be optionally substituted with groups as defined below. Examples of suitable alkenyl radicals include propenyl, 2-chloropropylenyl, buten-1-yl, isobutenyl, penten-1-yl, 2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical, linear or branched, in so much as it contains one or more triple bonds, such radicals containing 2 to about 6 carbon atoms, preferably from 2 to about 4 carbon atoms, more preferably from 2 to about 3 carbon atoms. Alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "oxo" means a doubly bonded oxygen.

The term "alkoxy" means a radical comprising an alkyl radical that is bonded to an oxygen atom, such as a methoxy radical. More preferred alkoxy radicals are "lower alkoxy" radicals having one to about ten carbon atoms. Still more preferred alkoxy radicals have one to about six carbon atoms. Non-limiting xamples of such radicals include methoxy, ethoxy, propoxy, isopropoxy, butoxy and tert-butoxy.

The phrase "optionally substituted" means that the indicated radical may, but need not be substituted for hydrogen. Thus, the phrase "optionally substituted by one or more" means that if a substitution is made at the indicated moiety, more than one substitution is contemplated as well. In this regard, if more than one optional substituent exists, either substituent may be selected, or a combination of substituents may be selected, or more than one of the same substituent may be selected. By way of example, and not limitation, the phrase "$C_1$–$C_5$ alkyl optionally substituted by one or more halo or alkoxy" should be taken to mean, for example, that methyl, ethyl, propyl, butyl, or pentyl may have at all substitutable positions: hydrogen, fluorine, chlorine or other halogen, methoxy, ethoxy, propoxy, iso butoxy, tert-butoxy, pentoxy or other alkoxy radicals, and combinations thereof. Non-limiting examples include: propyl, iso-propyl, methoxypropyl, fluoromethyl, fluoropropyl, 1-fluoro-methoxymethyl and the like.

Although nitrogen protecting groups are illustratively shown as, t-butoxycarbonyl, or t-BOC, any suitable nitrogen protecting group could be substituted in the synthesis of the compounds of the present invention. Numerous protected amino groups useful in the present invention for are described by Theodora W. Greene and Peter G. M. Wuts (*Protective Groups in Organic Synthesis,* 3rd ed., John Wiley & Sons, New York, 1999, pp. 494–653). For example NZ can be a 4-chlorobenzylimino group. In one embodiment of the present invention, the protected amino group is any such group resulting from the reaction of an aldehyde with the corresponding amino group to form a Schiff base. A large variety of deprotecting reagents can be advantageously used in the present invention to effect the conversion of the intermediate to the desired compound. Many such deprotecting reagents are described by Greene and Wuts, supra. For example, when the protected amino group is a 4-chlorobenzylimino group or a t-butoxycarbonylamino group, preferably the deprotecting reagent is an acid. Some useful acid deprotecting agents include, without limitation, hydrochloric acid, hydrobromic acid, sulfuric acid, trifluoroacetic acid, phosphoric acid, phosphorus acid, and acetic acid.

When a compound is described by both a structure and a name, the name is intended to correspond to the indicated structure, and similarly the structure is intended to correspond with the indicated name.

The term "Combination therapy" means the administration of two or more therapeutic agents to treat a therapeutic condition or disorder described in the present disclosure, for example atherosclerosis, pain, inflammation, migraine, neoplasia, angiogenisis-related conditions or disorder, or other indicated conditions. Such administration encompasses co-administration of two or more therapeutic agents in a substantially simultaneous manner, such as in a single capsule (or other delivery means) having a fixed ratio of active ingredients or in multiple, separate capsules (or other delivery means) for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" in the context of combination therapy is intended to qualify the combined amount of active ingredients in the combination therapy. This combined amount will achieve the goal of reducing or eliminating the indicated condition, or alleviating the symptoms of the indicated condition.

ILLUSTRATIVE EXAMPLES

The following synthesis schemes and examples are shown for illustrative purposes and in no way intended to limit the scope of the invention. Where isomers are not defined, utilization of appropriate chromatography methods will afford single isomers.

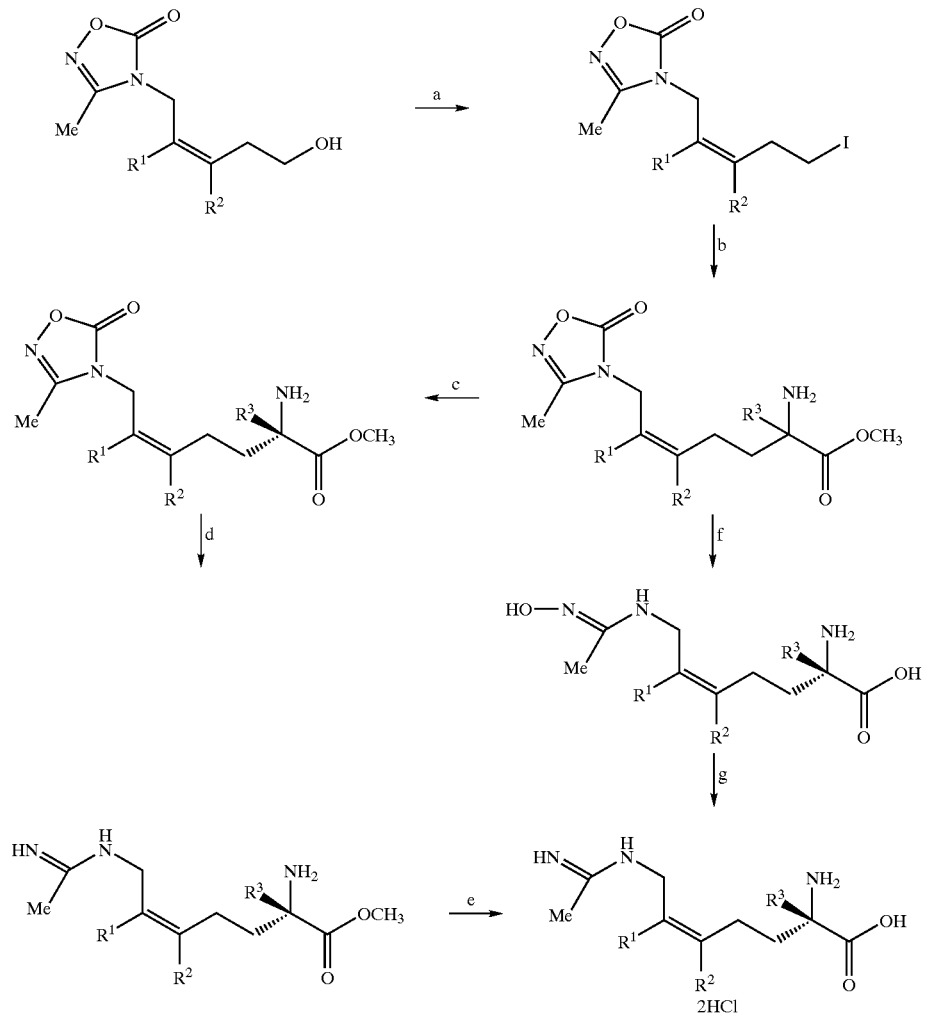

Generic Scheme 1 a) Methylene chloride, PPh$_3$, imidazole, I$_2$
b) 1. NMP, BTPP, an appropriate methyl N-[(3,4-dichlorophenyl)methylene]alaninate
   2. aqueous HCl
c) Chiral chromatography
d) Zn dust, acetic acid, water, heat
e) Aqueous HCl, heat
f) Aqueous NaOH
g) Lindlar catalyst with H$_2$ or Lindlar catalyst, MeOH or Pd black, MeOH or Zn, HOAc.

Scheme 2

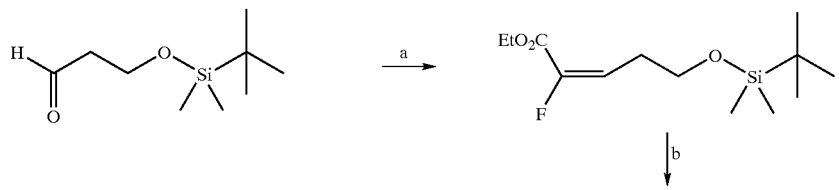

-continued

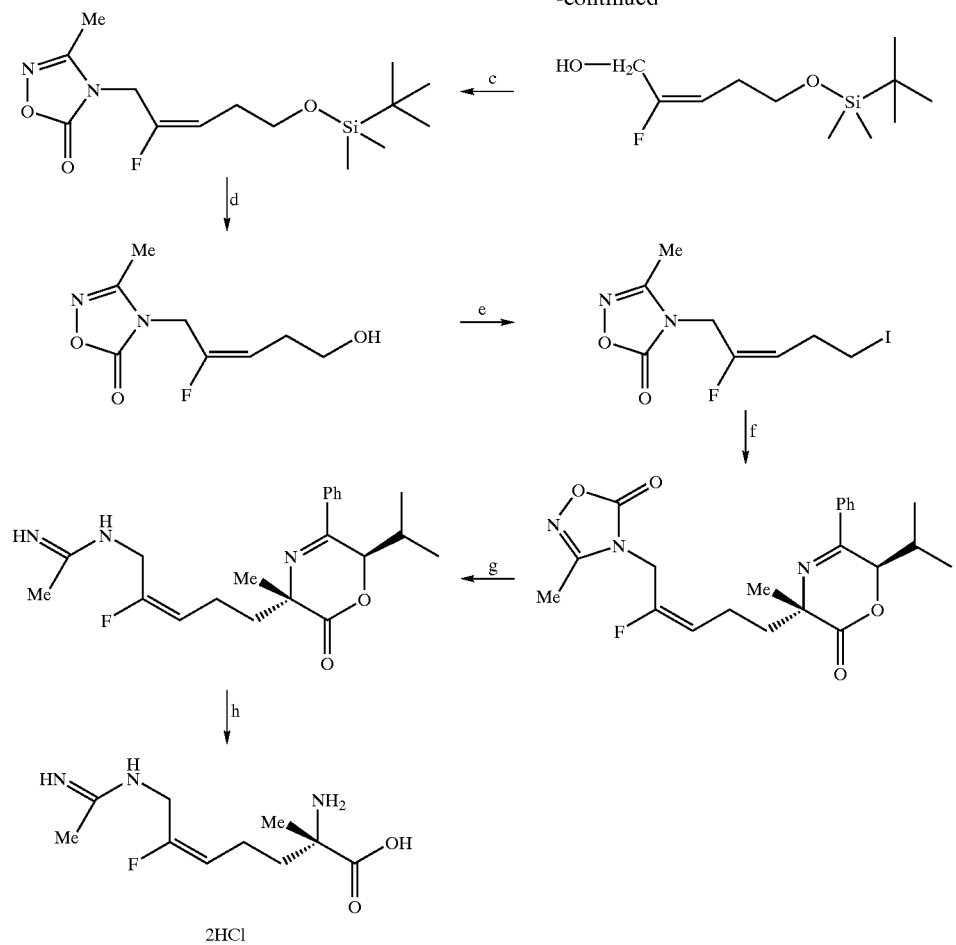

a) triethyl 2-fluorophosphonoacetate, n-butyl lithium, THF and hexane
b) NaBH₄, methanol, water
c) polymer-supported triphenylphosphine, 3-methyl-1,2,4-oxadiazolin-5-o ne, diethylazodicarboxylate, THF
d) acetic acid:THF:H₂O (3:1:1)
e) methylene chloride, PPh₃, imidazole, I₂
f) (3S, 6R)-6-Isopropyl-3-methyl-5-phenyl-3,6-dihydro-2H-1,4-oxazin-2 -one, BEMP, 1-methyl-2-pyrrolidinone
g) Lindlar catalyst, methanol, heat
h) aqueous HCl, heat

Example 1

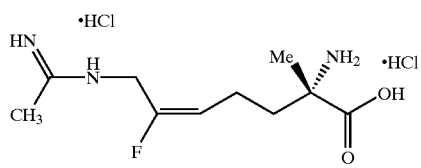

(2S,5E)-2-amino-2-methyl-6-fluoro-7-[(1-iminoethyl)amino]-5-heptenoic acid, Dihydrochloride

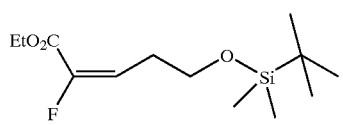

Example-1A

To a cold (−78° C.) solution of triethyl 2-fluorophosphonoacetate (25.4 g, 105 mmol) in 100 mL of THF was added n-butyl lithium (63 mL of 1.6 M in hexane, 101 mmol). This mixture was stirred at −78° C. for 20 mnin producing a bright yellow solution. A solution of crude 3-[(tert-butyldimethylsilyl)oxy]propanal (*J. Org. Chem.*, 1994, 59, 1139–1148) (20.0 g, 105 nunol) in 120 mL of THF was then added dropwise over ten minutes, and the resulting mixture was stirred for 1.5 h at −78° C., at which time analysis by thin layer chromatography (5% ethyl acetate in hexane) showed that no starting material remained. The reaction was quenched at −78° C. with sat. aqueous NHCl (150 mL). The organic layer was collected, and the aqueous layer was extracted with diethyl ether (300 mL). The combined organics were washed with brine (200 mL), dried over MgSO₄, filtered and concentrated. The crude material was filtered through a plug of silica gel (150 g) eluting with hexane (2 L) to give 14.38 g (52%) of the desired (2E)-5-[[(1,1-dimethylethyl)di-methylsilyl]oxy]-2-fluoro-2-pentenoic acid ethyl ester product as a clear oil. ¹H NMR and ¹⁹F NMR indicated that the isolated product had an approximate E:Z ratio of 95:5.

HRMS calcd. for $C_{13}H_{26}FO_3Si$: m/z=277.1635 [M+H]⁺, found: 277.1645. ¹H NMR (CDCl₃) δ 0.06 (s, 6H), 0.94 (s, 9H), 1.38 (t, 3H), 2.74 (m, 2H), 3.70 (m, 2H), 4.31 (q, 2H), 6.0 (dt, vinyl, 1H). $^{19}$F NMR (CDCl$_3$) δ −129.78 (d, 0.05 F, J=35 Hz, 5% Z-isomer), −121.65 (d, 0.95 F, J=23 Hz, 95% E-isomer).

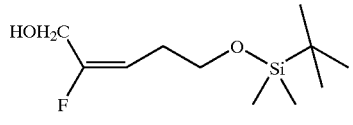

Example-1B

To a solution of Example-1A (6.76 g, 24.5 mmol) in 100 mL of methanol at room temperature was added solid NaBH$_4$ (4.2 g, 220 mmol) in 1.4 g portions over three hours. After 3.5 hours water was added (10 mL). Additional solid NaBH$_4$ (4.2 g, 220 mmol) was added in 1.4 g portions over three hours. The reaction was quenched with 150 mL of sat. aqueous NU$_4$Cl and extracted with diethyl ether (2×250 mL). The organic layers were combined, dried over MgSO$_4$, filtered and concentrated. The crude material, 4.81 g of clear oil, was purified by flash column chromatography on silica gel eluting with 10% ethyl acetate in hexane to give 2.39 g (42%) of the desired (2E)-5-[[(1,1-dimethylethyl)dimethylsilyl]oxy]-2-fluoro-2-penten-1-ol product as a clear oil, that contained an approximate E:Z ratio of 93:7 by $^{19}$F NMR.

HRMS calcd. for C$_{11}$H$_{24}$FO$_2$Si: m/z=235.1530 [M+H]$^+$, found: 235.1536. $^1$H NMR (CDCl$_3$) δ 0.06 (s, 6H), 0.88 (s, 9H), 2.35 (m, 2H), 3.62 (t, 2H), 4.19 (dd, 2H), 5.2 (dt, vinyl, 1H). $^{19}$F NMR (CDCl$_3$) δ −120.0 (dt, 0.07F, 7% Z-isomer), −109.82 (q, 0.93 F, J=21 Hz, 93% E-isomer).

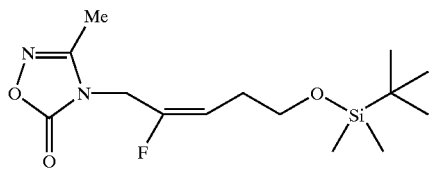

Example-1C

To a mixture of Example-1B (2.25 g, 9.58 mmol), polymer-supported triphenylphosphine (3 mmol/g, 1.86 g, 15 mmol) and 3-methyl-1,2,4-oxadiazolin-5-one (1.25 g, 12.5 mmol) in 60 mL of TBF was added dropwise diethylazodicarboxylate (2.35 mL, 14.7 mmol). The reaction mixture was stirred for 1 h at room temperature, and additional 3-methyl-1,2,4-oxadiazolin-5-one (0.30 g, 3.0 mmol) was added. After 30 minutes, the mixture was filtered through celite, and the filtrate was concentrated. The resulting yellow oil was triturated with diethyl ether (30 mL) and the solid removed by filtration. The filtrate was concentrated, triturated with hexane (30 mL) and filtered. The filtrates was concentrated to an oil which was purified by flash column chromatography on silica gel eluting with 15% ethyl acetate in hexane to give 1.83 g (60%) of the desired 4-[(2E)-5-[[(1,1-dimethylethyl)dimethylsilyl]oxy]-2-fluoro-2-pentenyl]-3-methyl-1,2,4-oxadi-azol-5(4H)-one product as a clear oil, that contained only the desired E-isomer by $^{19}$F NMR.

HRMS calcd. for C$_{14}$H$_{26}$FN$_2$O$_3$Si: m/z=317.1697 [M+H]$^+$, found: 317.1699. $^1$H NMR (CDCl$_3$) δ 0.04 (s, 6H), 0.85 (s, 9H), 2.28 (s, 3H), 2.37 (m, 2H), 3.64 (t, 2H), 4.32 (d, 2H), 5.4 (dt, vinyl, 1H). $^{19}$F NMR (CDCl$_3$) δ −110.20 (q, 1 F, J=21 Hz).

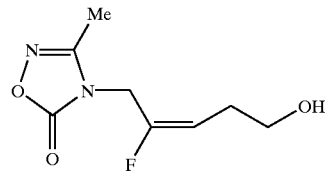

Example-1D

A solution of Example-1C (1.83 g, 5.78 mmol) in a mixture of acetic acid (6 mL), THF (2 mL) and water (2 mL) was stirred at room temperature for 2.5 hours. The resulting solution was concentrated in vacuo to an oil which was dissolved in diethyl ether (50 mL). The organic layer was washed with saturated NaHCO$_3$, and the aqueous layer was extracted with diethyl ether (2×50 mL) and ethyl acetate (2×50 mL). The combined organic layers were dried (MgSO$_4$), filtered and evaporated to give 1.15 g (98%) of the desired 4-[(2E)-2-fluoro-5-hydroxy-2-pentenyl]-3-methyl-1,2,4-oxadiazol-5(4H)-one product as a clear colorless oil.

HRMS calcd. for C$_8$H$_{12}$FN$_2$O$_3$: m/z=203.0832 [M+H]$^+$, found: 203.0822. $^1$H NMR (CDCl$_3$) δ 2.31 (3H), 2.4 (m, 2H), 3.66 (t, 2H), 4.37 (d, 2H), 5.42 (dt, vinyl, 1H). $^{19}$F NMR (CDCl$_3$) δ −110.20 (q, 1 F, J=21 Hz).

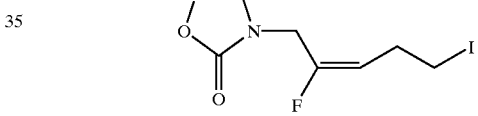

Example-1E

To a CH$_2$Cl$_2$ (2 mL) solution of t-riphenylphosphine (238 mig, 0.91 mmol) and imidazole (92 mg) at 0° C. was added solid iodine (230 mg, 0.91 mmol), and the mixture was stirred for 5 minutes. To the resulting yellow slurry was added a CH$_2$Cl$_2$ (1.5 mL) solution of Example-1D (0.15 g, 0.74 mmol). The slurry was allowed to warm to room temperature and stirred 30 minutes. The reaction mixture was diluted with CH$_2$Cl$_2$ (10 mL), washed with saturated Na$_2$S$_2$O$_3$ (5 mL) and brine (5 mL), dried (MgSO$_4$), filtered and evaporated to an oil. Addition of diethyl ether (10 mL) to the oil gave a white precipitate that was removed by filtration and the filtrate was concentrated to an oil. The crude material was purified by flash column chromatography on silica gel eluting with 30% ethyl acetate in hexane to give 0.18 g (78%) of the desired 4-[(2E)-2-fluoro-5-iodo-2-pentenyl]-3-methyl-1,2,4-oxadiazol-5(4H)-one product as a clear oil, which solidified upon standing, mp=58.1–58.6° C.

Anal. calcd. for C$_8$H$_{10}$FIN$_2$O$_2$: C, 30.79; H, 3.23; N, 8.98. Found: C, 30.83; H, 3.11; N, 8.85. HRMS calcd. for C$_8$H$_{11}$FIN$_2$O$_2$: m/z=330.0115 [M+H]$^+$, found: 330.0104. $^1$H NMR (CDCl$_3$) δ 2.31 (s, 3H), 2.75 (q, 2H), 3.21 (t, 2H), 4.31 (d, 2H), 5.39 (dt, vinyl, 1H). $^{19}$F NMR (CDCl$_3$) δ −108.21 (q, 1F, J=21 Hz).

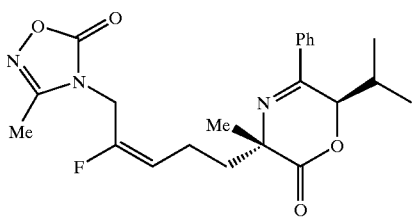

Example-1F

To a 1-methyl-2-pyrrolidinone (12 mL) solution of (3S, 6R)-6-isopropyl-3-methyl-5-phenyl-3,6-dihydro-2H-1,4-oxazin-2-one (*Synthesis,* 1999, 4, 704–717) (1.10 g, 4.76 mmol), LiI (0.63 g, 4.76 mmol) and Example-1E (0.85 g, 2.72 mmol) in an ice bath was added 2-tert-butylimino-2-diethylamino-1,3-dimethylperhydro-1,3,2-diazaphosphorine (1.38 mL, 4.76 mmol). The yellow solution became orange upon addition of the base, and the resulting solution was allowed to stir at room temperature for 1 hour. The reaction mixture was diluted with ethyl acetate (100 mL), washed with water (2×30 mL), dried (MgSO$_4$), filtered and evaporated to a yellow oil. The crude material was purified by flash column chromatography on silica gel eluting with 30% ethyl acetate in hexane to give 0.64 g (57%) of the desired alkylated product as a clear oil.

$^1$H NMR (C$_6$D$_6$) δ 0.57 (d, 3H), 0.89 (d, 3H), 1.30 (s, 3H), 1.65 (s, 3H), 1.8 (m, 2H), 2.0 (m, 2H), 2.1 (m, 1H), 3.22 (m, 2H), 4.88 (dt, vinyl, 1H), 5.49 (d, 1H), 7.1 (m, 3H), 7.6 (m, 2H). $^{19}$F NMR (CDCl$_3$) δ -110. 37 (q, 1 F, J=21 Hz).

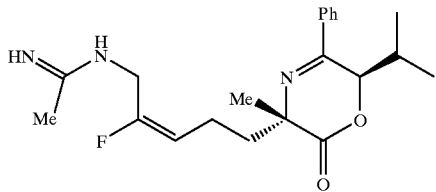

Example-1G

To a methanol (20 mL) solution of Example-1F (0.13 g, 0.31 mmol) was added Lindlar catalyst (1.0 g). The stirred slurry was heated to 60° C. for 1 hour, and additional Lindlar catalyst (0.30 g) was added. The slurry was stirred an additional 1 hour at 60° C., then cooled to room temperature. The catalyst was removed by filtration through celite, and the filtrate was stripped to give 0.58 g (100%) of the desired deprotected amidine product as a pale yellow oil.

MS: m/z=374.2 [M+H]$^+$ $^1$H NMR (CD$_3$OD) δ 0.77 (d, 3H), 1.07 (d, 3H), 1.58 (s, 3H), 2.02 (s, 3H), 1.8–2.2 (m, 5H), 3.83 (d, 2H), 5.20 (dt, vinyl, 1H), 5.69 (d, 1H), 7.4 (m, 3H), 7.7 m, 2H) $^{19}$F NMR (CDCl$_3$) δ -109.4 (m, 1F, J=21 Hz)

Example-1

A solution of the product from Example-1G (0.58 g, 1.54 mmol) in 1.5 N HCl (25 mL) was washed with diethyl ether (2×20 mL) and refluxed for 1 hour. The solvent was stripped and the crude amino acid ester was dissolved in 6 N HCl (15 mL) and heated to reflux. After six hours, the solvent was removed in vacuo, and the resulting foam was purified by reverse-phase HPLC eluting with a 30 minute gradient of 0–40% CH$_3$CN/H$_2$O(0.25% acetic acid). Fractions containing product were combined and concentrated to a foam. The product was dissolved in 1 N HCl and the solvent removed in vacuo (2×) to give 0.15 g (29%) of the desired (2S,5E)-2-amino-2-methyl-6-fluoro-7-[(1-iminoethyl)amino]-5-heptenoic acid, dihydrochloride product.

HRMS calcd. for C$_{10}$H$_{19}$FN$_3$O$_2$: m/z=232.1461 [M+H]$^+$, found: 232.1485. $^1$H NMR (D$_2$O) δ 1.43 (s, 3H), 2.10 (s, 3H), 1.8–2.1 (m, 4H), 3.98 (d, 2H) 5.29 (dt, vinyl, 1H). $^{19}$F NMR (CDCl$_3$) δ -109.97 (q, 1 F, J=21 Hz).

Scheme 3

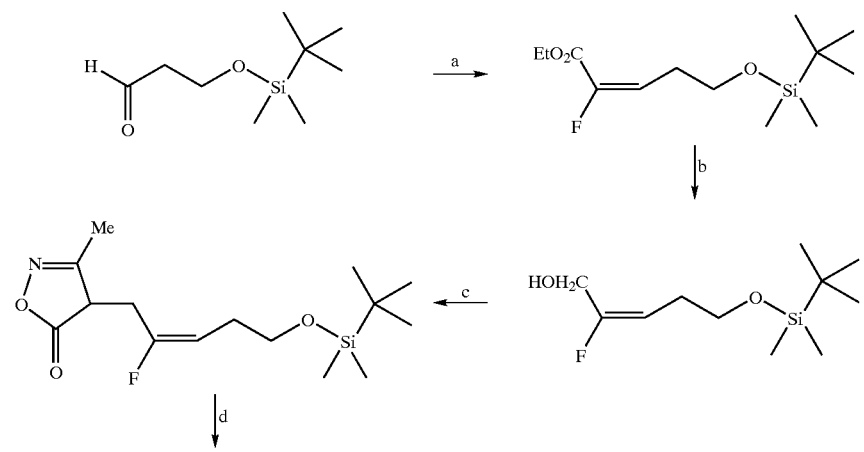

-continued

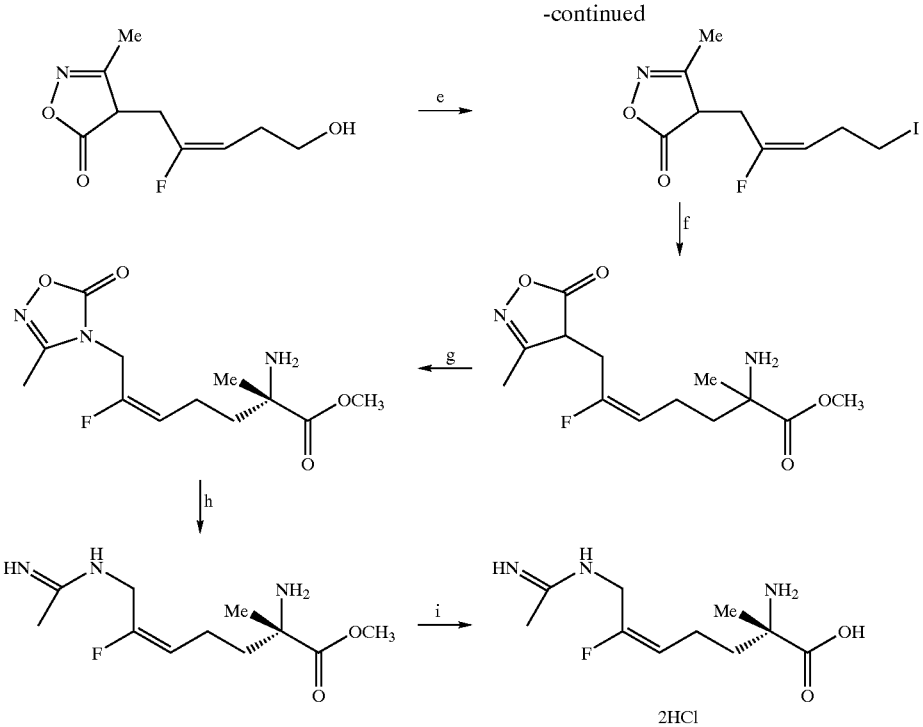

a) triethyl 2-fluorophosphonoacetate, DBU, LiCl, THF, -78° C.
b) RED—AL, THF, -5° C.
c) 1. MsCl, Et₃N, 5–10° C.
   2. Potassium salt of 3-methyl-1,2,4-oxadiazolin-5-one, DMSO, 50° C.
d) acetic acid:THF:H₂O (3:1:1)
e) methylene chloride, PPh₃, imidazole, I₂ or 1. MsCl, Et₃N 2. NaI
f) 1. NMP, BTPP, methyl N-[(3,4-dichlorophenyl)methylene]alaninate. 2 . aqueous HCl
g) Chiral chromatography (such as ChiralPak-AD, 100% acetonitrile)
h) Zn dust, acetic acid, water, heat or alternatively, Lindlar catalyst , formic acid, methanol
i) aqueous HCl, heat

Example 2

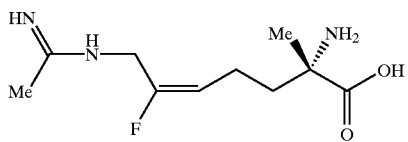

2HCl (2S,5E)-2-amino-2-methyl-6-fluoro-7-[(1-iminoethyl)amino]-5-heptenoic acid, Dihydrochloride

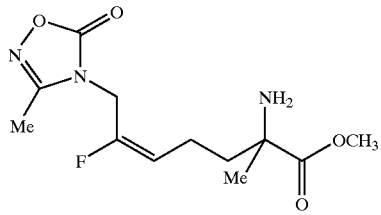

Example-2A

To a 1-methyl-2-pyrrolidinone (7500 mL) solution of methyl N-[(3,4-dichlorophenyl)-methylene]-alaninate (748.5 g, 2.88 mol) under nitrogen was added LiI (385.5 g, 2.88 mol) and the resulting slurry stirred approximately 20 minutes to give a clear solution. The solid from Example-1E (750 g, 2.40 mol) was then added and the resulting solution cooled in an ice bath to ~0° C. Neat BTPP (900 g, 2.88 mol) was added dropwise over 25 minutes maintaining the internal temperature below 5° C. After stirring for an additional 1.5 hour at 5° C., the reaction was determined to be complete by H:PLC. At this time, 7500 mL of methyl t-butyl ether (MTBE) was added followed by addition of 9750 mL of a water/crushed ice mixture. The temperature rose to 20° C. during this operation. After stirring vigorously for 5–10 minutes, the layers were separated and the aqueous layer washed with twice with 6000 mL of MTBE. The MTBE layers were combined and washed two times with 7500 mL of water. The resulting MTBE solution was then concentrated to ~5000 mL, treated with 11625 mL of 1.0 N HCl, and stirred vigorously at room temperature for one hour. The layers were separated and the aqueous layer washed with 7500 ml of MTBE. About 1 kg of sodium chloride was added to the aqueous layer and the resulting mixture stirred until all the salt had dissolved. At this point, 7500 mL of ethyl acetate was added, the resulting mixture cooled to 10° C., and 2025 mL of 6.0 N sodium hydroxide added with good agitation. The resulting pH should be about 9. The layers were separated and the aqueous layer was saturated with sodium chloride and extracted again with 7500 mL of ethyl acetate. The combined ethyl acetate extracts were dried (MgSO₄) and concentrated to a light oil. It should be noted that the ethyl acetate was not complete removed. With agitation, 3000 ml of hexane then is added to generate a slurry that was cooled to 10° C. The granular solid was collected by filtration and washed with 1500 mL of hexane. About 564 g (82% yield) of the desired pure aminoester (>95% pure by HPLC) was obtained as a white solid, m.p. 82.9–83.0° C. LCMS: m/z=288.2 [M+H]⁺. Chiral HPLC (Chiralpak-AD normal phase column, 100% acetonitrile, 210 nm, 1 mL/min): Two major peaks at 4.71 and 5.36 min (1:1).

¹H NMR (CDCl₃): δ 1.40 (s, 3H), 1.7–1.8 (m, 2H), 2.0 (br s, 2H), 2.2 (m, 2H), 2.29 (s, 3H), 3.73 (s, 3H), 4.34 (dd, 2H), 5.33 (dt, 1H).

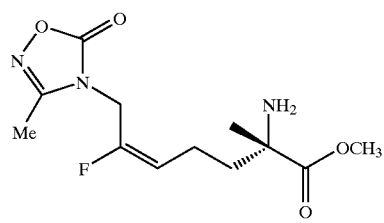

Example-2B

Separation of the individual enantiomers of the product from Example-2A was accomplished on preparative scale using chiral HPLC chromatography (ChiralPak-AD, normal phase column, 100% acetonitrile) to give the desired pure (2S)-2-methyl amino ester product title product. ChiralPak-AD, normal phase column, 100% acetonitrile, 210 nm, 1 mL/min): 5.14 min (99%).

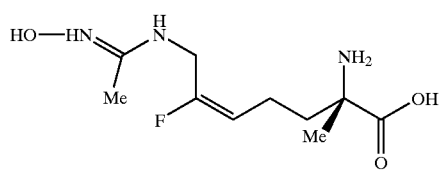

Example-2C

A slurry of the product of Example-2B (2.30 g, 8.01 mmol) in 0.993 M NaOH (30.0 ml, 29.79 mmol) was stirred 2 hours at room temperature. To the resulting clear colorless solution was added 1.023 M HCl (29.10 mL, 29.76 mmol). The resulting clear solution was concentrated until a precipitate began to form (approx. 30 mL). The slurry was warmed to give a clear solution that was allowed to stand at room temperature overnight. The precipitate was isolated by filtration. The solid was washed with cold water (2×10 mL), cold methanol (2×10 mL) and Et₂O (2×20 mL). The white solid was dried in vacuo at 40° C. 4 hours to give 1.04 g (53%) of the desired N-hydroxy illustrated product. mp=247.2° C.

Anal. calcd. for C₁₀H₁₈FN₃O₃: C, 48.57; H, 7.34; N, 16.99; Cl, 0.0. Found: C, 48.49; H, 7.37; N, 16.91; Cl, 0.0. HRMS calcd. for C₁₀H₁₉FN₃O₃: m/z=248.1410 [M+H]⁺, found: 248.1390. ¹H NMR (D₂O) δ 1.35 (s, 3H), 1.81 (s, 3H), 1.7–2.0 (m, 4H), 3.87 (d, 2H) 5.29 (dt, vinyl, 1H). ¹⁹F NMR (CDCl₃) δ –112.51 (q, 1 F, J=21 Hz).

Example-2

To a solution of Example-2C in methanol is added Lindlar catalyst. The stirred slurry is refluxed for 2 hours, then cooled to room temperature. The catalyst is removed by filtration through celite, and the filtrate is stripped. The resulting solid is dissolved in water and concentrated repeatedly from 1.0 N HCl to give the desired (2R,5E)-2-amino-2-methyl-6-fluoro-7-[(1-iminoethyl)amino]-5-heptenoic acid, dihydrochloride product.

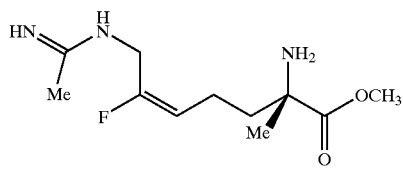

Example-2D

A solution of 73.5 g (0.3 mol) of the product from Example-2B was dissolved in 300 mL of methanol and added dropwise to a preformed mixture of 13.7 g of Lindlar catalyst and 73.5 g of formic acid (1.53 mol) in 312 mL of methanol while maintaining the reaction temperature between 22° C. and 26° C. After stirring at room temperature for an additional ~15 hrs, the reaction was determined to be complete by F¹⁹ NMR. The resulting reaction mixture was filtered through celite and the celite washed 3 times with 125 mL of methanol. The methanol filtrates were combined and concentrated to generate 115 g of the desired amidine title product as a viscous oil.

MS: m/z=246 (M+H)⁺. ¹H NMR (CD₃OD) δ1.6 (s, 3H) 2.0–2.2 (m, 4H) 2.3 (s, 3H), 3.9 (s, 3H), 4.2 (d, 2H), 5.4 (dt,vinyl), 8.4 (s, 3H). F¹⁹ NMR (CD₃OD) δ –110.4 (q, J=21 Hz) –111.7 (q, J=21 Hz).

In order to remove trace levels of lead, the crude product was dissolved in 750 mL of methanol and 150 g of a thiol-based resin (Deloxan THP 11) was added. After stirring 3 hrs at room temperature, the resin was filtered off and washed 2 times with 500 mL methanol. The filtrates were collected and concentrated to 99 g of the desired amidine title product as a viscous oil.

Alternatively:

A total of 5.0 g of the product from Example-2B (0.0174 mole, 1.0 equiv) was mixed with 5.0 g of zinc dust (0.0765 moles, 4.39 equiv) in 40 mL of 1-butanol and 10 mL of acetic acid. After stirring for 5 hrs at 50° C., LC analyses indicated the reaction to be complete. The solids were readily filtered off. The filtrate, after cooling in ice water to 7° C., was treated with 30 mL of 6 N NaOH (0.180 moles) in one portion with vigorous stirring. After cooling the reaction mixture from 33° C. to 20° C., the clear butanol layer was separated off and the aqueous layer extracted again with 40 mL of 1-butanol. The butanol extracts were combined, washed with 30 mL of brine followed by approx 10 mL of 6N HCl. After concentration at 70° C., a clear glass resulted which was identified as the desired amidine title product.

Example-2

A solution of 99 g of the product from Example-2D in 6 N HCl was refluxed for 1 hr at which time LC analyses indicated the reaction to be complete. The solvent was removed in vacuo to yield 89.2 g of a glassy oil which was dissolved in a mixture of 1466 mL ethanol and 7.5 ml of deionized water. THF was added to this agitated solution at ambient temperature until the cloud point was reached (5.5 liters). An additional 30 ml of deionized water was added and the solution agitated overnight at room temperature. The resulting slurry was filtered and washed with 200 mL of THF to yield 65 g of a white solid identified as the desired title product.

$[\alpha]_D^{25}$=+7.2 (c=0.9, H$_2$O) mp=126–130° C. MS: m/z= 232 (M+H)$^+$. Anal. Calcd for C$_{10}$H$_{22}$N$_3$F$_1$O$_3$Cl$_2$: C, 37.28; H, 6.88; N, 13.04; Cl, 22.01. Found: C, 37.52; H, 6.84; N, 13.21; Cl, 21.81. $^1$H NMR (D$_2$O) δ 1.4 (s, 3H), 1.8–2.1 (m, 4H), 1.9 (s,3H), 4.0(d, 2H), 5.3(dt, vinyl, 1H). F$^{19}$ NMR (D$_2$O) δ −109.6 (q, J=21 Hz) −112.1 (q, J-21 Hz).

Scheme 4

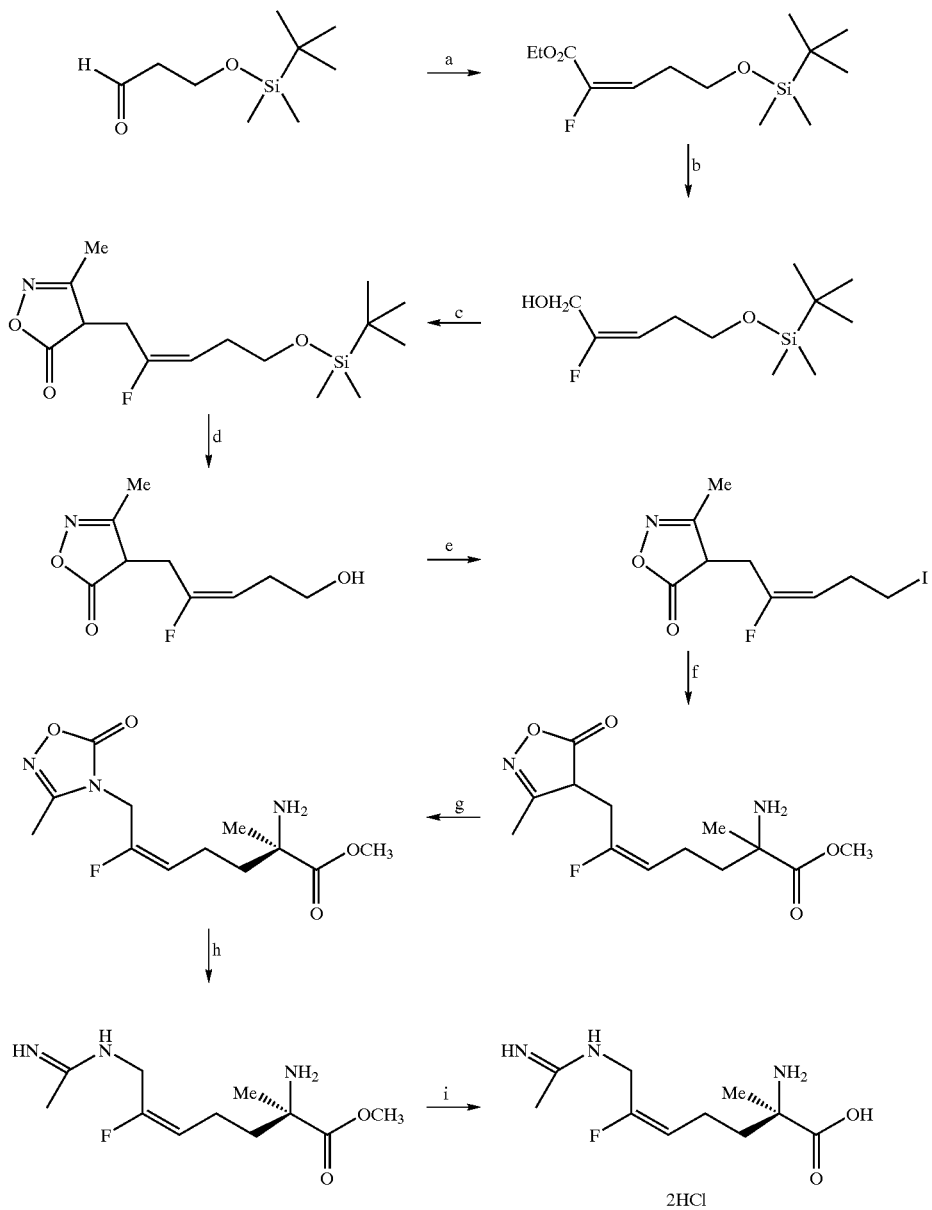

a) triethyl 2-fluorophosphonoacetate, DBU, LiCl, THF, -78° C.
b) RED——AL, THF, -5° C.
c) 1. MsCl, Et$_3$N, 5–10° C.
  2. Potassium salt of 3-methyl-1,2,4-oxadiazolin-5-one, DMSO, 50° C.
d) acetic acid:THF:H$_2$O (3:1:1)
e) methylene chloride, PPh$_3$, imidazole, I$_2$ or 1. MsCl, Et$_3$N 2. NaI
f) 1. NMP, BTPP, methyl N-[(3,4-dichlorophenyl)methylene]alaninate. 2. aqueous HCl
g) Chiral chromatography (such as ChiralPak-AD, 100% acetonitrile)
h) Zn dust, acetic acid, water, heat or alternatively, Lindlar catalyst, formic acid, methanol
i) aqueous HCl, heat

Example 3

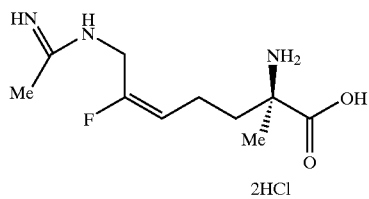

2HCl (2R,5E)-2-amino-2-methyl-6-fluoro-7-[(1-iminoethyl)amino]-5-heptenoic acid, Dihydrochloride

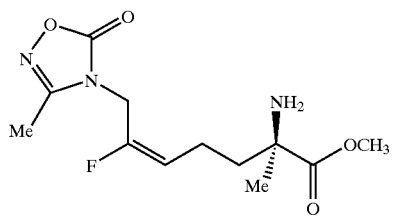

Example-3A

Separation of the individual enantiomers of the product from Example-2A was accomplished on preparative scale using chiral HPLC chromatography to give the desired pure (2R)-2-methyl amino ester product.

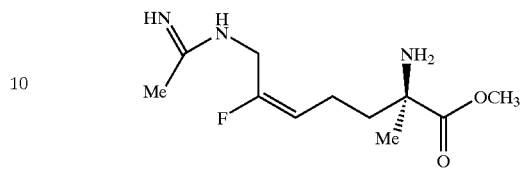

Example-3B

The product from Example-3A is dissolved in water and acetic acid. Zinc dust is added, and the mixture is heated at 60° C. until HPLC analysis shows that little of the starting material remains. The Zn is filtered through celite from the reaction mixture, and the filtrate is concentrated. The crude material is purified by reverse-phase HPLC column chromatography. Fractions containing product are combined and concentrated affording the desired (2R)-2-methyl acetamidine product.

Example-3

A solution of Example-3B in 2.0 N HCl is refluxed for 2 h. The solvent is removed in vacuo. The resulting solid is dissolved in water and concentrated repeatedly from 1.0 N HCl to give the desired (2R,5E)-2-amino-2-methyl-6-fluoro-7-[(1-iminoethyl)amino]-5-heptenoic acid, dihydrochloride product.

Scheme 5

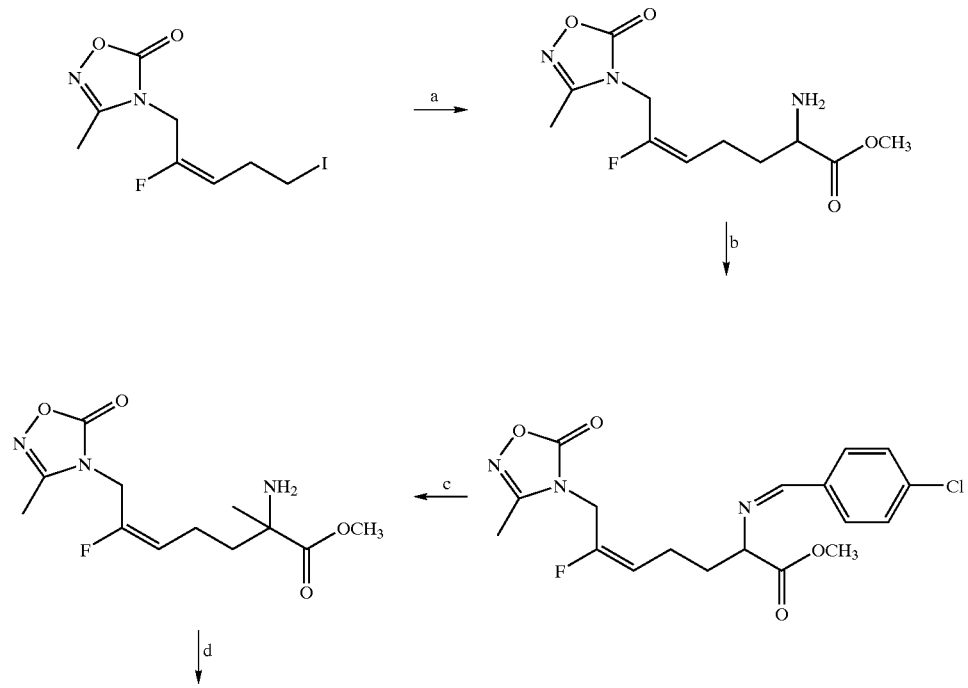

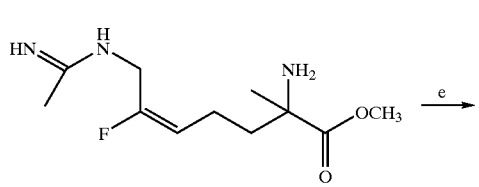
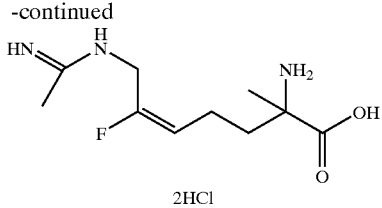

a) 1. NMP, BEMP, methyl N-[(4-chlorophenyl)methylene]glycinate 2. aqueous HCl
b) 4-chlorobenzaldehyde, CH₂Cl₂, MgSO₄
c) 1. NMP, BTPP, methyl iodide, O(9)-allyl-N-(9-anthracenylmethyl)- cinchonidinium bromide
   2. aqueous HCl
d) Zn dust, acetic acid, water, heat
e) aqueous HCl, heat

Example 4

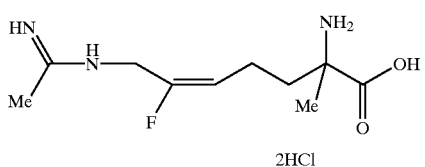

(2R/S,5E)-2-amino-2-methyl-6-fluoro-7-[(1-iminoethyl)amino]-5-heptenoic acid, Dihydrochloride

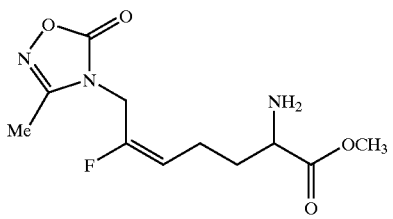

Example-4A

To an 1-methyl-2-pyrrolidinone (5 mL) solution of methyl N-[(4-chlorophenyl)methylene]-glycinate (0.33 g, 1.6 mmol), LiI (0.20 g, 1.0 mmol) and a sample of the product of Example-1E (0.30 g, 0.96 mmol) in an ice bath was added 2-tert-butylimino-2-diethylamino-1,3-dimethylperhydro-1,3,2-diazaphosphorine (0.433 mL, 1.5 mmol). The solution was allowed to stir at room temperature for 1.5 hours. The reaction mixture was diluted with ethyl acetate (30 mL), washed with water (2×20 mL), dried (MgSO₄), filtered, and evaporated to give the crude desired racemic alkylated imine as a yellow oil.

The crude material was dissolved in ethyl acetate (10 mL) and 1N HCl (10 mL) was added. The mixture was stirred for 2 hours at room temperature, and the organic layer was separated. The aqueous layer was neutralized with solid NaHCO₃ and extracted with ethyl acetate (2×30 mL). The organic layer was dried (MgSO₄), filtered and evaporated to give 0.13 g of the desired title racemic amino ester product as a yellow oil. This product was used in the next step without further purification. LCMS: m/z=288.2 [M+H]⁺.

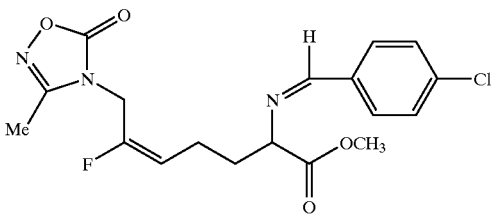

Example-4B

To a CH₂Cl₂ (15 mL) solution of Example-4A (1.36 g, 4.98 mmol) was added 4-chlorobenzaldehyde (0.70 g, 5.0 mmol) and MgSO₄ (~5 g). The slurry was stirred at room temperature for 18 hours. The slurry was filtered, and the filtrate stripped to give 1.98 g (100%) of the desired title imine product as a pale yellow oil. This product was used in the next step without further purification.

¹H NMR (C₆D₆) δ 1.34 (s, 3H), 2.0 (br m, 4H), 3.32 (s, 3H), 3.42 (m, 2H), 3.83 (t, 1H), 4.98 (dt, vinyl, 1H).

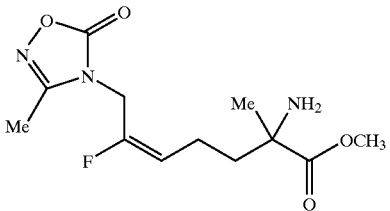

Example-4C

To a CH₂Cl₂ (2 mL) solution of the product of Example-4B (0.25 g, 0.63 mmol) was added methyl iodide (0.200 mL, 3.23 mmol) and O(9)-allyl-N-(9-anthracenylmethyl)-cinchonidinium bromide (40 mg, 0.066 mmol). The solution was cooled to −78° C. and neat BTPP (0.289 mL, 0.95 mmol) was added. The resulting orange solution was stirred at −78° C. for 2 hours and allowed to reach −50° C. After 2 hours at −50° C., the solution was diluted with CH₂Cl₂ (10 mL), washed with water (10 mL), dried (MgSO₄), filtered, and evaporated to give the crude desired racemic alkylated imine as a yellow oil.

The crude material was dissolved in ethyl acetate (10 mL) and 1N HCl (10 mL) was added. The mixture was stirred for 1 hour at room temperature, and the organic layer was separated. The aqueous layer was neutralized with solid NaHCO₃ and extracted with ethyl acetate (2×30 mL). The organic layer was dried (MgSO₄), filtered and evaporated to give 0.16 g of the desired racemic 2-methylamino ester product as a yellow oil. The product was used in the next step without further purification. LCMS: m/z=288.2 [M+H]$^+$.

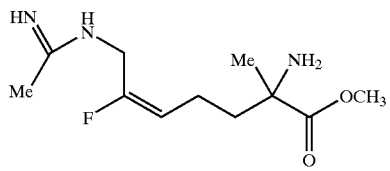

Example-4D

The racemic product from Example-4C is dissolved in water and acetic acid. Zinc dust is added, and the mixture is heated at 60° C. until HPLC analysis shows that little of the starting material remains. The Zn dust is filtered through celite from the reaction mixture, and the filtrate is concentrated. The crude material is purified by reverse-phase HPLC column chromatography. Fractions containing product are combined and concentrated affording the desired acetamidine product.

Example-4

A solution of racemic Example-4D in 2.0 N HCl is refluxed for 1 h. The solvent is removed in vacuo. The resulting solid is dissolved in water and concentrated repeatedly from 1.0 N HCl to give the desired title (2R/S,5E)-2-amino-2-methyl-6-fluoro-7-[(1-iminoethyl)amino]-5-heptenoic acid, dihydrochloride product.

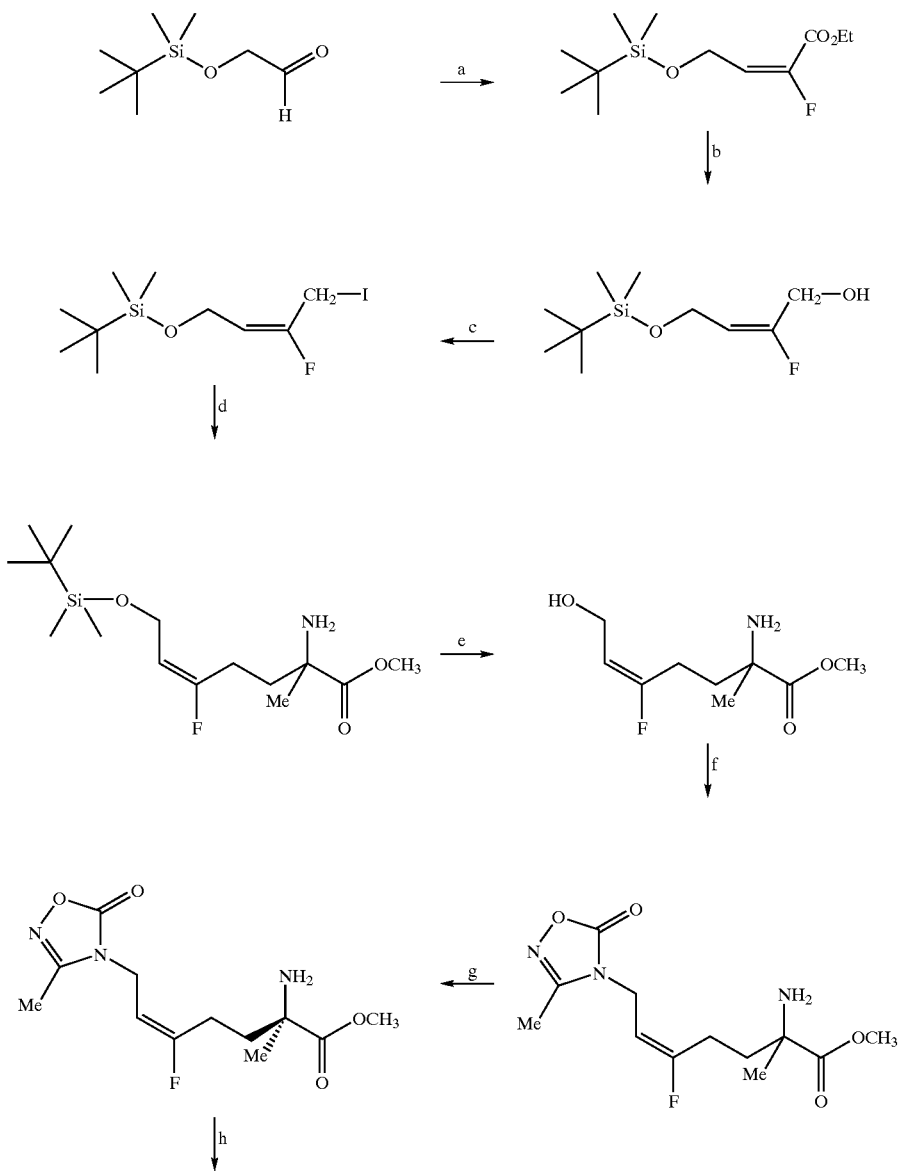

Scheme 6

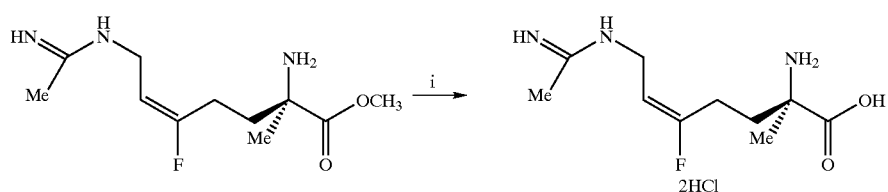

a) triethyl 2-fluorophosphonoacetate, n-butyl lithium, THF and hexane
b) DIBAL—H, THF
c) methylene chloride, PPh₃, imidazole, I₂
d) Zn/CuI/CuCN, THF; methyl (S)-2-iodomethyl-N-Boc-alaninate
e) acetic acid:THF:H₂O (3:1:1)
f) polymer-supported triphenylphosphine, 3-methyl-1,2,4-oxadiazolin-5-o ne, diethylazodicarboxylate, THF
g) chiral chromatography
h) Zn dust, acetic acid, methanol, water, heat
i) aqueous HCl, heat Scheme 7

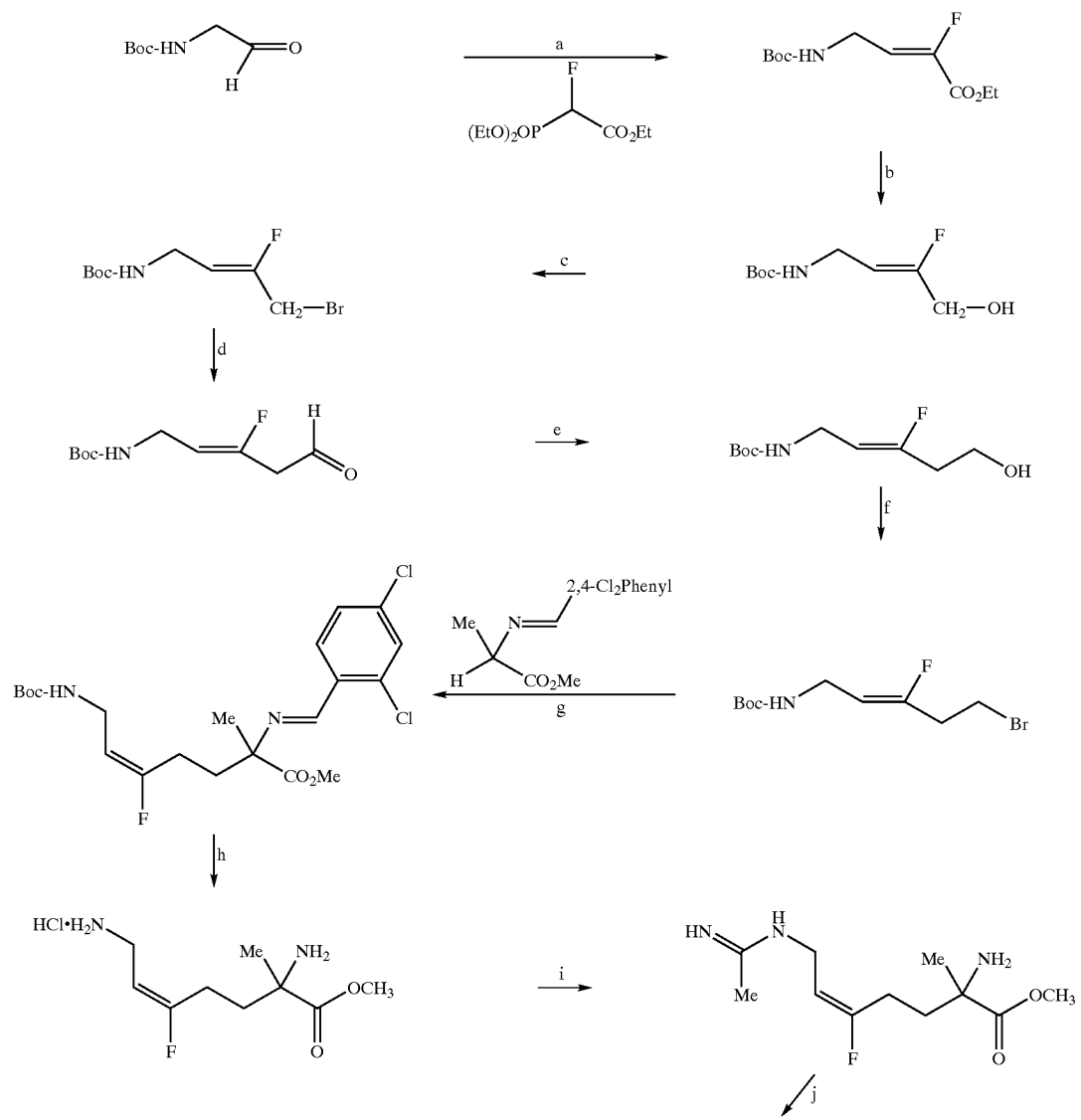

-continued

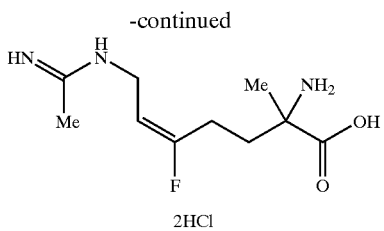

2HCl a) DBU, CH$_2$Cl$_2$
b) LiBH$_4$ (2M in THF)
c) PPh$_3$Br$_2$, pyridine
d) Mg, DMF
e) LiBH$_4$ (2M in THF)
f) PPh$_3$Br$_2$, pyridine
g) NaH, THF
h) 1N HCl
i) Ethylacetamidate, CuCO$_3$
j) 1N HCl, reflux

Example 5

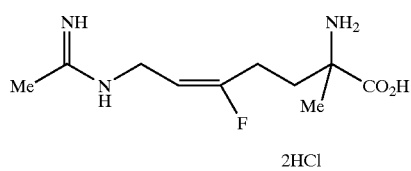

2HCl (2R/S,5E)-2-amino-2-methyl-5-fluoro-7-[(1-iminoethyl)amino]-5-heptenoic acid, Dihydrochloride

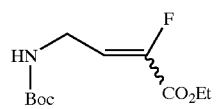

Example-5A

Phosphono fluoroacetate (10.75 mL, 53 mmol) was dissolved in 90 mL methylene chloride and cooled to 0° C. under Argon. DBU (8 mL, 53 mmol) was added. An exotherm was observed raising the temperature to 5° C. The reaction was stirred between 5–10° C. for 10 min. It was then cooled back down to −5° C. N-tertiary butyloxycarbonyl glycinal (7 g, 44 mmol) dissolved in 90 mL of methylene chloride was added drop-wise to the aforementioned anionic solution. The temperature was maintained between 0–5° C. during the addition. The reaction mixture slowly raised to room temperature and was stirred for 12 hours. The resulting mixture was extracted with 175 mL of 0.5 N aqueous potassium bisulfate solution. The organic layer was washed with 50% sodium chloride solution, dried (sodium sulfate), filtered and stripped in vacuo to yield a dark oil which was the title material (10 g, 92% crude yield).

$^1$H NMR (CDCl$_3$) δ 1.3–1.4 (m, 3H), 1.45 (s, 9H), 3.95–4.0 (m, 2H), 4.2–4.4 (m, 2H), 6.0–6.2 (m, 1H)

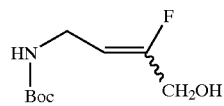

Example-5B

The title material from Example 5A (8.1g, 33mmol) dissolved in tetrahydrofuran under Argon was cooled down to 0° C. Lithium borohydride in tetrahydrofuran (20 mL, 39.6mmol) was then added to this solution dropwise maintaining the temperature between 0–5° C. The reaction mixture slowly rose to room temperature and was stirred for 12 hours. The solvent was removed in vacuo. The residue was then dissolved in 150 mL of methylene chloride and this solution was extracted with 100 mL of 0.5N aqueous potassium bisulfate solution. The organic layer was dried (sodium sulfate), filtered and stripped in vacuo to yield 13 g of a dark oil which was purified on silica gel to give both the Z and E isomer of the title material in a 60/40 ratio and an overall yield (including overlap) of 97%.

Z-isomer:
$^1$H NMR (CDCl$_3$) δ 1.4–1.5 (s, 9H), 3.75–3.85 (m, 2H), 4.24–4.32 (m, 2H), 5.15–5.25 (m, 1H)

E-isomer:
$^1$H NMR (CDCl$_3$) δ 1.4–1.5 (s, 9H), 3.75–3.78 (m, 2H), 4.1–4.15 (m, 2H), 4.95–5.1 (m, 1H)

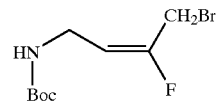

Example-5C

The E-isomer from Example-5B was dissolved in acetonitrile and cooled to 0° C. Pyridine (1.5 eqv) was then added followed by solid dibromotriphenylphosphorane (1.3 eqv) added portion-wise over 10 min. The reaction mixture was stirred under Argon for 24 hours at room temperature. The precipitate formed was filtered off. The filtrate was concentrated in vacuo to give an oil that was purified on silica gel to give the title material.

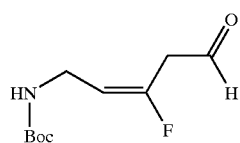

Example-5D

The compound from Example-5B is dissolved in dry Tetrahydrofuran. Magnesium turnings are then added (2 eqv) to the reaction vessel. The reaction mixture is then heated to a reflux and maintained for 1 hour. N,N-Dimethylformamide (2 eqv) is added. The reaction mixture is refluxed for an additional two hours before it is cooled to room temperature. The mixture is filtered and the filtrate is stripped in vacuo to give the title material.

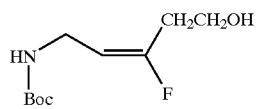

Example-5E

The product from Example-5D is dissolved in Tetrahydrofuran and cooled to 0° C. under nitrogen. Lithium borohydride in THF (1.05 eqv) is then added slowly keeping the temperature between 0–5° C. The temperature of the reaction mixture is then raised to room temperature and the mix is stirred overnight. The solvent is removed in vacuo. The residue is dissolved in methylene chloride and extracted with a 0.5 N aqueous potassium bisulfate solution. The organic layer is washed with 50% sodium chloride solution, dried (sodium sulfate) and stripped to give the title material.

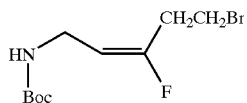

Example-5F

The product of Example-5E is dissolved in acetonitrile. This solution is cooled to 0° C. before pyridine (1.5 eqv) is added. Solid dibromotriphenylphosphorane (1.3 eqv) is then added portion-wise over 10 min. The reaction mixture is stirred under Argon for 24 hours at room temperature. The precipitate formed is filtered off and the filtrate concentrated in vacuo to give an oil that is purified on silica gel to give the desired bromo derivative.

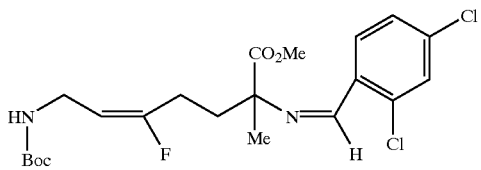

Example-5G

N-p-chloro phenylimine alanine methyl ester is dissolved in tetrahydrofuran and this solution is purged with Argon. NaH (1.2 eqv) is then added whereupon the solution turns bright orange and subsequently a deep red. A solution of the title material from Example-5F in tetrahydrofuran is added to the above anionic solution. An exotherm is expected raising the temperature to near 40° C. The reaction mixture is maintained between 48–52° C. for 2 hours before it is cooled to room temperature and filtered. The filtrate is stripped in vacuo to yield the title material.

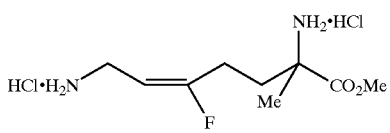

Example-5H

The product of Example-5G is treated with 1N hydrochloric acid and the solution is stirred for an hour at room temperature. This solution is extracted with ethylacetate and the aqueous layer is stripped in vacuo at 56° C. to yield the title material.

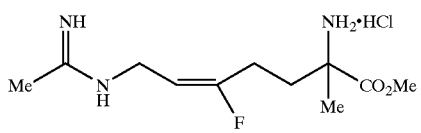

Example-5I

The product of Example-5H is dissolved in distilled water and copper carbonate (0.5 eqv) is then added after the pH is adjusted to 7 with 1N NaOH. The reaction mixture is refluxed for 2 hours and then cooled to room temperature and filtered. Ethyl acetamidate hydrochloride (1.1 eqv) is then added portion-wise to this filtrate with stirring and adjusting the pH to 8.5 after each portion is added. The reaction mixture is then stirred for an hour before it is applied to a cation exchange resin column and eluted with 0.8 N aqueous ammonia. The ammonia is removed from eluant in vacuo. The eluant is subsequently acidified with 2N Hydrochloric acid to pH 2 and concentrated to dryness. The residue is then purified on reverse phase HPLC to yield the title material.

Example-5

The product of Example-5I is dissolved in 2N hydrochloric acid. This reaction mixture is heated to a reflux and stirred for 6 hours before it is cooled to room temperature. The solvent is then removed in vacuo. The residue is dissolved in water and subsequently stripped on the rotary evaporator to remove excess hydrochloric acid. The residue is again dissolved in water and lyophilized to give the title E-isomer product.

Example 6

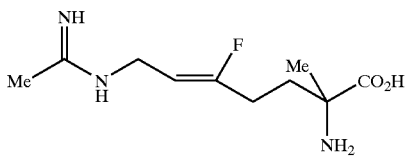

(2R/S,5Z)-2-amino-2-methyl-5-fluoro-7-[(1-iminoethyl)amino]-5-heptenoic acid, Dihydrochloride

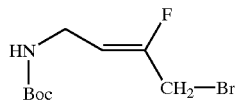

Example 6A

The Z-isomer from Example 5B is dissolved in acetonitrile and this solution was cooled to 0° C. Pyridine (1.5 eqv) is then added followed by the addition of solid dibromotriphenylphosphorane (1.3 eqv) added portion-wise over 10 min. The reaction mixture is stirred under Argon for 24 hours at room temperature. A precipitate formed is filtered off. The filtrate is then concentrated in vacuo to give an oil that is purified on silica gel to give the title material.

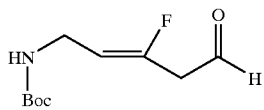

Example 6B

The product of Example 6A is dissolved in dry tetrahydrofuran. Magnesium turnings are then added (2 eqv) to the solution. The reaction mixture heated to a reflux and maintained for 1 hour. N,N-Dimethylformamide (2 eqv) is then added. The reaction mixture is refluxed for an additional two hours, cooled to room temperature and filtered. The filtrate is stripped in vacuo to give the title material.

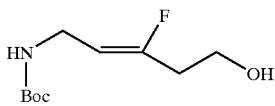

Example 6C

The product of Example 6B is dissolved in tetrahydrofuran and this solution cooled to 0° C. under nitrogen. Lithium borohydride in THF (1.05 eqv) is added slowly keeping the temperature between 0–5° C. The temperature of the reaction mixture is raised to room temperature and the mix is stirred overnight. The solvent is removed in vacuo. The residue is dissolved in methylene chloride and extracted with 0.5 N aqueous potassium bisulfate solution. The organic layer is washed with 50% sodium chloride solution, dried (sodium sulfate) and stripped to give the title material.

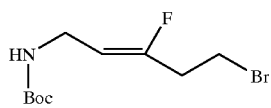

Example 6D

The product of Example 6C is dissolved in acetonitrile and the solution cooled to 0° C. Pyridine (1.5 eqv) is then added followed by solid dibromotriphenylphosphorane (1.3 eqv) added portion-wise. The reaction mixture is stirred under Argon for 24 hours at room temperature. A precipitate formed is filtered off. The filtrate is concentrated in vacuo to give an oil that is purified on silica gel to give the desired title bromo derivative.

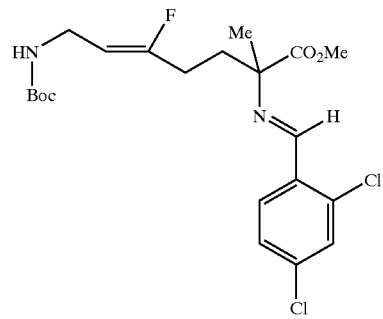

Example 6E

N-p-chloro phenylimine alanine methyl ester is dissolved in tetrahydrofuran and this solution is purged with Argon. NaH (1.2 eqv) is added whereupon the solution turns bright orange and subsequently a deep red. A solution of the product of Example 6D dissolved in tetrahydrofuran is added to the above anionic solution. An exotherm is observed and the reaction mixture is maintained between 48–52° C. for 2 hours. The reaction is cooled to room temperature and filtered. The filtrate is stripped in vacuo to yield the title material.

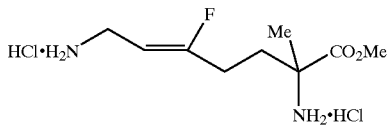

Example 6F

The product of Example 6E is treated with 1N hydrochloric acid and the solution is stirred for an hour at room temperature before it is extracted with ethylacetate. The aqueous layer is stripped in vacuo at 56° C. to yield the title material.

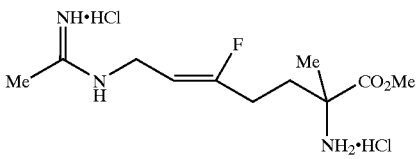

Example 6G

The product of Example 6F is dissolved in distilled water. Copper carbonate (0.5 eqv) is added after the pH was adjusted to 7 with 1N NaOH. The reaction mixture is refluxed for 2 hours and then cooled to room temperature and filtered. Ethyl acetamidate hydrochloride (1.1 eqv) is added portion-wise to this filtrate with stirring and adjusting the pH to 8.5 after every portion added. The reaction mixture is stirred for an hour before it is applied to a cation exchange resin column, eluting with 0.8 N aqueous ammonia. The ammonia is removed from eluant in vacuo. The eluant is subsequently acidified with 2N Hydrochloric acid to pH 2 and concentrated to dryness. The residue is purified on reverse phase HPLC to yield the title material.

Example 6

A solution the product of Example 6G dissolved in 15 mL of 2N hydrochloric acid is heated to a reflux and stirred for 6 hours. After cooling this solution to room temperature, solvent is removed in vacuo. The residue is dissolved in 25 mL of water and stripped on the rotary evaporator to remove excess hydrochloric acid. The residue is dissolved in water and lyophilized to give the title Z-isomer.

Example 7

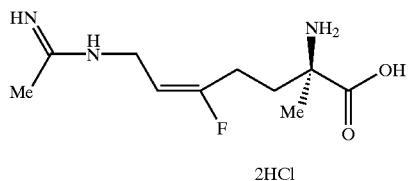

2HCl (2R,5E)-2-amino-2-methyl-5-fluoro-7-[(1-iminoethyl)amino]-5-heptenoic acid, Dihydrochloride

Example 8

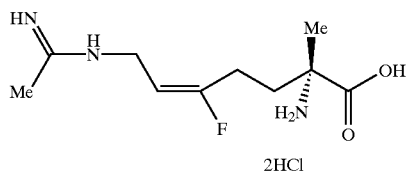

2HCl (2S,5E)-2-amino-2-methyl-5-fluoro-7-[(1-iminoethyl)amino]-5-heptenoic acid, Dihydrochloride Scheme 8

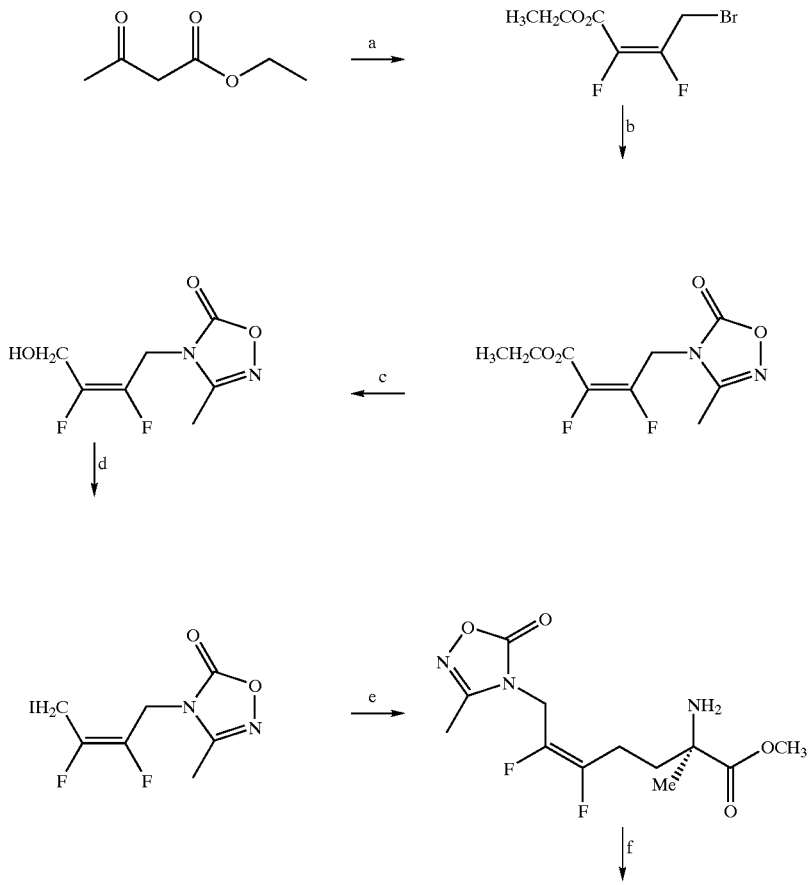

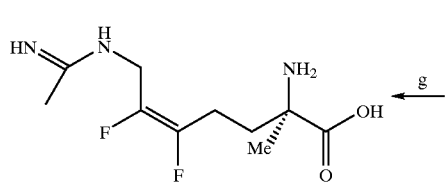
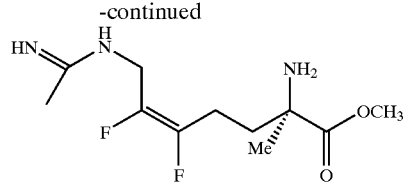

a) 1. DAST
   2. NBS, benzoylperoxide
b) Potassium salt of 3-methyl-1,2,4-oxadiazolin-5-one, DMSO, heat
c) DIBAL—H, THF
d) methylene chloride, PPh₃, imidazole, I₂
e) Zn/CuI/CuCN, THF; methyl (S)-2-iodomethyl-N-Boc-alaninate
f) Zn dust, acetic acid, water, heat
g) aqueous HCl, heat Example 9

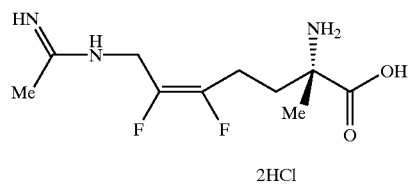

(2S,5Z)-2-amino-2-methyl-5,6-difluoro-7-[(1-iminoethyl)amino]-5-heptenoic acid, Dihydrochloride Example 10

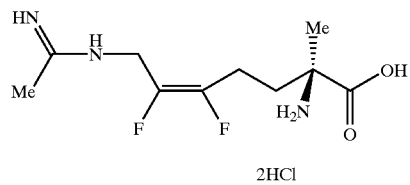

(2R,5Z)-2-amino-2-methyl-5,6-difluoro-7-[(1-iminoethyl)amino]-5-heptenoic acid, Dihydrochloride Example 11

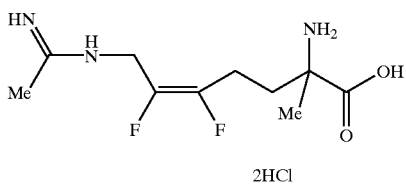

(2R/S,5Z)-2-amino-2-methyl-5,6-difluoro-7-[(1-iminoethyl)amino]-5-heptenoic acid, Dihydrochloride Scheme 9

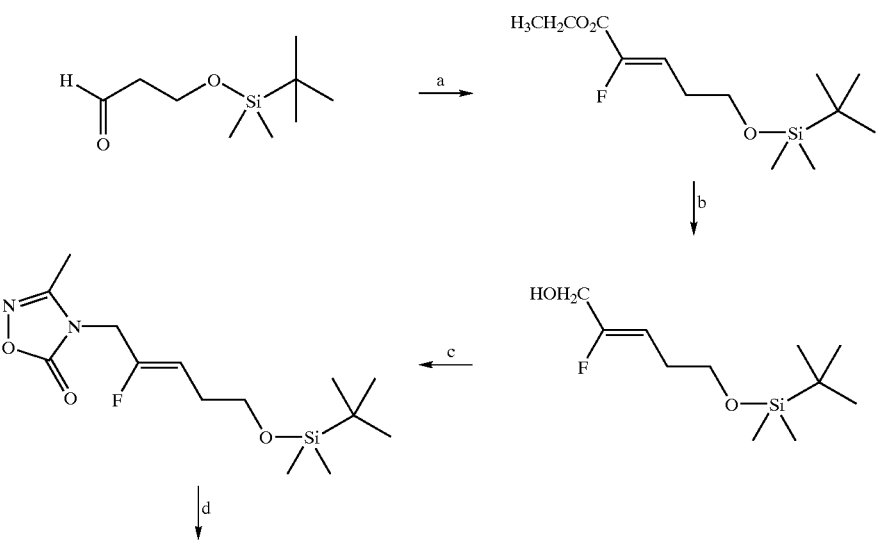

-continued

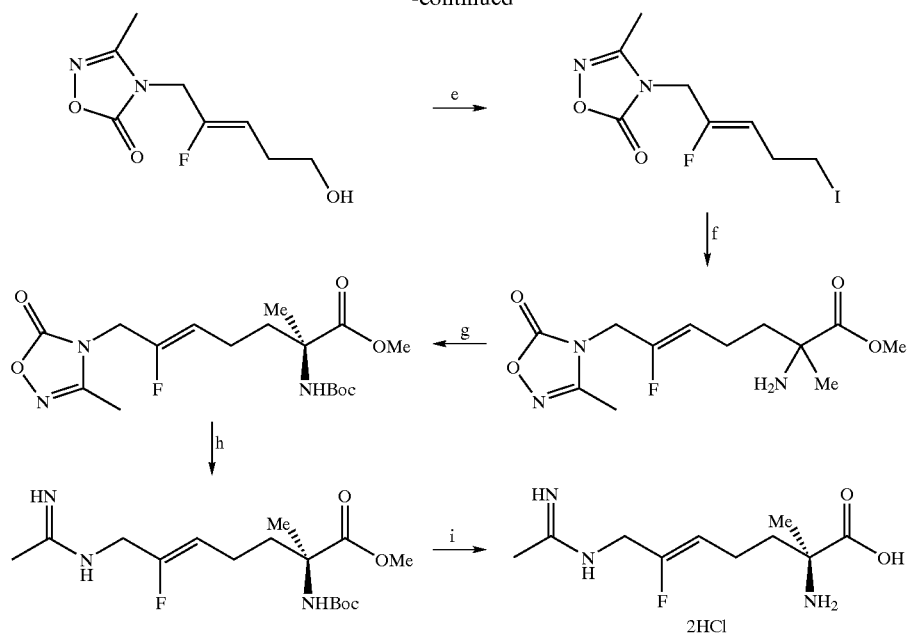

a) triethyl 2-fluorophosphonoacetate, DBU, THF and hexane
b) NaBH$_4$, methanol, water
c) polymer-supported triphenylphosphine, 3-methyl-1,2,4-oxadiazolin-5-o ne, diethylazodicarboxylate, THF
d) acetic Acid:THF:H$_2$O (3:1:1)
e) methylene chloride, PPh$_3$, imidazole, I$_2$
f) 1. NMP, BEMP, methyl N-[(4-chlorophenyl)methylene]alaninate. 2. aq ueous HCl
g) 1. CH$_2$Cl$_2$, di-*t*-butyl carbonate, triethylamine
   2. Chiral chromatography
h) Zn dust, acetic acid, methanol, heat
i) aqueous HCl, heat

Example 12

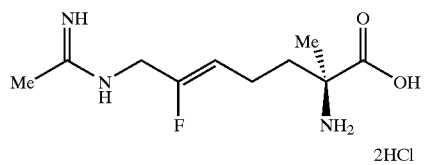

(2S,5Z)-2-amino-2-methyl-6-fluoro-7-[(1-iminoethyl)amino]-5-heptenoic acid, Dihydrochloride Scheme 10

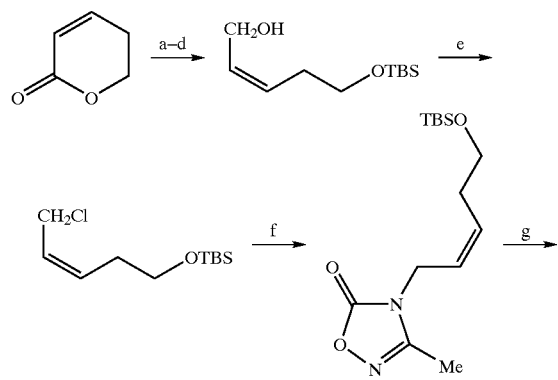

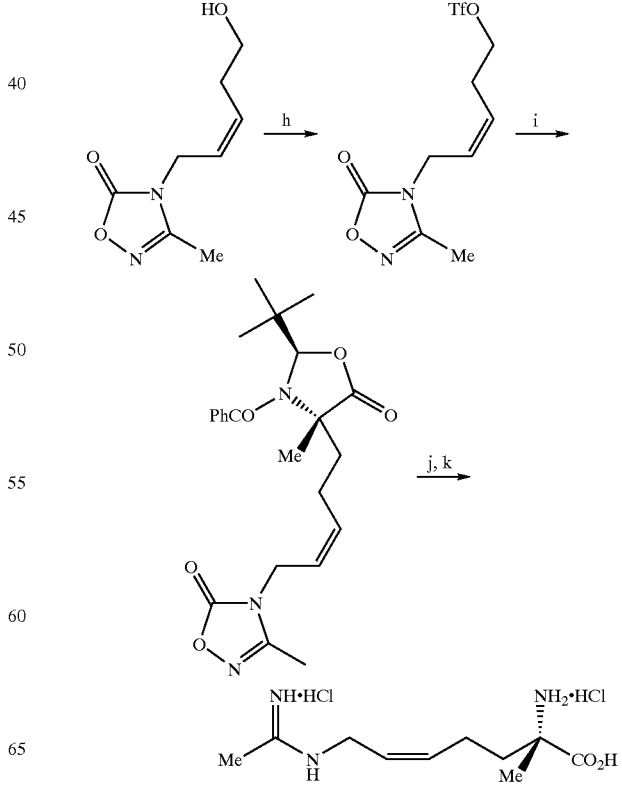

-continued a) KOH
b) MeI
c) TBSCl
d) DIBAL
e) MsCl
f) 3-methyl-1,2,4-oxadiazolin-5-one potassium salt
g) AcOH
h) Tf₂O
i) KHMDS/(2 S,4 S)-3-benzoyl-2-t-butyl-4-methyl-,3-oxazolidin-5-one
j) Lindlar catalyst
k) 6N HCl Example 13

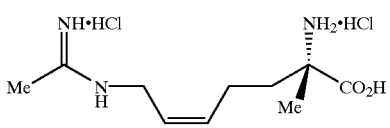

(2S,5Z)-2-amino-2-methyl-7-[(1-iminoethyl)amino]-5-heptenoic acid, Dihydrochloride

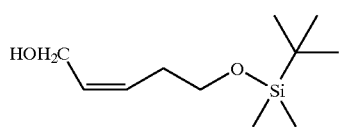

Example-13A

The title compound, (Z)-5-t-butyldimethylsilyloxy-2-penten-1-ol, was prepared from 5,5-dihydro-2-pyrone (Aldrich) by the method of Harold, Mohr and Tamm *Helvetica Chimica Acta* 66,2, 1983 744–754.

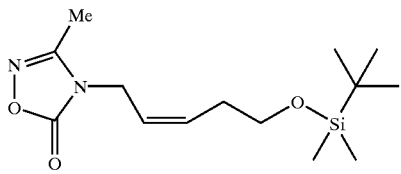

Example-13B

To a solution of Example-13A (720 mg, 3.3 mmol) in CH₂Cl₂ (25 mL) was added Et₃N (525 mg, 5.3 mmol) and methanesulfonyl chloride (561 mg, 4.90 mmol). The reaction mixture was stirred for 15 min at 0° C. then at room temperature for 16 h. Additional CH₂Cl₂ was added. The solution was extracted with NaHCO₃ and brine before it was dried to yield 790 mg of a yellow oil. The oil was dissolved in DMF (20 mL) and Na salt of 3-methyl-1,2,4-oxadiazolin-5-one (513 mg, 3.7 mmol) was added to the reaction mix. The resulting solution was stirred at 50° C. for 16 h. The solvent was removed in vacuo and the residue partitioned between EtOAc and brine. The organic layer was dried (Na₂SO₄) and concentrated to yield an oil which was purified by flash column chromatography on silica gel eluting with ether:hexane (1:1) to give 780 mg (79%) of the desired protected Z-allylic cyclic amidine product as a clear oil that contained only the desired Z-isomer by ¹HNMR.

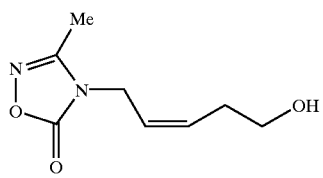

Example-13C

A solution of Example-13B (100 mg, 0.34 mmol) in a mixture of acetic acid (1 mL), THF (3 mL) and water (1 mL) was stirred at room temperature for 16 hours. The resulting solution was concentrated in vacuo to an oil which was dissolved in EtOAc. The organic layer was washed with saturated NaHCO₃, dried (Na₂SO₄), filtered and evaporated to give 80 mg (quant.) of the desired alcohol title product as a clear colorless oil.

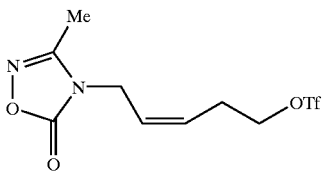

Example-13D

To a CH₂Cl₂ (3 mL) solution of Example-13C (80 mg, 0.43 mmol) was added Et₃N (44 mg) and triflic anhydride (146 mg, 0.52 mmol) at 0° C., the mixture was stirred for 1.5 h. The solution was concentrated in vacuo. The crude material was purified by flash column chromatography on silica gel eluting with EtOAc:hexane (1:1) to give 62 mg (44%) of the desired triflate product as a clear oil.

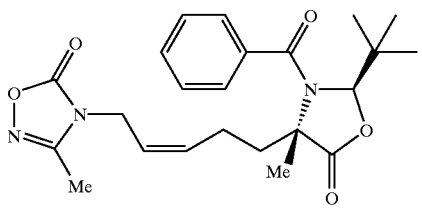

Example-13E

To a THF (10 mL) solution of (2S,4S)-3-benzoyl-2-t-butyl-4-methyl-1,3-oxazolidin-5-one (Ref.) (532 mg, 2.04 mmol) at −78° C. was added KHMDS (4.48 mL, 2.2 mmol, 0.5 M in THF). The resulting orange colored solution was stirred for 15 min. followed by the addition of the product of Example 13D (580 mg, 1.8 mmol). The resulting solution was allowed to warm to room temperature followed by the addition of KHSO₄ (10%, 1.5 mL) brine and EtOAc. The organic layer was separated, dried and concentrated in vacuo to yield 960 mg of a yellow oil. The crude material was purified by flash column chromatography on silica gel eluting with EtOAc:hexane (1:1) to give 138 mg (18%) of the desired alkylated title product as a clear oil.

Example-13

To a methanol (10 mL) solution of the product of Example-13E (138 mg, 0.32 mmol) was added Lindlar catalyst (260 mg). The stirred slurry was refluxed for 2 hours and then cooled to room temperature. The catalyst was removed by filtration through celite, and the filtrate was stripped to give the desired deprotected amidine product as a pale yellow oil. A solution of the yellow oil in HCl (6N, 10 mL) was refluxed for 1.75 hours. The solvent was removed in vacuo, and the resulting foam was purified by reverse-phase HPLC eluting with a 30 minute gradient of 0–40% $CH_3CN/H_2O$(0.25% acetic acid). Fractions containing product were combined and concentrated to a foam. To give 34 mg (20%) of the title product.

MS calcd. for $C_{10}H_{19}N_3O_2$: m/z=214 [M+H]+. found: 214. (100%)

The monhydrochloride product was dissolved in 1 N HCl and the solvent removed in vacuo (2×) to give the desired (2S,5Z)-2-amino-2-methyl-7-[(1-iminoethyl)amino]-5-heptenoic acid, dihydrochloride product.

MS calcd. for $C_{10}H_{19}N_3O_2$: m/z=214 [M+H]+. found: 214 (100%). $^1$H NMR ($D_2O$) δ 1.40 (s, 3H), 1.5–2.0 (m, 4H) 1.90 (s, 3H), 3.55 (m, 2H) 5.15–5.25 (m, vinyl, 1H), 5.30–5.45 (m, vinyl, 1H).

Scheme 11

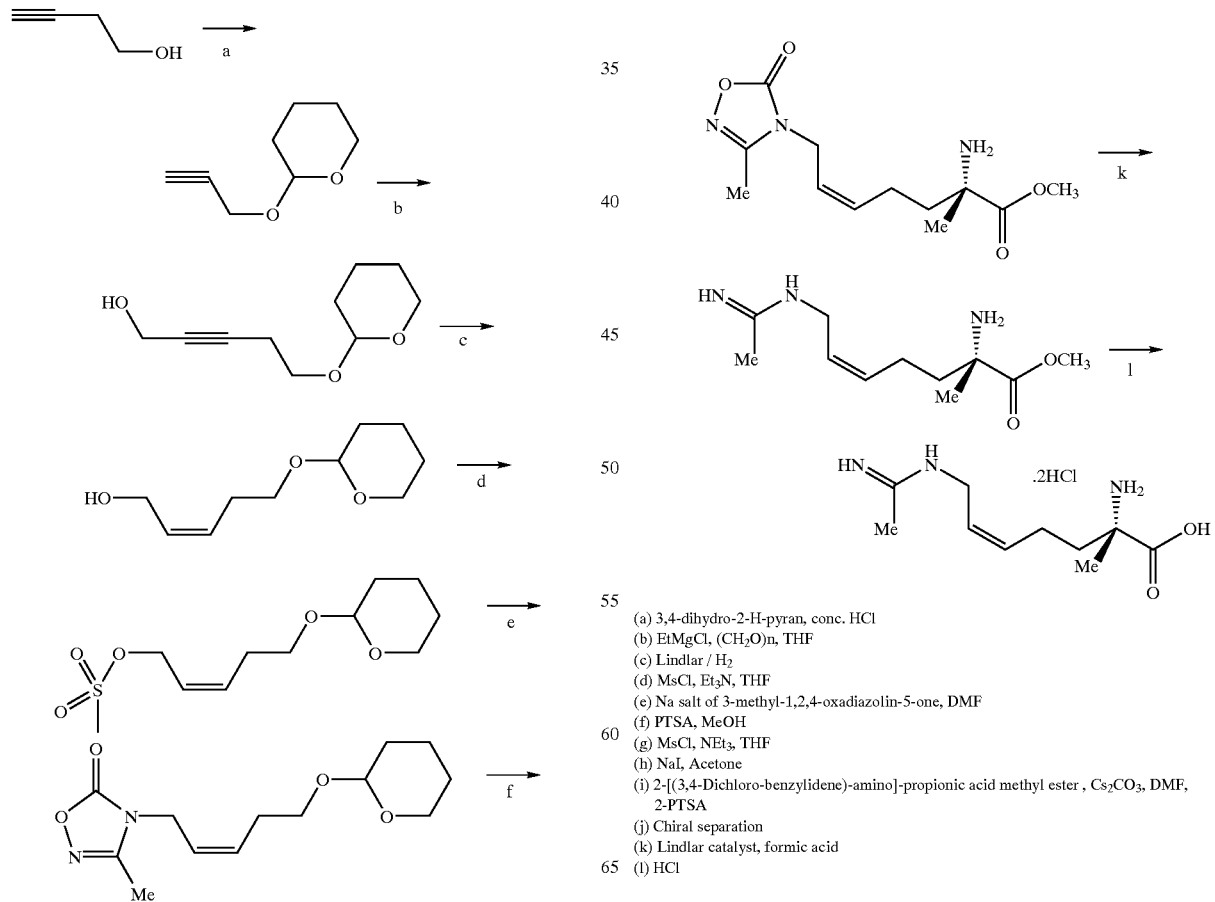

(a) 3,4-dihydro-2-H-pyran, conc. HCl
(b) EtMgCl, $(CH_2O)n$, THF
(c) Lindlar / $H_2$
(d) MsCl, $Et_3N$, THF
(e) Na salt of 3-methyl-1,2,4-oxadiazolin-5-one, DMF
(f) PTSA, MeOH
(g) MsCl, $NEt_3$, THF
(h) NaI, Acetone
(i) 2-[(3,4-Dichloro-benzylidene)-amino]-propionic acid methyl ester, $Cs_2CO_3$, DMF, 2-PTSA
(j) Chiral separation
(k) Lindlar catalyst, formic acid
(l) HCl

Example 14

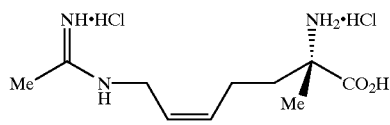

(2S,5Z)-2-amino-2-methyl-7-[(1-iminoethyl)amino]-
5-heptenoic acid, Dihydrochloride

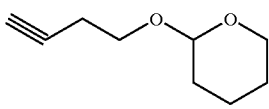

4-[(Tetrahydropyranyl)oxy]butyne

Example 14A

A mixture of 4-dihydro-2H-pyridine (293.2 g 3.5 mol) and concentrated HCl (1.1 mL) was cooled to 5° C. While continuing to cool externally, 3-butyn-1-ol (231.5 g, 3.3 mol) was added over a period of 30 minutes allowing the temperature to reach 50° C. Reaction was held with mixing at room temperature for 2.5 hours before it was diluted with MTBE (1.0 L). The resulting mixture was washed with saturated sodium bicarbonate (2×150 mL). The organic phase was dried over sodium sulfate and concentrated under reduced pressure to afford 500 g (98% crude yield) of product; GC area % of 96%.

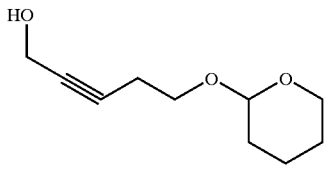

5-(Tetrahydro-pyran-2-yloxy)-pent-2-yn-1-ol

Example 14B

To a solution of the 4-[(tetrahydropyranyl)oxy]butyne product of Example 14A (50.0 g, 0.33 mol) in THF (125 mL) was added a solution of 2N EtMgCl in THF (242 mL, 0.48 mol) under a nitrogen atmosphere over a 30 minute period, allowing the temperature to rise to 48° C. Mixture was further heated to 66° C. and was held at this temperature for 2 hours before cooling to ambient temperature. Paraformaldehyde (14.5 g, 0.48 mol) was added (small exotherm was observed) and the resulting mixture was heated to 45° C. After 1 hour of controlling the temperature between 45–55° C., the mixture turned clear. At this point, the mixture was heated up to 66° C. and stirred for 2.5 hours. Mixture was cooled to room temperature and saturated ammonium chloride (125 mL) was added slowly over 30 minutes (strong exotherm was observed) keeping the temperature below 40° C. The liquid phase was separated by decantation; ethyl acetate (250 mL) and brine (50 mL) were added. The organic phase was separated and washed with brine (2×50 mL) and water (1×50 mL). The organic layer was dried over sodium sulfate and concentrated under reduced pressure to afford 51 g of a lightly yellow colored oil (85% crude yield); GC area%=88% title product, 6% starting material.

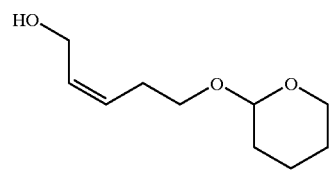

5-(Tetrahydro-pyran-2-yloxy)-pent-2-en-1-ol

Example 14C

To a 500 mL Parr bottle, under a nitrogen atmosphere, was charged the 5-(tetrahydro-pyran-2-yloxy)-pent-2-yn-1-ol product of Example 14B (40.2 g, 0.22 mol), Lindlar catalyst (2.0 g), ethanol (120 mL), hexane (120 mL), and 2,6-lutidine (457 mg). Reaction mixture was purged five times each with nitrogen and hydrogen gas. Parr bottle was pressurized with hydrogen to 5 psi and shaken until 98% of the theoretical hydrogen was consumed. Hydrogen was released from the vessel and the reaction was purged with nitrogen five times. Mixture was filtered through a pad of Solka Floc and the catalyst was rinsed with ethanol (2×50 mL). The filtrate and rinses were combined and concentrated under reduced pressure to afford 40.3 g (99% yield) of the title material as a yellow colored oil (GC area %=96%).

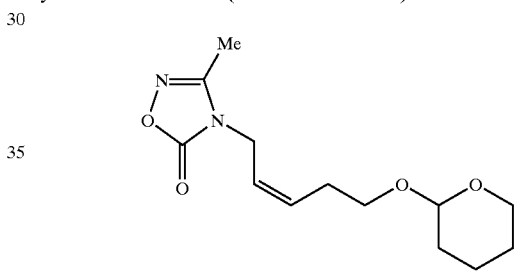

3-Methyl-4-[5-(tetrahydro-pyran-2-yloxy)-pent-2-
enyl]-4H-[1,2,4]oxadiazol-5-one

Example 14D

To a solution of the 5-(tetrahydro-pyran-2-yloxy)-pent-2-en-1-ol product of Example 14C (11.8 g, 0.063 mol) in toluene (42 mL) was added) triethylamine (6.4 g, 0.063 mol). The mixture was cooled to −5° C. and methanesulfonyl chloride (7.3 g, 0.63 mol) was added via syringe at such rate as to keep the pot temperature below 10° C. The mixture was allowed to warm to room temperature and stirred for two hours. The mixture was filtered by suction and rinsed on the filter with toluene (2×20 mL). The filtrate and washes were added to a mixture of the sodium salt of 3-methyl-1,2,4-oxadiazolin-5-one (8.6 g, 0.063 mol) in DMF (10 mL). The mixture was stirred with a mechanical stirrer and heated at 45° C. for 5 hours. Water (40 mL) was added and the mixture was stirred for 5 minutes and then the layers were separated. The toluene layer was washed with water (3×20 mL), dried over MgSO$_4$, and concentrated to afford 16.5 g (97.3%) of an orange colored crude product (area % GC consisted of 71% title product, 18% toluene, and 4% of an impurity).

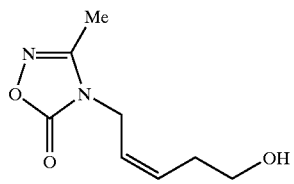

4-(5-Hydroxy-pent-2-enyl)-3-methyl-4H-[1,2,4]oxadiazol-5-one

Example 14E

To a solution the 3-methyl-4-[5-(tetrahydro-pyran-2-yloxy)-pent-2-enyl]-4H-[1,2,4]oxadi-az-ol-5-one product of Example 14D (16 g, 0.06 mol) in methanol (48 mL) was added p-toluenesulfonic acid (0.34 g, 2.0 mmol). The mixture was stirred at room temperature for four hours. Sodium bicarbonate (0.27 g, 3.0 mmol) was added and the mixture was concentrated on a rotary evaporator. The residue was diluted with saturated $NaHCO_3$ (20 mL) and the resulting mixture was extracted with ethyl acetate (2×60 mL). Extracts were combined and washed with water (2×25 mL), dried over $MgSO_4$, and concentrated to afford 8.4 g of the crude, orange colored oil title product (area % GC=80%).

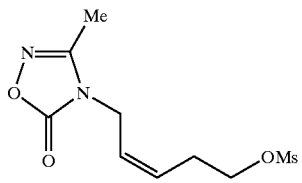

Methanesulfonic Acid 5-(3-methyl-5-oxo-[1,2,4]oxadiazol-4-yl)-pent-3-enyl ester

Example 14F

To a solution of the 4-(5-Hydroxy-pent-2-enyl)-3-methyl-4H-[1,2,4]oxadiazol-5-one product of Example 14E (8.27 g, 0.045 mol) in methylene chloride (33 mL) was added triethylamine (5.0 g, 0.49 mol). The mixture was cooled to −5° C. and methanesulfonyl chloride (5.5 g, 0.048 mol) was added at such rate as to keep the temperature below 8° C. The cooling bath was removed and the mixture was stirred for 3 hours as it warmed up to room temperature. Water (15 mL) was added and the mixture was stirred for 5 minutes and then the layers were separated. The organic phase was washed with water (10 mL), dried over $MgSO_4$, and concentrated to give a light amber colored residue. The residue was dissolved in ethyl acetate (8 mL) and kept at 5° C. overnight. Precipitated solids were filtered off by suction and rinsed on the filter with minimum volume of ethyl acetate and then air-dried on the filter to afford 6.8 g (58% yield) of the title product.

$^1$H NMR (CDCl$_3$) δ 5.76 (dtt, J=10.9, 7.5, 1.5 Hz, 1H), δ 5.59 (dtt, J=10.9, 7.0, 1.5 Hz, 1H), δ 6 4.31 (t, J=6.3 Hz, 2H), δ 4.27 (dd, J=7.0, 1.5 Hz, 2H), δ 3.04 (s, 3H), δ 2.67 (q, J=6.7 Hz, 2H), δ 2.28 (s, 3H) $^{13}$C (CDCl$_3$) δ 159.0, 156.3, 129.9, 125.1, 68.4, 38.9, 37.2, 27.5, 10.2. IR (cm$^{-1}$) 1758, 1605, 1342, 1320, 1170. Anal. Calcd. for C$_9$H$_{14}$N$_2$O$_5$S: C, 41.21; H, 5.38; N, 10.68. Found: C, 41.15; H, 5.41; N, 10.51.

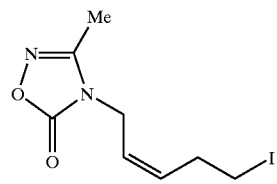

4-(5-Iodo-pent-2-enyl)-3-methyl-4H-[1,2,4]oxadiazol-5-one

Example 14G

To a solution of the methanesulfonic acid 5-(3-methyl-5-oxo-[1,2,4]oxadiazol-4-yl)-pent-3-enyl ester product of Example 14F (20.0 g, 0.076 mol) in acetone (160 ml) was added sodium iodide (17.15 g, 0.114 mol). The mixture was heated to reflux and was stirred for 3 hours. External heating was stopped and the mixture was held at room temperature overnight. Solids were removed by filtration and rinsed on the filter. The filtrate and washes were combined and concentrated and the heterogeneous residue was extracted with ethyl acetate (120 mL). The organic layer was washed with water (60 mL), 15% aqueous solution of sodium thiosulfate (60 mL) and water (60 mL); dried over $MgSO_4$ and concentrated under reduced pressure to afford 22.1 g (98% yield) of the title oil product.

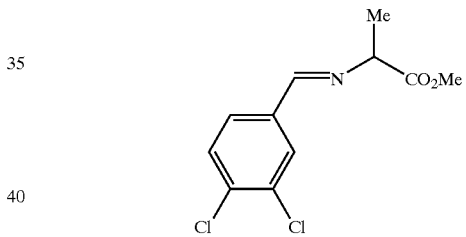

2-[(3,4-Dichloro-benzylidene)-amino]-propionic acid methyl ester

Example 14H

To a mechanically stirred slurry of L-alanine methyl ester hydrochloride (200.0 g, 1.43 mol) in methylene chloride (2.1 L) under a nitrogen atmosphere was added triethylamine (199.7 mL, 1.43 mol) over 12 min (during the addition solids partially dissolved and then reprecipitated). After 10 min, 3,4-dichlorobenzaldehyde (227.5 g, 1.30 mol) and magnesium sulfate (173.0 g, 1.43 mol) were added (temperature increased 6° C. over 30 min). After 2.5 h, the mixture was filtered. The filtrate was washed with water (1×1 L) and brine (1×500 mL), dried over sodium sulfate, filtered and concentrated to give 313.3 g, 92.4% yield of oil product.

$^1$H NMR (400 MHz, CDCl13) δ 8.25 (s, 1H), 7.91 (d, 1H), 7.58 (dd, 1H), 7.49 (d, 1H), 4.17 (t, 1H), 3.76 (s, 3H), 1.53 (d, 3H). Anal. Calcd for C$_{11}$H$_{11}$Cl$_2$NO$_2$: C, 50.79; H, 4.26; Cl, 27.26; N, 5.38. Found: C, 50.37; H, 4.10; Cl, 26.87; N, 5.38.

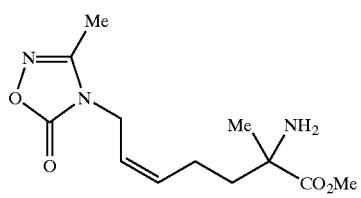

Rac-2-Amino-2-methyl-7-(3-methyl-5-oxo-[1,2,4]oxadiazol-4-yl)-hept-5-enoic acid methyl ester Example 14I Method A. A solution of the product of Example 14G (114.2 g, 0.39 mol) and the product of Example 14H (151.5 g, 0.58 mol) in dimethylformamide (1.4 L) under nitrogen atmosphere was cooled to −8 ° C. Lithium iodide (78.1 g, 0.58 mol) was then added in 3 equal portions over 19 min. The mixture was stirred for 20 min at −7° C. and then (tert-butylimino)-tris(pyr-rolidino)phosphorane (194.0 mL, 0.62) was added over 36 min (maximum temperature=−2.6° C). After 10 min, the cooling bath was removed and the solution was stirred at ambient temperature for 1 h. The mixture was then poured into cold water (1.4 L) and extracted with ethyl acetate (2×1.0 L). The combined organic layers were washed with water (2×400 mL) and brine. The ethyl acetate layer was treated with 1 N HCl (780 mL) and stirred for 1 h. The aqueous layer was separated and extracted with ethyl acetate (2×400 mL) and then neutralized with sodium bicarbonate (110 g). The mixture was extracted with ethyl acetate (1×500 mL). The organic layer was dried over sodium sulfate, filtered, concentrated and then treated with methyl t-butyl ether to give a crystalline product: first crop 14.4 g; second crop 6.6 g (GC purity=96.2 and 91.9%, respectively). The aqueous phase was saturated with sodium chloride and extracted with ethyl acetate (4×500 mL). The combined organic layers were dried over sodium sulfate, filtered, concentrated and then treated with methyl t-butyl ether to give a crystalline product: first crop 33.4 g; second crop 10.8 g (GC purity=89.6 and 88.8%, respectively). Total crude yield 65.2 g, 62.4%.

Method B. To a solution of the product of Example 14G (20.7 g, 0.070 mol) and the product of Example 14H (22.9 g, 0.088 mol) in dimethylformamide (207 mL) under a nitrogen atmosphere was added cesium carbonate (29.8 g, 0.092). The mixture was stirred at rt for 16 h and then diluted with water (300 mL) and extracted with ethyl acetate (2×200 mL). The combined ethyl acetate layers were washed with water (3×100 mL) and brine and then treated with 1 N HCl (184 mL). After 1 h, the layers were separated and the aqueous layer was extracted with ethyl acetate (3×100 mL) and then neutralized with sodium bicarbonate (15.5 g). The mixture was extracted with ethyl acetate (1×150 mL). The aqueous layer was saturated with sodium chloride and extracted with ethyl acetate (3×100 mL). The combined organic layers were dried over sodium sulfate, filtered and concentrated to give a yellow solid, 11.9 g, 62.9%; GC purity=96.6%. The crude product was recrystallized from warm methyl t-butyl ether or ethyl acetate.

$^1$H NMR (400 MHz, CDCl$_3$) δ 5.68 (m, 1H), 5.36 (m, 1H), 4.23 (d, 2H), 3.73 (s, 3H), 2.43 (s, 3H), 2.18 (m, 2H), 1.81 (m, 1H), 1.69 (s, br, 2H), 1.66 (m, 1H), (1.36, 3H) $^{13}$C NMR (400 MHz, CDCl$_3$) δ 177.60, 159.01, 156.10, 135.12, 121.82, 57.48, 52.29, 40.12, 39.00, 26.62, 22.56, 10.41

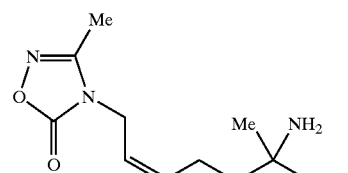

Rac-2-Amino-2-methyl-7-(3-methyl-5-oxo-[1,2,4]oxadiazol-4-yl)-hept-5-enoic acid

Example 14J

The product of Example 14J (0.269g, 1 mmol) was dissolved in 5 mL 2 N HCl and heated to reflux under argon. After refluxing for 6 hrs followed by stirring at room temperature for 72 hours, an aliquot was removed and checked by $^1$H NMR. Approximately 6% of unreacted starting ester remained along with the desired product (verified by LC-MS). The aqueous portion was removed in vacuo, leaving 0.38 g of a thick, amber oil. After purification via reverse phase chromatography, followed by lyophilization, one obtained 0.23 g, 90.2% of the title compound as white, non-deliquescent solids.

Anal. Calcd. for C$_{11}$H$_{17}$N$_3$O$_4$0.77H$_2$O: C, 49.09; H, 6.94; N, 15.61. Found: C, 48.71; H, 6.94; N, 15.98. Mass spec: M+1=256.

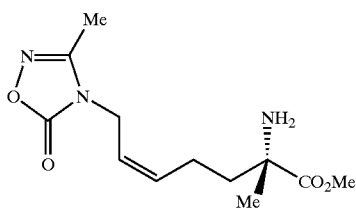

(2S,5Z)-2-Amino-2-methyl-7-(3-methyl-5-oxo-[1,2,4]oxadiazol-4-yl)-hept-5-enoic acid methyl ester Example 14K The title compound (827.3 g) was separated from its R enantiomer by preparative chiral chromatography using Novaprep 200 instrument with steady state recycling option. The material was dissolved in absolute ethanol at a concentration of 40 mg/ml and loaded on a 50×500 mm prepacked Chiral Technologies stainless steel column. The adsorbent was 20 μ ChiralPak AD. The mobile phase was ethanol/triethylamine 100/0.1; the flow rate equaled 125 ml per min. The crude solution (25 mL) was loaded on the column every 12 mins. A steady state recycling technique was used. Solvent was removed using a rotovap. The final product was isolated as gold oil which solidified on standing; 399.0 g (96.4% recovery).

$^1$H (400 MHz, CD$_3$OD) δ 5.68 (dtt, 1H, J$_{olefinic}$=10.7 Hz), 5.43 (dtt, 1H, J$_{olefinic}$=10.7 Hz), 4.82 (s, br, 2H), 4.28 (d, 2H, J=5.5 Hz), 3.73 (s, 3H), 2.27 (s, 3H), 2.26 (m, 1H), 2.14

(m,1H), 1.82 (ddd, 1H, J=13.6,11.3, 5.4 Hz), 1.67 (ddd, 1H, J=13.6, 11.2, 5.5 Hz), 1.34 (s, 3H) $^{13}$C NMR (400 MHz, CD$_3$OD) δ 178.49, 161.13, 158.70, 135.92, 123.47, 58.55, 52.77, 41.38, 39.96, 26.23, 23.47, 10.23 Anal. Calcd for C$_{12}$H$_{19}$N$_3$O$_4$: C, 53.52; H, 7.11; N, 15.60. Found: C 52.35; H, 7.20; N, 15.60.

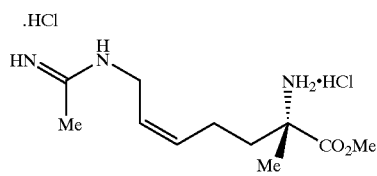

(2S,5Z)-7-Acetimidoylamino-2-amino-2-methyl-hept-5-enoic acid methyl ester, Dihydrochloride hydrate Example 14L To a solution of the product of Example 14K (114.5 g, 0.425 mol) in methanol (2.4 L) was added the solid dibenzoyl-L-tartaric acid (152.5 g, 0.425 mol) and 88% formic acid (147 mL, 3.428 mol) at ambient temperature. A slurry of Lindlar catalyst, 5 wt % palladium on calcium carbonate poisoned with lead acetate (37.9 g), in methanol (200 mL) was prepared under nitrogen. The solution of starting material was then added at ambient temperature to the light grey catalyst slurry followed by a methanol rinse (200 mL). The heterogeneous reaction mixture was heated at 45° C. for 1½ hours. Steady gas evolution was observed starting at about 40° C., which indicated the ongoing reaction. The mixture was cooled in an ice/water bath and then filtered through a plug of Supercell HyFlo. The yellow solution was concentrated in vacuo to give a viscous oil, which was dissolved and partitioned between 2 N aqueous HCl (2 L) and ethyl acetate (0.8 L). Layers were separated and the aqueous layer was washed once with ethyl acetate (0.8 L). Solvent and volatiles were removed in vacuo at elevated temperatures (=70° C.). The intermediate product was used in next the step without further purification or characterization. LC–MS [M+H]$^+$=228.

Example 14

The crude product of Example 14L (170 g) was dissolved in 2 N aqueous HCl (1 L). The resulting orange solution was refluxed overnight before it was allowed to cool back to ambient temperature. The reaction mixture was concentrated to about ⅓ of its volume, and the acidic solution was passed through a solid phase extraction cartridge (25 g of C18 silica) to remove color and other impurities. Solvent was removed in vacuo (=70° C.) to give 208 g of crude product as yellowish gum.

The crude gum (31.3 g) was taken up in water (250 mL) and the material was loaded onto a pretreated ion exchange column packed with the acidic resin Dowex 50WX4–400 (about 600 g). The resin was first washed with water (1 L), then with dilute aqueous HCl (1 L of 10/90 v/v conc. HCl/water). The product was eluted off the resin with higher ion strength aqueous HCl (1.5 L of 20/90 v/v to 25/75 v/v conc. HCl/water). The aqueous solvent was removed in vacuo (=70° C.), and the gummy residue was taken up in 4 vol % aqueous trifluoroacetic acid (100 mL). The aqueous solvent was removed in vacuo (=70° C.), and the procedure was repeated once more. The residue was then dried under high vacuum to give 32.2 g of gum as the trifluoroacetic acid salt.

Crude (2S,5Z)-7-acetimidoylamino-2-amino-2-methyl-hept-5-enoic acid, ditrifluoroace-tic acid salt hydrate (32.2 g) was purified by reverse-phase preparative chromatography. The crude was dissolved in 0.1% aqueous TFA (50 ml) and loaded onto a 2-inch ID×1 meter stainless steel column packed with adsorbent (BHK polar W/S, 50 μ, 1.16 kg). The product was eluted at a flow rate of 120 mL/min with a step gradient from 0.1% aqueous TFA to 25/75/0.1 acetonitrile/water/TFA. The loading ratio was 36:1 w/w silica to sample. Solvent was removed in vacuo, and the material was converted into the HCl salt by repeated rinses with dilute aqueous HCl and solvent removals in vacuo. Drying under high vacuum gave 27.4 g of the title dihydrochloride hydrate as yellowish gum.

LC–MS [M+H]$^+$=214.16 Da $^1$H NMR (D$_2$O, δ): 1.48 (s, 3H), 1.8–1.9 (AB, 2H), 2.10 (s, 3H), 2.01/2.12 (AB, 2H), 3.78 (d, 2H), rotamere 3.87 (d, 2H), 5.6/5.5 (dt, 2H, 11 Hz) $^{13}$C NMR (D$_2$O) δ: 18.7, 21.5, 21.6, 36.4, 39.1, 59.8, 122.6, 134.3, 164.5, 173.7 Elemental Anal. Calcd. for C$_{10}$H$_{19}$N$_3$O$_2$. 2.2HCl. 2 H$_2$O: C, 36.21; H, 8.33; N, 12.67; Cl 23.51. Found: C, 36.03; H, 7.72; N, 12.67; Cl, 23.60.

Example 15

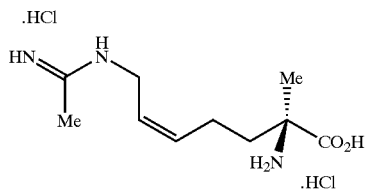

(2R,5Z)-2-amino-2-methyl-7-[(1-iminoethyl)amino]-5-heptenoic acid, Dihydrochloride The R-enantiomer isolated during the separation described in Example 14K (1.13 g, 4.2 mmol) was dissolved in 11 mL 25% aqueous acetic acid and heated to 60° C. Zinc dust (1.10 g) was then added in 4 equal portions at 30-minute intervals. After heating for a total of 3 hours, an aliquot was removed and checked by LC-MS, which indicated only a trace of unreacted starting material remaining, along with desired product. The mixture was cooled to room temperature, filtered and stripped in vacuo, leaving 2.31 g of a slushy white solid. The methyl ester was hydrolysed with dilute hot HCl to the title compound. After purification by reverse phase chromatography followed by lyophilization, 0.31 g of the title compound as a glassy solid was obtained.

Anal. Calcd. for C$_{10}$H$_{19}$N$_3$O$_2$.1.22 HCl.1.15 H$_2$O: C, 46.13; H, 8.15; N, 15.09; Cl, 15.53. Found: C, 46.38; H, 8.51; N, 15.13; Cl, 15.80. Mass spec: M+1=214

Example 16

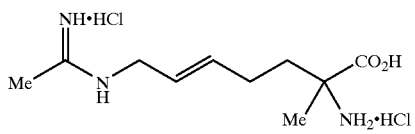

(2R/S,5E)-2-amino-2-methyl-7-[(1-iminoethyl)amino]-5-heptenoic acid, Dihydrochloride

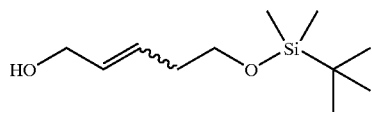

Example 16A

A sample of (E/Z)-5-t-butyldimethylsilyloxy-2-penten-1-ol was prepared from 5,5-dihydro-2-pyrone (Aldrich) by the method of Harold, Mohr and Tamm *Helvetica Chimica Acta* 66,2, 1983 744–754.

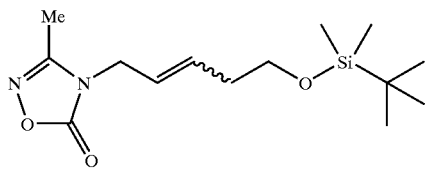

Example 16B

To a solution of the product of Example 16A (17.7 gm, 81.8 mmol) in THF (230 mL), at 0° C. was added Et$_3$N (12.4 gm, 122.7 mmol), followed by methanesulfonyl chloride (11.25 gm, 98.2 mmol), so that ΔT<+10° C. (~30 minutes). The reaction mixture was stirred for an additional 1 hour at 0° C. A 25 mL aliquot of saturated KHCO$_3$ was then added followed by 25 mL D1 H$_2$O. The layers were separated, and the organic was washed with 25 mL 5% citric acid solution followed by 25 mL brine. The organic layer was then dried over MGSO$_4$, filtered and then concentrated in vacuo to yield 23.3 gm (79.1 mmol) of a yellow oil. $^1$HNMR indicated the mesylated alcohol in a 2:1 ratio (E:Z). This oil was dissolved in DMF (225 mL) and to this solution was added the sodium salt of 3-methyl-1,2,4-oxadiazolin-5-one (17.7 gm, 118.6 mmol) and the mixture was stirred for 48 hr. The mixture was then concentrated and partitioned between EA and water. The organic layer was separated and then washed with brine, and dried over MGSO$_4$. The suspension was filtered and concentrated in vacuo to yield 23 gm of desired alkylated product (2:1, E:Z, by $^1$HNMR). This material was purified by column chromatography (5% IPA:Heptane) to yield 3 gram pure desired title E isomer by $^1$HNMR.

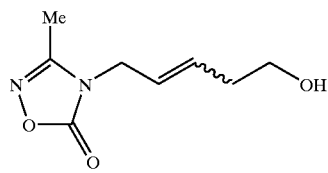

Example 16C

To a solution of the product of Example 16B (3 gm) in THF (6 mL), was added glacial acetic acid (6 mL) and 5 mL H$_2$O. The reaction was stirred at room temperature for 5 hr before being concentrated in vacuo to yield 2.25 g of the desired material as indicated by $^1$HNMR. The crude mixture was then carried on without purification.

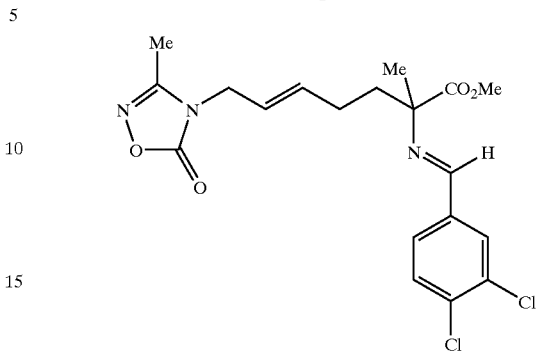

Example 16D

To a –10° C. solution of imidazole (1.49 gm, 21.96 mmol) and triphenyl phosphine (3.84 g, 14.65 mmol), in CH$_2$Cl$_2$ (25 mL) was added Iodine (3.71 g, 14.65 mmol). To this mixture was added, dropwise, a solution of Example 16C (2.25 g, 12.2 mmol) in CH$_2$Cl$_2$. This mixture was then stirred at room temperature for 5 hr. The crude mixture was poured onto a 5×10 cm bed of silica, and the product was eluted with 20% EA:Hexanes. The organics were then concentrated to yield 3.6 gm oily iodo derivative. Lithium Iodide (2.46 gm, 18.36 mmol) was then dissolved in DMF (30 mL) and cooled to –10° C. To this solution was added the product of Example 14H (4.8 g, 18.36 mmol), followed by the iodo compound (3.6 gm, 12.2 mmol). The BTTP (6.1 gm, 19.5 mmol) was then added dropwise. After stirring for 18 hr from –10° C. to room temperature, the reaction mixture was transferred to a separatory funnel and diluted with 120 mL of EA. The organic layer was washed with 80 ml of H$_2$O, dried over MgSO$_4$, filtered and CIV to yield 4.1 g of product. $^1$HNMR indicated that this was the desired compound that was used in the subsequent reaction.

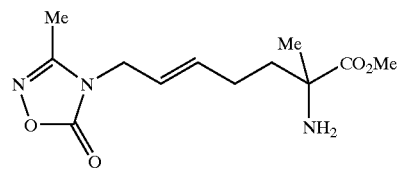

Example 16E

The product of Example 16D (4.1 g) was dissolved in 15 mL of EA. To this was added 50 mL of 1N HCl and the mixture was stirred at room temperature for 4.5 hrs. The reaction was transferred to seperatory funnel and the acidic layer was separated. The organic layer was washed with 15 mL 1N HCl and the combined aqueous layers were adjusted pH to ~7.5 with KHCO$_3$. The free base was isolated by washing aqueous layer 3 times with 50 mL of methylene chloride. This was dried over MgSO$_4$, filtered, and CIV to yield 3.2 g. The residue was purified via reverse phase HPLC to obtained 1 g of pure desired E title compound.

$^1$HNMR (CDCl$_3$) δ 1.33 (s, 3H), 1.6–1.7 (m, 1H), 1.75–1.85 (m, 1H), 1.95–2.2 (m, 2H), 2.25 (s, 3H), 3.7 (s, 3H), 4.12 (d, 2H, J=6Hz), 5.45–5.55 (m, 1H), 5.65–5.75 (m, 1H)

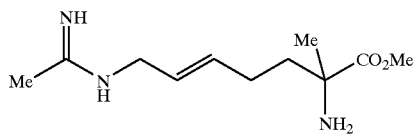

Example 16F

To a reaction tube was added 180 mg of the product of Example 16E in 10 mL methanol. To this solution was charged 360 mg of Lindlar catalyst (200 mol %) and 300 μL of formic acid. The tube was sealed and heated to 60° C. for 18 hrs. The reaction was allowed to cool and filtered through celite. To the filtrate was added 2 mL of 1N HCl and CIV to yield 150 mg of the title product. ¹HNMR indicates desired conversion to amidine. This material was carried into the next reaction without purification. ¹HNMR (D$_2$O) δ 1.5 (s, 3H), 1.85–2.05 (m, 3H), 2.1–2.2 (m, 1H), 2.15 (s, 3H), 3.7 (s, 3H), 3.9(d, 2H, J=6Hz), 5.55–5.65 (m, 1H), 5.70–5.80 (m, 1H).

Example 16

The product of Example 16F (100 mg) was dissolved in 10 mL 2N HCl and reluxed for 24 hrs. ¹HNMR of aliquot indicated complete hydrolysis. Therefore, CIV to yield 90 mg of crude amino acid. This material was purified on reversed phase HPLC to give 78 mg pure desired title E isomer.

¹HNMR (D$_2$O) δ 1.5 (s, 3H), 1.90–2.15 (m, 3H), 2.18–2.29 (m, 1H), 2.22 (s, 3H), 3.95(d, 2H, J=6Hz), 5.55–5.65 (m, 1H), 5.70–5.80 (m, 1H) Elemental analysis (for desired containing 2.3 mol HCl and 0.5 mol H20); C % (calc.) 39.23. (found) 39.21. H % (calc.) 7.34. (found) 7.51. N % (calc.) 13.73. (found) 13.48.

Scheme 13

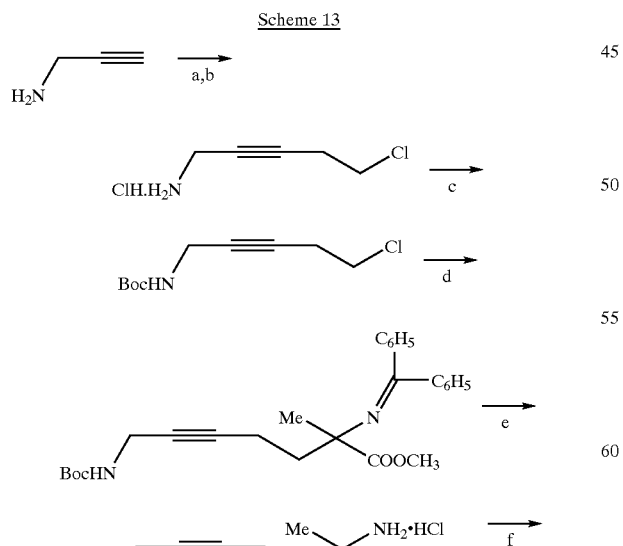

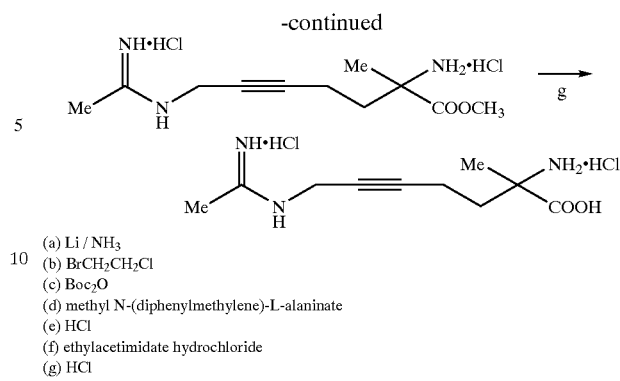

(a) Li / NH$_3$
(b) BrCH$_2$CH$_2$Cl
(c) Boc$_2$O
(d) methyl N-(diphenylmethylene)-L-alaninate
(e) HCl
(f) ethylacetimidate hydrochloride
(g) HCl

Example 17

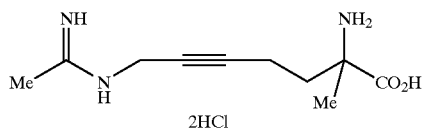

(2R/S)-2-amino-2-methyl-7-[(1-iminoethyl)amino]-5-heptynoic acid, Dihydrochloride

Example 18

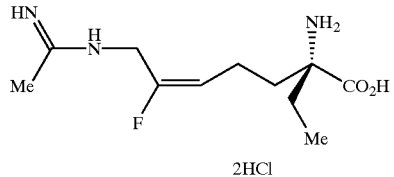

(2S,5E)-2-amino-2-ethyl-6-fluoro-7-[(1-iminoethyl)amino]-5-heptenoic acid, Dihydrochloride

Example 19

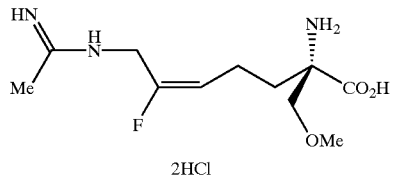

(2S,5E)-2-amino-2-methoxymethyl-6-fluoro-7-[(1-iminoethyl)amino]-5-heptenoic acid, Dihydrochloride

Example 20

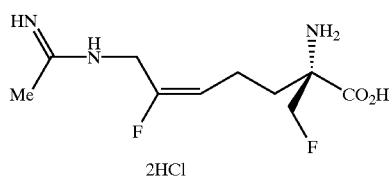

(2S,5E)-2-amino-2-fluoromethyl-6-fluoro-7-[(1-iminoethyl)amino]-5-heptenoic acid, Dihydrochloride

Example 21

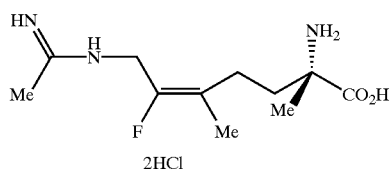

(2S,5E)-2-amino-2,5-dimethyl-6-fluoro-7-[(1-iminoethyl)amino]-5-heptenoic acid, Dihydrochloride

Example 22

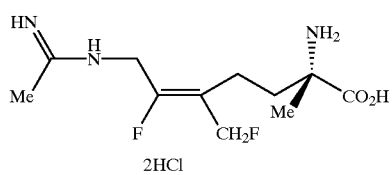

(2S,5Z)-2-amino-5-fluoromethyl-2-methyl-6-fluoro-7-[(1-iminoethyl)amino]-5-heptenoic acid, Dihydrochloride

Example 23

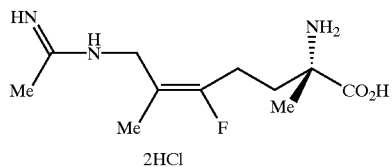

(2S,5E)-2-amino-2,6-dimethyl-5-fluoro-7-[(1-iminoethyl)amino]-5-heptenoic acid, Dihydrochloride

Example 24

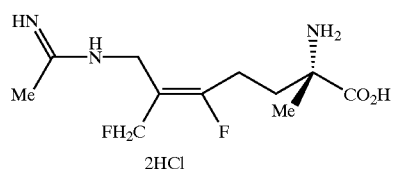

(2S,5Z)-2-amino-6-fluoromethyl-2-methyl-5-fluoro-7-[(1-iminoethyl)amino]-5-heptenoic acid, Dihydrochloride

Example 25

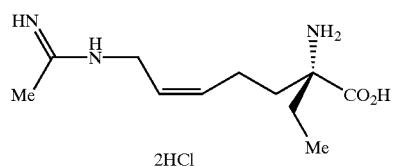

(2S,5Z)-2-amino-2-ethyl-7-[(1-iminoethyl)amino]-5-heptenoic acid, Dihydrochloride

Example 26

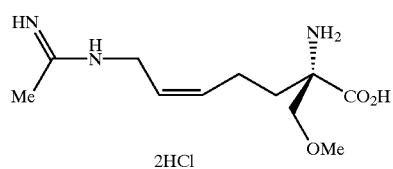

(2S,5Z)-2-amino-2-methoxymethyl-7-[(1-iminoethyl)amino]-5-heptenoic acid, Dihydrochloride

Example 27

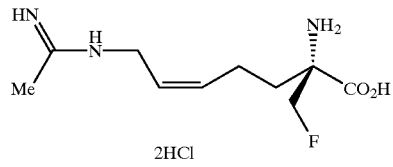

(2S,5Z)-2-amino-2-fluoromethyl-7-[(1-iminoethyl)amino]-5-heptenoic acid, Dihydrochloride

Example 28

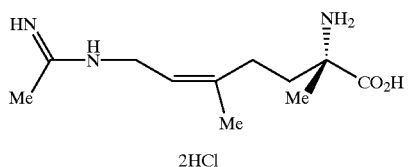

(2S,5Z)-2-amino-2,5-dimethyl-7-[(1-iminoethyl)amino]-5-heptenoic acid, Dihydrochloride

Example 29

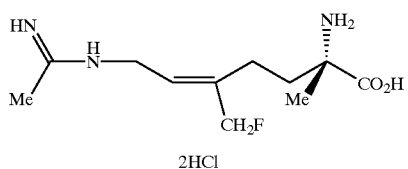

(2S,5E)-2-amino-5-fluoromethyl-2-methyl-7-[(1-iminoethyl)amino]-5-heptenoic acid, Dihydrochloride

Example 30

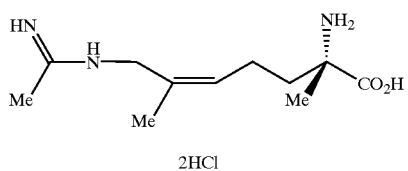

(2S,5Z)-2-amino-2,6-dimethyl-7-[(1-iminoethyl)amino]-5-heptenoic acid, Dihydrochloride

Example 31

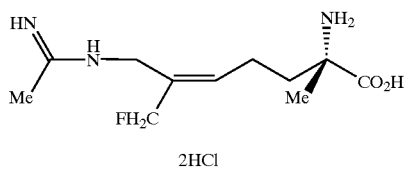

(2S,5E)-2-amino-6-fluoromethyl-2-methyl-7-[(1-iminoethyl)amino]-5-heptenoic acid, Dihydrochloride

Example 32

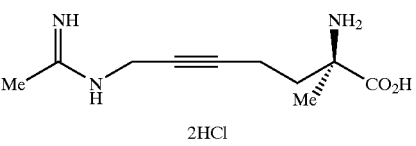

(2S)-2-amino-2-methyl-7-[(1-iminoethyl)amino]-5-heptynoic acid, Dihydrochloride

Novel Intermediates

Novel intermediates useful in synthesizing compounds of the present invention include:

4-[(2E)-5-[[(1,1-dimethylethyl)dimethylsilyl]oxy]-2-fluoro-2-pentenyl]-3-methyl-1,2,4-oxadiazol-5(4H)-one;

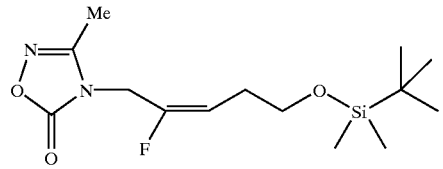

4-[(2E)-2-fluoro-5-hydroxy-2-pentenyl]-3-methyl-1,2,4-oxadiazol-5(4H)-one;

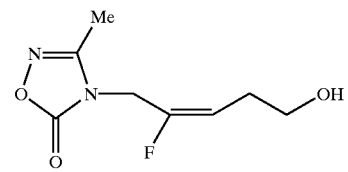

4-[(2E)-2-fluoro-5-iodo-2-pentenyl]-3-methyl-1,2,4-oxadiazol-5(4H)-one;

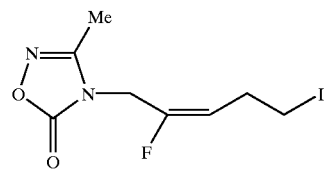

(3S,6R)-3-[(3E)-4-fluoro-5-(3-methyl-5-oxo-1,2,4-oxadiazol-4(5H)-yl)-3-pentenyl]-3,6-dihydro-3-methyl-6-(1-methylethyl)-5-phenyl-2H-1,4-oxazin-2-one;

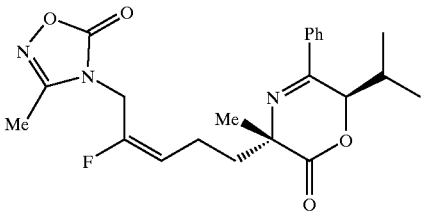

N-[(2E)-5-[(3S,6R)-3,6-dihydro-3-methyl-6-(1-methylethyl)-2-oxo-5-phenyl-2H-1,4-oxazin-3-yl]-2-fluoro-2-pentenyl]ethanimidamide;

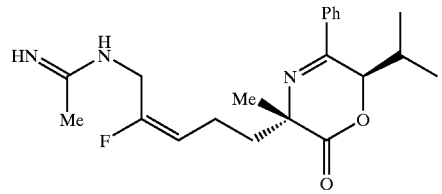

(5E)-2-amino-6-fluoro-2-methyl-7-(3-methyl-5-oxo-1,2,4-oxadiazol-4(5H)-yl)-5-heptenoic acid, methyl ester;

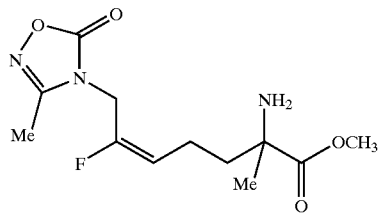

(2S,5E)-2-amino-6-fluoro-2-methyl-7-(3-methyl-5-oxo-1,2,4-oxadiazol-4(5H)-yl)-5-heptenoic acid, methyl ester;

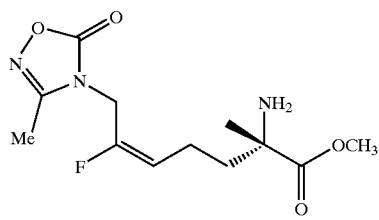

(2S,5E)-2-amino-6-fluoro-7-[[(1E)-1-(hydroxyimino)ethyl]amino]-2-methyl-5-heptenoic acid;

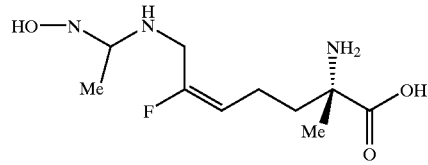

(2S,5E)-2-amino-6-fluoro-7-[(1-iminoethyl)amino]-2-methyl-5-heptenoic acid, methyl ester;

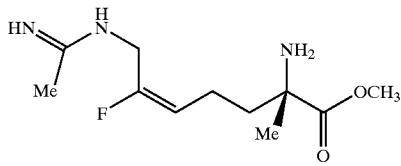

(2R,5E)-2-amino-6-fluoro-2-methyl-7-(3-methyl-5-oxo-1,2,4-oxadiazol-4(5H)-yl)-5-heptenoic acid, methyl ester;

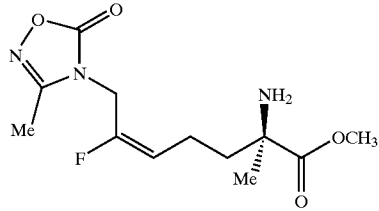

(2R,5E)-2-amino-6-fluoro-7-[(1-iminoethyl)amino]-2-methyl-5-heptenoic acid, ethyl ester;

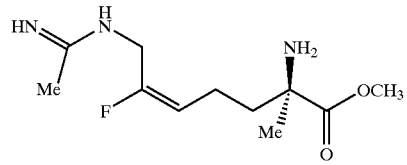

(5E)-2-amino-6-fluoro-7-(3-methyl-5-oxo-1,2,4-oxadiazol-4(5H)-yl)-5-heptenoic acid, methyl ester;

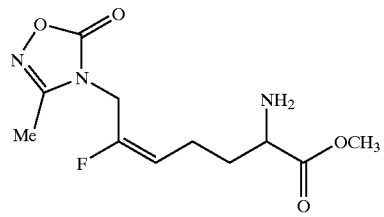

(5E)-2-[[(1Z)-(4-chlorophenyl)methylidene]amino]-6-fluoro-7-(3-methyl-5-oxo-1,2,4-oxadiazol-4(5H)-yl)-5-heptenoic acid, methyl ester;

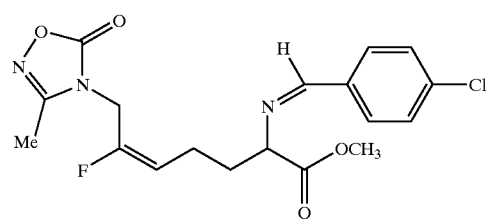

(5E)-2-amino-6-fluoro-2-methyl-7-(3-methyl-5-oxo-1,2,4-oxadiazol-4(5H)-yl)-5-heptenoic acid, methyl ester;

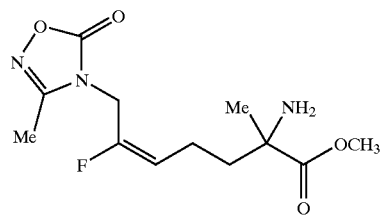

(5E)-2-amino-6-fluoro-7-[(1-iminoethyl)amino]-2-methyl-5-heptenoic acid, methyl ester;

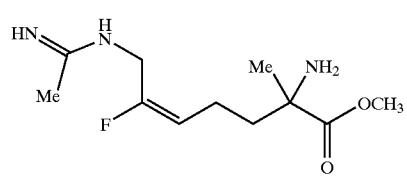

Methyl (5E)-7-[(tert-butoxycarbonyl)amino]-2-{[(1Z)-(2,4-dichlorophenyl)methylidene]amino}-5-fluoro-2-methylhept-5-enoate;

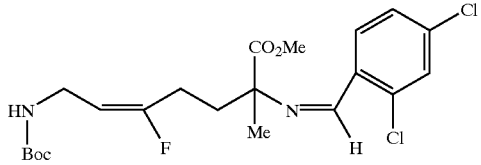

(5E)-2,7-diamino-5-fluoro-2-methyl-5-heptenoic acid, methyl ester, dihydrochloride;

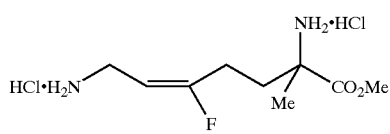

(5E)-2-amino-5-fluoro-7-[(1-iminoethyl)amino]-2-methyl-5-heptenoic acid, methyl ester, monohydrochloride;

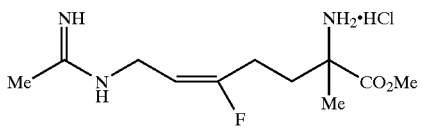

(5Z)-2-[[(1E)-(2,4-dichlorophenyl)methylidene]amino]-7-[[(1,1-dimethylethoxy)carbonyl]amino]-5-fluoro-2-methyl-5-heptenoic acid, methyl ester;

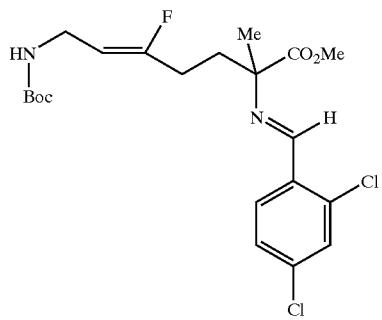

(5Z)-2,7-diamino-5-fluoro-2-methyl-5-heptenoic acid, methyl ester, dihydrochloride;

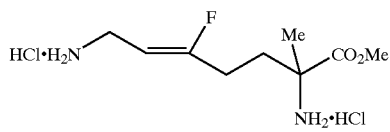

(5Z)-2-amino-5-fluoro-7-[(1-iminoethyl)amino]-2-methyl-5-heptenoic acid, methyl ester, dihydrochloride;

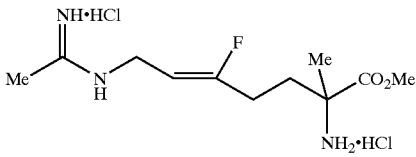

4-[(2Z)-5-hydroxy-2-pentenyl]-3-methyl-1,2,4-oxadiazol-5(4H)-one;

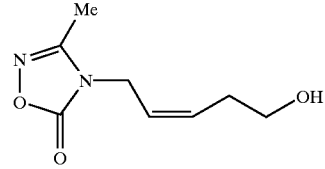

(3Z)-5-(3-methyl-5-oxo-1,2,4-oxadiazol-4(5H)-yl)-3-pentenyl ester, acetic acid, trifluoro-;

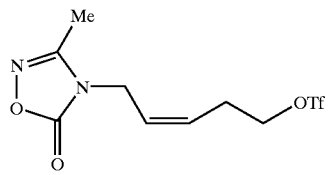

4-[(2Z)-5-[(2R,4S)-3-benzoyl-2-(1,1-dimethylethyl)-4-methyl-5-oxo-4-oxazolidinyl]-2-pentenyl]-3-methyl-1,2,4-oxadiazol-5(4H)-one;

3-Methyl-4-]5-(tetrahydro-pyran-2-yloxy)-pent-2-enyl]-4H-[1,2,4]oxadiazol-5-one;

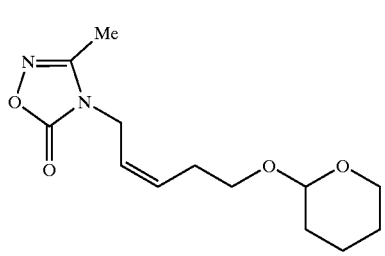

4-(5-Hydroxy-pent-2-enyl)-3-methyl-4H-[1,2,4]oxadiazol-5-one;

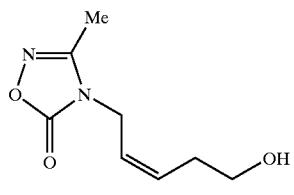

Methanesulfonic acid 5-(3-methyl-5-oxo-[1,2,4]oxadiazol-4-yl)-pent-3-enyl ester;

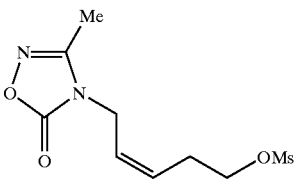

4-(5-Iodo-pent-2-enyl)-3-methyl-4H-[1,2,4]oxadiazol-5-one;

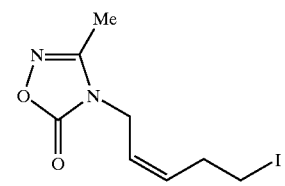

Rac-2-Amino-2-methyl-7-(3-methyl-5-oxo-[1,2,4]oxadiazol-4-yl)-hept-5-enoic acid methyl ester;

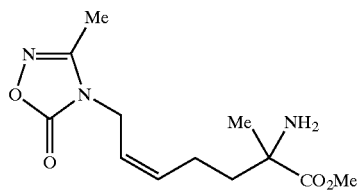

Rac-2-Amino-2-methyl-7-(3-methyl-5-oxo-[1,2,4]oxadiazol-4-yl)-hept-5-enoic acid;

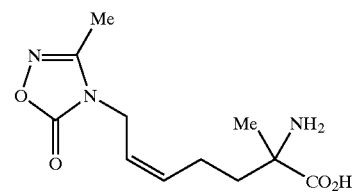

(2S,5Z)-2-Amino-2-methyl-7-(3-methyl-5-oxo-[1,2,4]oxadiazol-4-yl)-hept-5-enoic acid methyl ester;

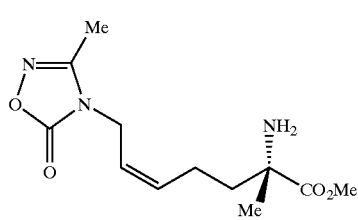

(2S,5Z)-7-Acetimidoylamino-2-amino-2-methyl-hept-5-enoic acid methyl ester, dihydrochloride hydrate;

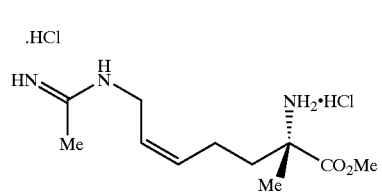

(2S,5Z)-2-amino-7-[[(1E)-1-(hydroxyimino)ethyl]amino]-2-methyl-5-heptenoic acid;

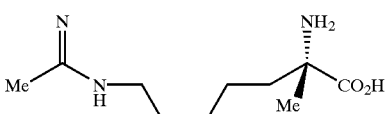

4-[(2E)-5-[[(1,1-dimethylethyl)dimethylsilyl]oxy]-2-pentenyl]-3-methyl-1,2,4-oxadiazol-5(4H)-one;

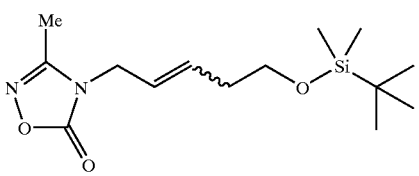

4-[(2E)-5-hydroxy-2-pentenyl]-3-methyl-2,4-oxadiazol-5(4H)-one;

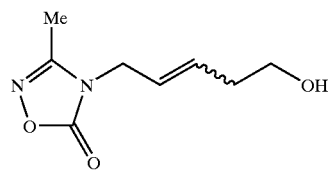

(5E)-2-[[(1E)-(3,4-dichlorophenyl)methylidene]amino]-2-methyl-7-(3-methyl-5-oxo-1,2,4-oxadiazol-4(5H)-yl)-5-heptenoic acid, methyl ester;

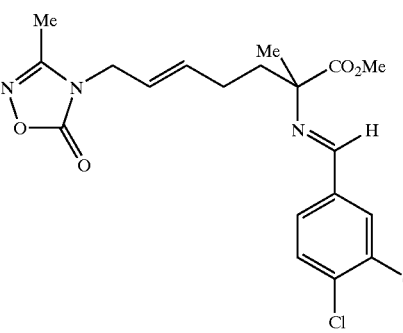

(5E)-2-amino-2-methyl-7-(3-methyl-5-oxo-1,2,4-oxadiazol-4(5H)-yl)-5-heptenoic acid, methyl ester; and

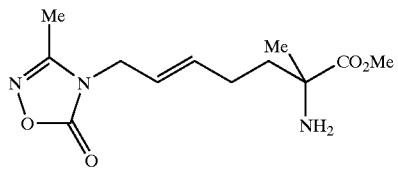

Methyl (5E)-2-amino-7-(ethanimidoylamino)-2-methylhept-5-enoate.

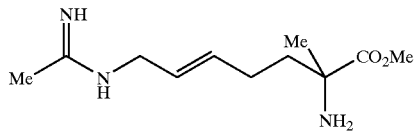

Biological Data

Some or all of the following assays are used to demonstrate the nitric oxide synthase inhibitory activity of the invention's compounds as well as demonstrate the useful pharmacological properties.

Citrulline Assay for Nitric Oxide Synthase

Nitric oxide synthase (NOS) activity can be measured by monitoring the conversion of L-[2,3-$^3$H]-arginine to L-[2,3-$^3$H]-citrulline (Bredt and Snyder, *Proc. Natl. Acad. Sci. U.S.A.*, 87, 682–685, 1990 and Moore et al, *J. Med. Chem.*, 39, 669–672, 1996). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a λcDNA library made from RNA extracted from a colon sample from a patient with ulcerative colitis. The cDNA for human endothelial constitutive NOS (hecNOS) is isolated from a λcDNA library made from RNA extracted from human umbilical vein endothelial cells (HUVEC) and the cDNA for human neuronal constitutive NOS (hncNOS) is isolated from a λcDNA library made from RNA extracted from human cerebellum obtained from a cadaver. The recombinant enzymes are expressed in Sf9 insect cells using a baculovirus vector (Rodi et al, in *The Biology of Nitric Oxide, Pt. 4: Enzymology, Biochemistry and Immunology*; Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 µL of enzyme is added to 40 µL of 50 mM Tris (pH 7.6) in the presence or absence of test compounds and the reaction initiated by the addition of 50 µL of a reaction mixture containing 50 mM Tris (pH 7.6), 2.0 mg/mL bovine serum albumin, 2.0 mM DTT, 4.0 mM CaCl$_2$, 20 µM FAD, 100 µM tetrahydrobiopterin, 0.4 mM NADPH and 60 µM L-arginine containing 0.9 µCi of L-[2,3-$^3$H]-arginine. The final concentration of L-arginine in the assay is 30 µM. For hecNOS or hncNOS, calmodulin is included at a final concentration of 40–100 nM. Following incubation at 37° C. for 15 minutes, the reaction is terminated by addition of 400 µL of a suspension (1 part resin, 3 parts buffer) of Dowex 50 W X-8 cation exchange resin (sodium form) in a stop buffer containing 10 mM EGTA, 100 mM HEPES, pH 5.5 and 1 mM L-citrulline. After mixing the resin is allowed to settle and L-[2,3-$^3$H]-Citrulline formation is determined by counting aliquots of the supernatant with a liquid scintillation counter. IC$_{50}$ values can be determined by testing each compound at several concentrations. Results are reported in Table I as the IC$_{50}$ values of compounds for hiNOS, hecNOS and hncNOS.

TABLE I

| Example Number | IC$_{50}$ [µM] | | |
|---|---|---|---|
| | hiNOS | hecNOS | hncNOS |
| 1 | 0.4 | 37 | 7.6 |
| 3 | 56 | 352 | 584 |
| 4 | 0.57 | 52 | 13 |
| 14 | 0.7 | 31 | 12 |
| 15 | 121 | 1930 | 1480 |

In Vivo Assay

Rats can be treated with an intraperitoneal injection of 1–12.5 mg/kg of endotoxin (LPS) to induce systemic expression of inducible nitric oxide synthase, resulting in markedly elevated plasma nitrite/nitrate levels. Compounds are administered orally 0.5–1 hours prior to LPS administration and plasma nitrite/nitrate levels are determined 5 hours following LPS administration. The results can be used to show that the administration of the nitric oxide synthase inhibitors decreases the rise in plasma nitrite/nitrate levels, a reliable indicator of the production of nitric oxide induced by endotoxin. ED$_{50}$ values (mg/kg) for inhibition of the LPS-induced increase in plasma nitrite/nitrate levels are shown in Table II.

TABLE II

ED$_{50}$'s for Examples determined in endotoxin-treated rats
All compounds administered orally unless otherwise noted.

| | |
|---|---|
| 1 | 0.4 |
| 4 | 0.3 |
| 14 | 0.3 |

Raw Cell Nitrite Assay

RAW 264.7 cells can be plated to confluency on a 96-well tissue culture plate grown overnight (17 h) in the presence of LPS to induce NOS. A row of 3–6 wells can be left untreated and serve as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 µL of buffer containing L-arginine (30 µM)+/−inhibitors for 1 h. The assay can be initiated by warming the plate to 37° C. in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite (T. P. Misko et al, *Analytical Biochemistry*, 214, 11–16, 1993).

Human cartilage explant assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 15–45 mg in weight and one or two explants per well are placed into either 96 or 48 well culture plates with 200–500 µL of culture media per well. The culture media was either a custom modification of Minimum Essential Medium(Eagle) with Earle's salts (GibcoBRL) prepared without L-Arginine, without L-Glutamine and without phenol red or a custom modification of serumless Neuman and Tytell (GibcoBRL) medium prepared without L-arginine, without insulin, without ascorbic acid, without L-glutamine and without phenol red. Both are supplemented before use with 100 μM L-Arginine (Sigma), 2 mM L-glutamine, 1× HL-1 supplement (BioWhittaker), 50 mg/ml ascorbic acid (Sigma) and 150 pg/ml recombinant human IL-1β (RD Systems) to induce nitric oxide synthase. Compounds are then added in 10 μL aliquots and the explants incubated at 37° C. with 5% $CO_2$ for 18–24 hours.

The day old supernatant is then discarded and replaced with fresh culture media containing recombinant human IL-1β and compound and incubated for another 20–24 hours. This supernatant is analyzed for nitrite with a fluorometric assay (Misko et al, *Anal. Biochem.*, 214, 11–16, 1993). All samples are done in quadruplicate. Unstimulated controls are cultured in media in the absence of recombinant human IL-1β. $IC_{50}$ values (Table III) are determined from plotting the percent inhibition of nitrite production at six different concentrations of inhibitor.

TABLE III

| Example No. | $IC_{50}$ [μM] |
|---|---|
| 1 | 0.4 |
| 14 | 0.8 |

Assay for Time Dependent Inhibition

Compounds are evaluated for time dependent inhibition of human NOS isoforms by preincubation of the compound with the enzyme at 37° C. in the presence of the citrulline enzyme assay components, minus L-arginine, for times ranging from 0–60 minutes. Aliquots (10 μL) are removed at 0, 10, 21 and 60 minutes and immediately added to a citrulline assay enzyme reaction mixture containing L-[2,3-$^3$H]-arginine and a final L-arginine concentration of 30 μM in a final volume of 100 μL. The reaction is allowed to proceed for 15 minutes at 37° C. and terminated by addition of a suspension of Dowex 50W X-8 cation exchange resin as described above for the citrulline NOS assay. The % inhibition of NOS activity by an inhibitor is taken as the per cent inhibition in activity compared to control enzyme preincubated for the same time in the absence of inhibitor. Time-dependent inhibition can be demonstrated as an increase in inhibition with increasing preincubation time.

What is claimed:

1. A compound of Formula I:

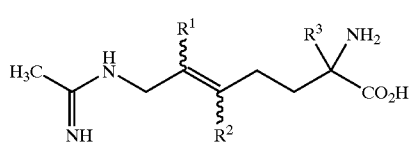

or a pharmaceutically acceptable salt thereof, wherein:
   $R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
   $R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
   $R^3$ is $C_1$–$C_5$ alkyl, said $C_1$–$C_5$ alkyl optionally substituted by halo or alkoxy, said alkoxy optionally substituted by one or more halo.

2. The compound of claim 1 wherein the compound is the Z isomer.

3. The compound of claim 2 wherein:
   $R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
   $R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
   $R^3$ is $C_1$–$C_5$ alkyl, said $C_1$–$C_5$ alkyl optionally substituted by halo or alkoxy.

4. The compound of claim 3 wherein:
   $R^1$ is selected from the group consisting of hydrogen, halo, and $C_1$–$C_3$ alkyl;
   $R^2$ is selected from the group consisting of hydrogen, halo and $C_1$–$C_3$ alkyl; and
   $R^3$ is $C_1$–$C_5$ alkyl, said $C_1$–$C_5$ alkyl optionally substituted by halo or alkoxy.

5. The compound of claim 3 wherein:
   $R^1$ is selected from the group consisting of hydrogen, halo, and $C_1$–$C_3$ alkyl; said $C_1$–$C_5$ alkyl optionally substituted by halo or alkoxy, said alkoxy optionally substituted by one or more halo;
   $R^2$ is selected from the group consisting of hydrogen, halo and $C_1$–$C_5$ alkyl; and
   $R^3$ is $C_1$–$C_5$ alkyl, said $C_1$–$C_5$ alkyl optionally substituted by fluorine or alkoxy.

6. The compound of claim 3 wherein:
   $R^1$ is selected from the group consisting of hydrogen, halo, and $C_1$–$C_3$ alkyl;
   $R^2$ is selected from the group consisting of hydrogen, halo and $C_1$–$C_3$ alkyl; and
   $R^3$ is $C_1$–$C_3$ alkyl optionally substituted by fluorine.

7. The compound of claim 3 wherein:
   $R^1$ is selected from the group consisting of hydrogen, halo, and $C_1$–$C_3$ alkyl;
   $R^2$ is selected from the group consisting of hydrogen, halo and $C_1$–$C_3$ alkyl; and
   $R^3$ is $C_1$–$C_3$ alkyl.

8. The compound of claim 3 wherein:
   $R^1$ is hydrogen;
   $R^2$ is selected from the group consisting of hydrogen, halo and $C_1$–$C_3$ alkyl; and
   $R^3$ is $C_1$–$C_3$ alkyl.

9. The compound of claim 8 wherein:
   $R^1$ is hydrogen;
   $R^2$ is selected from the group consisting of hydrogen and halo; and
   $R^3$ is $C_1$–$C_3$ alkyl.

10. The compound of claim 9 wherein:
   $R^1$ is hydrogen;
   $R^2$ is selected from the group consisting of hydrogen and fluorine; and
   $R^3$ is $C_1$–$C_3$ alkyl.

11. The compound of claim 10 wherein:
   $R^1$ is hydrogen;
   $R^2$ is selected from the group consisting of hydrogen and fluorine; and
   $R^3$ is methyl.

12. The compound of claim 11 wherein:
$R^1$ is hydrogen;
$R^2$ is hydrogen; and
$R^3$ is methyl.
13. The compound of claim 2 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted alkoxy or one or more halo.
14. A compound of Formula III

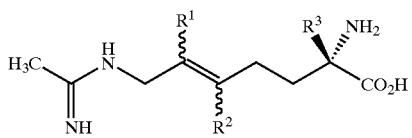

or a pharmaceutically acceptable salt thereof, wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy, said alkoxy optionally substituted by one or more halo.
15. The compound of claim 14 wherein the compound is the Z isomer.
16. The compound of claim 15 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by one or more halo or alkoxy.
17. The compound of claim 15 wherein:
$R^1$ is selected from the group consisting of hydrogen, halo, and $C_1$–$C_3$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.
18. The compound of claim 17 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine or alkoxy.
19. The compound of claim 17 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by fluorine.
20. The compound of claim 16 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.
21. The compound of claim 16 wherein:
$R^1$ is hydrogen;
$R^2$ is selected from the group consisting of hydrogen, halo and $C_1$–$C_3$ alkyl; and
$R^3$ is $C_1$–$C_3$ alkyl.
22. The compound of claim 21 wherein:
$R^1$ is hydrogen;
$R^2$ is selected from the group consisting of hydrogen and halo; and
$R^3$ is $C_1$–$C_3$ alkyl.
23. The compound of claim 22 wherein:
$R^1$ is hydrogen;
$R^2$ is selected from the group consisting of hydrogen and fluorine; and
$R^3$ is $C_1$–$C_3$ alkyl.
24. The compound of claim 23 wherein:
$R^1$ is hydrogen;
$R^2$ is selected from the group consisting of hydrogen and fluorine; and
$R^3$ is methyl.
25. The compound of claim 24 wherein:
$R^1$ is hydrogen;
$R^2$ is hydrogen; and
$R^3$ is methyl.
26. The compound of claim 15 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted by alkoxy or one or more halo.
27. A compound selected from the group consisting of:
(2S,5E)-2-amino-2-methyl-6-fluoro-7-[(1-iminoethyl)amino]-5-heptenoic acid;
(2R,5E)-2-amino-2-methyl-6-fluoro-7-[(1-iminoethyl)amino]-5-heptenoic acid;
(2R/S,5E)-2-amino-2-methyl-6-fluoro-7-[(1-iminoethyl)amino]-5-heptenoic acid;
(2R/S,5E)-2-amino-2-methyl-5-fluoro-7-[(1-iminoethyl)amino]-5-heptenoic acid;
(2R/S,5Z)-2-amino-2-methyl-5-fluoro-7-[(1-iminoethyl)amino]-5-heptenoic acid;
(2R,5E)-2-amino-2-methyl-5-fluoro-7-[(1-iminoethyl)amino]-5-heptenoic acid;
(2S,5E)-2-amino-2-methyl-5-fluoro-7-[(1-iminoethyl)amino]-5-heptenoic acid;

(2S,5Z)-2-amino-2-methyl-5,6-difluoro-7-[(1-iminoethyl)amino]-5-heptenoic acid;
(2R,5Z)-2-amino-2-methyl-5,6-difluoro-7-[(1-iminoethyl)amino]-5-heptenoic acid;
(2R/S,5Z)-2-amino-2-methyl-5,6-difluoro-7-[(1-iminoethyl)amino]-5-heptenoic acid;
(2S,5Z)-2-amino-2-methyl-6-fluoro-7-[(1-iminoethyl)amino]-5-heptenoic acid;
(2S,5Z)-2-amino-2-methyl-7-[(1-iminoethyl)amino]-5-heptenoic acid;
(2S,5Z)-2-amino-2-methyl-7-[(1-iminoethyl)amino]-5-heptenoic acid;
(2R,5Z)-2-amino-2-methyl-7-[(1-iminoethyl)amino]-5-heptenoic acid;
(2S,5E)-2-amino-2-ethyl-6-fluoro-7-[(1-iminoethyl)amino]-5-heptenoic acid;
(2S,5E)-2-amino-2-methoxymethyl-6-fluoro-7-[(1-iminoethyl)amino]-5-heptenoic acid;
(2S,5E)-2-amino-2-fluoromethyl-6-fluoro-7-[(1-iminoethyl)amino]-5-heptenoic acid;
(2S,5E)-2-amino-2,5-dimethyl-6-fluoro-7-[(1-iminoethyl)amino]-5-heptenoic acid;
(2S,5Z)-2-amino-5-fluoromethyl-2-methyl-6-fluoro-7-[(1-iminoethyl)amino]-5-heptenoic acid;
(2S,5E)-2-amino-2,6-dimethyl-5-fluoro-7-[(1-iminoethyl)amino]-5-heptenoic acid;
(2S,5Z)-2-amino-6-fluoromethyl-2-methyl-5-fluoro-7-[(1-iminoethyl)amino]-5-heptenoic acid;
(2S,5Z)-2-amino-2-ethyl-7-[(1-iminoethyl)amino]-5-heptenoic acid;
(2S,5Z)-2-amino-2-methoxymethyl-7-[(1-iminoethyl)amino]-5-heptenoic acid;
(2S,5Z)-2-amino-2-fluoromethyl-7-[(1-iminoethyl)amino]-5-heptenoic acid;
(2S,5Z)-2-amino-2,5-dimethyl-7-[(1-iminoethyl)amino]-5-heptenoic acid;
(2S,5E)-2-amino-5-fluoromethyl-2-methyl-7-[(1-iminoethyl)amino]-5-heptenoic acid;
(2S,5Z)-2-amino-2,6-dimethyl-7-[(1-iminoethyl)amino]-5-heptenoic acid;
(2S,5E)-2-amino-6-fluoromethyl-2-methyl-7-[(1-iminoethyl)amino]-5-heptenoic acid;
(2S,5E)-2-amino-2-methyl-6-fluoro-7-[(1-iminoethyl)amino]-5-heptenoic acid, dihydrochloride;
(2R,5E)-2-amino-2-methyl-6-fluoro-7-[(1-iminoethyl)amino]-5-heptenoic acid, dihydrochloride;
(2R/S,5E)-2-amino-2-methyl-6-fluoro-7-[(1-iminoethyl)amino]-5-heptenoic acid, dihydrochloride;
(2R/S,5E)-2-amino-2-methyl-5-fluoro-7-[(1-iminoethyl)amino]-5-heptenoic acid, dihydrochloride;
(2R¹S,5Z)-2-amino-2-methyl-5-fluoro-7-[(1-iminoethyl)amino]-5-heptenoic acid, dihydrochloride;
(2R, 5E)-2-amino-2-methyl-5-fluoro-7-[(1-iminoethyl)amino]-5-heptenoic acid, dihydrochloride;
(2S,5E)-2-amino-2-methyl-5-fluoro-7-[(1-iminoethyl)amino]-5-heptenoic acid, dihydrochloride;
(2S,5Z)-2-amino-2-methyl-5,6-difluoro-7-[(1-iminoethyl)amino]-5-heptenoic acid, dihydrochloride;
(2R,5Z)-2-amino-2-methyl-5,6-difluoro-7-[(1-iminoethyl)amino]-5-heptenoic acid, dihydrochloride;
(2R/S,5Z)-2-amino-2-methyl-5,6-difluoro-7-[(1-iminoethyl)amino]-5-heptenoic acid, dihydrochloride;
(2S,5Z)-2-amino-2-methyl-6-fluoro-7-[(1-iminoethyl)amino]-5-heptenoic acid, dihydrochloride;
(2S,5Z)-2-amino-2-methyl-7-[(1-iminoethyl)amino]-5-heptenoic acid, dihydrochloride;
(2R,5Z)-2-amino-2-methyl-7-[(1-iminoethyl)amino]-5-heptenoic acid, dihydrochloride;
(2R/S,5E)-2-amino-2-methyl-7-[(1-iminoethyl)amino]-5-heptenoic acid, dihydrochloride;
(2S,5E)-2-amino-2-ethyl-6-fluoro-7-[(1-iminoethyl)amino]-5-heptenoic acid, dihydrochloride;
(2S,5E)-2-amino-2-methoxymethyl-6-fluoro-7-[(1-iminoethyl)amino]-5-heptenoic acid, dihydrochloride;
(2S,5E)-2-amino-2-fluoromethyl-6-fluoro-7-[(1-iminoethyl)amino]-5-heptenoic acid, dihydrochloride;
(2S,5E)-2-amino-2,5-dimethyl-6-fluoro-7-[(1-iminoethyl)amino]-5-heptenoic acid, dihydrochloride;
(2S,5Z)-2-amino-5-fluoromethyl-2-methyl-6-fluoro-7-[(1-iminoethyl)amino]-5-heptenoic acid, dihydrochloride;
(2S,5E)-2-amino-2,6-dimethyl-5-fluoro-7-[(1-iminoethyl)amino]-5-heptenoic acid, dihydrochloride;
(2S,5Z)-2-amino-6-fluoromethyl-2-methyl-5-fluoro-7-[(1-iminoethyl)amino]-5-heptenoic acid, dihydrochloride;
(2S,5Z)-2-amino-2-ethyl-7-[(1-iminoethyl)amino]-5-heptenoic acid, dihydrochloride;
(2S,5Z)-2-amino-2-methoxymethyl-7-[(1-iminoethyl)amino]-5-heptenoic acid, dihydrochloride;
(2S,5Z)-2-amino-2-fluoromethyl-7-[(1-iminoethyl)amino]-5-heptenoic acid, dihydrochloride;
(2S,5Z)-2-amino-2,5-dimethyl-7-[(1-iminoethyl)amino]-5-heptenoic acid, dihydrochloride;
(2S,5E)-2-amino-5-fluoromethyl-2-methyl-7-[(1-iminoethyl)amino]-5-heptenoic acid, dihydrochloride;
(2S,5Z)-2-amino-2,6-dimethyl-7-[(1-iminoethyl)amino]-5-heptenoic acid, dihydrochloride;
(2S,5E)-2-amino-6-fluoromethyl-2-methyl-7-[(1-iminoethyl)amino]-5-heptenoic acid, dihydrochloride; and 28. (2S,5Z)-2-amino-7-(ethanimidoylamino)-2-methylhept-5-enoic acid, or a pharmaceutically acceptable salt thereof.

29. A pharmaceutical composition comprising (2S,5Z)-2-amino-7-(ethanimidoylamino)-2-methylhept-5-enoic acid, or a pharmaceutically acceptable salt thereof, together with a pharmaceutically acceptable carrier.

30. The compound of claim 1 wherein:
$R^1$ is hydrogen;
$R^2$ is fluorine; and
$R^3$ is methyl.

31. The compound of claim 3 wherein:
$R^1$ is halo;
$R^2$ is selected from the group consisting of hydrogen, halo and $C_1$–$C_3$ alkyl; and
$R^3$ is $C_1$–$C_3$ alkyl.

32. The compound of claim 31 wherein:
$R^1$ is halo;
$R^2$ is halo; and
$R^3$ is $C_1$–$C_3$ alkyl.

33. The compound of claim 32 wherein:
$R^1$ is fluorine;
$R^2$ is fluorine; and
$R^3$ is methyl.
34. The compound of claim 31 wherein:
$R^1$ is fluorine;
$R^2$ is selected from the group consisting of hydrogen and $C_1$–$C_3$ alkyl; and
$R^3$ is methyl.
35. The compound of clam 34 wherein:
$R^1$ is fluorine;
$R^2$ is hydrogen; and
$R^2$ is methyl.
36. The compound of claim 3 wherein:
$R^1$ is methyl;
$R^2$ is hydrogen; and
$R^3$ is methyl.
37. The compound of claim 3 wherein:
$R^1$ is hydrogen;
$R^2$ is methyl; and
$R^3$ is methyl.
38. The compound of claim 3 wherein:
$R^1$ is methyl;
$R^2$ is methyl; and
$R^3$ is methyl.
39. The compound of claim 13 wherein:
$R^1$ is selected from the group consisting of hydrogen and fluorine;
$R^2$ is $C_1$–$C_3$ alkyl substituted by one or more halo; and
$R^3$ is methyl.
40. The compound of claim 39 wherein:
$R^1$ is hydrogen;
$R^2$ is $CH_2F$; and
$R^3$ is methyl.
41. The compound of claim 13 wherein:
$R^1$ is $CH_2F$;
$R^2$ is hydrogen; and
$R^3$ is methyl.
42. The compound of claim 13 wherein:
$R^1$ is hydrogen;
$R^2$ is hydrogen; and
$R^3$ is $CH_2F$.
43. The compound of claim 13 wherein:
$R^1$ is hydrogen;
$R^2$ is methoxymethyl; and
$R^3$ is methyl.
44. The compound of claim 13 wherein:
$R^1$ is methoxymethyl;
$R^2$ is hydrogen; and
$R^3$ is methyl.
45. The compound of claim 13 wherein:
$R^1$ is hydrogen;
$R^2$ is hydrogen; and
$R^3$ is methoxymethyl.
46. The compound of claim 1 wherein the compound is the E isomer.
47. The compound of claim 46 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by one or more halo or alkoxy.
48. The compound of claim 47 wherein:
$R^1$ is selected from the group consisting of hydrogen, halo, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.
49. The compound of claim 48 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.
50. The compound of claim 48 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by fluorine or alkoxy.
51. The compound of claim 50 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.
52. The compound of claim 47 wherein:
$R^1$ is hydrogen;
$R^2$ is selected from the group consisting of hydrogen, halo and $C_1$–$C_3$ alkyl; and
$R^3$ is $C_1$–$C_3$ alkyl.
53. The compound of claim 52 wherein:
$R^1$ is hydrogen;
$R^2$ is selected from the group consisting of hydrogen and halo; and
$R^3$ is $C_1$–$C_3$ alkyl.
54. The compound of claim 53 wherein:
$R^1$ is hydrogen;
$R^2$ is selected from the group consisting of hydrogen and fluorine; and
$R^3$ is $C_1$–$C_3$ alkyl.
55. The compound of claim 54 wherein:
$R^1$ is hydrogen;
$R^2$ is selected from the group consisting of hydrogen and fluorine; and
$R^3$ is methyl.
56. The compound of claim 55 wherein:
$R^1$ is hydrogen;
$R^2$ is hydrogen; and
$R^3$ is methyl.

57. The compound of claim 55 wherein:
$R^1$ is hydrogen;
$R^2$ is fluorine; and
$R^3$ is methyl.
58. The compound of claim 47 wherein:
$R^1$ is halo;
$R^2$ is selected from the group consisting of hydrogen, halo and $C_1$–$C_3$ alkyl; and
$R^3$ is $C_1$–$C_3$ alkyl.
59. The compound of claim 58 wherein:
$R^1$ is halo;
$R^2$ is halo; and
$R^3$ is $C_1$–$C_3$ alkyl.
60. The compound of claim 59 wherein:
$R^1$ is fluorine;
$R^2$ is fluorine; and
$R^3$ is methyl.
61. The compound of claim 58 wherein:
$R^1$ is fluorine;
$R^2$ is selected from the group consisting of hydrogen and $C_1$–$C_3$ alkyl; and
$R^3$ is methyl.
62. The compound of claim 61 wherein:
$R^1$ is fluorine;
$R^2$ is hydrogen; and
$R^3$ is methyl.
63. The compound of claim 48 wherein:
$R^1$ is methyl;
$R^2$ is hydrogen; and
$R^3$ is methyl.
64. The compound of claim 48 wherein:
$R^1$ is hydrogen;
$R^2$ is methyl; and
$R^3$ is methyl.
65. The compound of claim 48 wherein:
$R^1$ is methyl;
$R^2$ is methyl; and
$R^3$ is methyl.
66. The compound of claim 46 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted by alkoxy or one or more halo.
67. The compound of claim 66 wherein:
$R^1$ is selected from the group consisting of hydrogen and fluorine;
$R^2$ is $C_1$–$C_3$ alkyl substituted by one or more halo; and
$R^3$ is methyl.
68. The compound of claim 67 wherein:
$R^1$ is hydrogen;
$R^2$ is $CH_2F$; and
$R^3$ is methyl.
69. The compound of claim 66 wherein:
$R^1$ is $CH_2F$;
$R^2$ is hydrogen; and
$R^3$ is methyl.
70. The compound of claim 66 wherein:
$R^1$ is hydrogen,
$R^2$ is hydrogen; and
$R^3$ is $CH_2F$.
71. The compound of claim 66 wherein:
$R^1$ is hydrogen;
$R^2$ is methoxymethyl; and
$R^3$ is methyl.
72. The compound of claim 66 wherein:
$R^1$ is methoxymethyl;
$R^2$ is hydrogen; and
$R^3$ is methyl.
73. The compound of claim 66 wherein:
$R^1$ is hydrogen;
$R^2$ is hydrogen; and
$R^3$ is methoxymethyl.
74. The compound of claim 24 wherein:
$R^1$ is hydrogen;
$R^2$ is fluorine; and
$R^3$ is methyl.
75. The compound of claim 16 wherein:
$R^1$ is halo;
$R^2$ is selected from the group consisting of hydrogen, halo and $C_1$–$C_3$ alkyl; and
$R^3$ is $C_1$–$C_3$ alkyl.
76. The compound of claim 75 wherein:
$R^1$ is halo;
$R^2$ is halo; and
$R^3$ is $C_1$–$C_3$ alkyl.
77. The compound of claim 76 wherein:
$R^1$ is fluorine;
$R^2$ is fluorine; and
$R^3$ is methyl.
78. The compound of claim 76 wherein:
$R^1$ is fluorine;
$R^2$ is selected from the group consisting of hydrogen and $C_1$–$C_3$ alkyl; and
$R^3$ is methyl.
79. The compound of claim 78 wherein:
$R^1$ is fluorine;
$R^2$ is hydrogen; and
$R^3$ is methyl.
80. The compound of claim 16 wherein:
$R^1$ is methyl;
$R^2$ is hydrogen; and
$R^3$ is methyl.
81. The compound of claim 16 wherein:
$R^1$ is hydrogen;
$R^2$ is methyl; and
$R^3$ is methyl.
82. The compound of claim 16 wherein:
$R^1$ is methyl;
$R^2$ is methyl; and
$R^3$ is methyl.
83. The compound of claim 26 wherein:
$R^1$ is selected from the group consisting of hydrogen and fluorine;
$R^2$ is $C_1$–$C_5$ alkyl substituted by one or more halo; and
$R^3$ is methyl.

84. The compound of claim 83 wherein:
$R^1$ is hydrogen;
$R^2$ is $CH_2F$; and
$R^3$ is methyl.
85. The compound of claim 26 wherein:
$R^1$ is $CH_2F$;
$R^2$ is hydrogen; and
$R^3$ is methyl.
86. The compound of claim 26 wherein:
$R^1$ is hydrogen;
$R^2$ is hydrogen; and
$R^3$ is $CH_2F$.
87. The compound of claim 26 wherein:
$R^1$ is hydrogen;
$R^2$ is methoxymethyl; and
$R^3$ is methyl.
88. The compound of claim 26 wherein:
$R^1$ is methoxymethyl;
$R^2$ is hydrogen; and
$R^3$ is methyl.
89. The compound of claim 26 wherein:
$R^1$ is hydrogen;
$R^2$ is hydrogen; and
$R^3$ is methoxymethyl.
90. The compound of claim 14 wherein the compound is the E isomer.
91. The compound of claim 90 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by one or more halo or alkoxy.
92. The compound of claim 91 wherein:
$R^1$ is selected from the group consisting of hydrogen, halo, and $C_1$–$C_3$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.
93. The compound of claim 91 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.
94. The compound of claim 91 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by one or more fluorine or alkoxy.
95. The compound of claim 91 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.
96. The compound of claim 91 wherein:
$R^1$ is hydrogen;
$R^2$ is selected from the group consisting of hydrogen, halo and $C_1$–$C_3$ alkyl; and
$R^3$ is $C_1$–$C_3$ alkyl.
97. The compound of claim 96 wherein:
$R^1$ is hydrogen;
$R^1$ is selected from the group consisting of hydrogen and halo; and
$R^3$ is $C_1$–$C_3$ alkyl.
98. The compound of claim 97 wherein:
$R^1$ is hydrogen;
$R^2$ is selected from the group consisting of hydrogen and fluorine; and
$R^3$ is $C_1$–$C_3$ alkyl.
99. The compound of claim 98 wherein:
$R^1$ is hydrogen;
$R^2$ is selected from the group consisting of hydrogen and fluorine; and
$R^3$ is methyl.
100. The compound of claim 99 wherein:
$R^1$ is hydrogen;
$R^2$ is hydrogen; and
$R^3$ is methyl.
101. The compound of claim 100 wherein:
$R^1$ is hydrogen;
$R^2$ is fluorine; and
$R^3$ is methyl.
102. The compound of claim 91 wherein:
$R^1$ is halo;
$R^2$ is selected from the group consisting of hydrogen, halo and $C_1$–$C_3$ alkyl; and
$R^3$ is $C_1$–$C_3$ alkyl.
103. The compound of claim 102 wherein:
$R^1$ is halo;
$R^2$ is halo; and
$R^3$ is $C_1$–$C_3$ alkyl.
104. The compound of claim 103 wherein:
$R^1$ is fluorine;
$R^2$ is fluorine; and
$R^3$ is methyl.
105. The compound of claim 102 wherein:
$R^1$ is fluorine;
$R^2$ is selected from the group consisting of hydrogen and $C_1$–$C_3$ alkyl; and
$R^3$ is methyl.
106. The compound of claim 105 wherein:
$R^1$ is fluorine;
$R^2$ is hydrogen; and
$R^3$ is methyl.
107. The compound of claim 91 wherein:
$R^1$ is methyl;
$R^2$ is hydrogen; and
$R^3$ is methyl.

108. The compound of claim 91 wherein:
$R^1$ is hydrogen;
$R^2$ is methyl; and
$R^3$ is methyl.
109. The compound of claim 91 wherein:
$R^1$ is methyl;
$R^2$ is methyl; and
$R^3$ is methyl.
110. The compound of claim 90 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted by one or more alkoxy or halo.
111. The compound of claim 110 wherein:
$R^1$ is selected from the group consisting of hydrogen and fluorine;
$R^2$ is $C_1$–$C_3$ alkyl substituted by one or more halo; and
$R^3$ is methyl.
112. The compound of claim 111 wherein:
$R^1$ is hydrogen;
$R^2$ is $CH_2F$; and
$R^3$ is methyl.
113. The compound of claim 110 wherein:
$R^1$ is $CH_2F$;
$R^2$ is hydrogen; and
$R^3$ is methyl.
114. The compound of claim 110 wherein:
$R^1$ is hydrogen;
$R^2$ is hydrogen; and
$R^3$ is $CH_2F$.
115. The compound of claim 110 wherein:
$R^1$ is hydrogen;
$R^2$ is methoxymethyl; and
$R^3$ is methyl.
116. The compound of claim 110 wherein:
$R^1$ is methoxymethyl,
$R^2$ is hydrogen; and
$R^3$ is methyl.
117. The compound of claim 110 wherein:
$R^1$ is hydrogen;
$R^2$ is hydrogen; and
$R^3$ is methoxymethyl.
118. A compound of Formula V

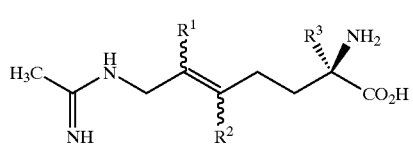

V or a pharmaceutically acceptable salt thereof, wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy, said alkoxy optionally substituted by one or more halo.
119. The compound of claim 118 wherein the compound is the Z isomer.
120. The compound of claim 119 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy.
121. The compound of claim 120 wherein:
$R^1$ is selected from the group consisting of hydrogen, halo, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.
122. The compound of claim 120 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.
123. The compound of claim 119 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by fluorine or alkoxy.
124. The compound of claim 120 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.
125. The compound of claim 120 wherein:
$R^1$ is hydrogen;
$R^2$ is selected from the group consisting of hydrogen, halo and $C_1$–$C_3$ alkyl; and
$R^3$ is $C_1$–$C_3$ alkyl.
126. The compound of claim 125 wherein:
$R^1$ is hydrogen;
$R^2$ is selected from the group consisting of hydrogen and halo; and
$R^3$ is $C_1$–$C_3$ alkyl.
127. The compound of claim 126 wherein:
$R^1$ is hydrogen;
$R^2$ is selected from the group consisting of hydrogen and fluorine; and
$R^3$ is $C_1$–$C_3$ alkyl.

128. The compound of claim 127 wherein:
$R^1$ is hydrogen;
$R^2$ is selected from the group consisting of hydrogen and fluorine; and
$R^3$ is methyl.

129. The compound of claim 128 wherein:
$R^1$ is hydrogen;
$R^2$ is hydrogen; and
$R^3$ is methyl.

130. The compound of claim 128 wherein:
$R^1$ is hydrogen;
$R^2$ is fluorine; and
$R^3$ is methyl.

131. The compound of claim 120 wherein:
$R^1$ is halo;
$R^2$ is selected from the group consisting of hydrogen, halo and $C_1$–$C_3$ alkyl; and
$R^3$ is $C_1$–$C_3$ alkyl.

132. The compound of claim 131 wherein:
$R^1$ is halo;
$R^2$ is halo; and
$R^3$ is $C_1$–$C_3$ alkyl.

133. The compound of claim 132 wherein:
$R^1$ is fluorine;
$R^2$ is fluorine; and
$R^3$ is methyl.

134. The compound of claim 131 wherein:
$R^1$ is fluorine;
$R^2$ is selected from the group consisting of hydrogen and $C_1$–$C_3$ alkyl; and
$R^3$ is methyl.

135. The compound of claim 134 wherein:
$R^1$ is fluorine;
$R^2$ is hydrogen; and
$R^3$ is methyl.

136. The compound of claim 120 wherein:
$R^1$ is methyl;
$R^2$ is hydrogen; and
$R^3$ is methyl.

137. The compound of claim 120 wherein:
$R^1$ is hydrogen;
$R^2$ is methyl; and
$R^3$ is methyl.

138. The compound of claim 120 wherein:
$R^1$ is methyl;
$R^2$ is methyl; and
$R^3$ is methyl.

139. The compound of claim 119 wherein:
$R^1$ is selected from the group consisting of hydrogen, halo and $C_1$–$C_3$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is $C_1$–$C_5$ alkyl optionally substituted by alkoxy or one or more halo.

140. The compound of claim 139 wherein:
$R^1$ is selected from the group consisting of hydrogen and fluorine;
$R^2$ is $C_1$–$C_3$ alkyl substituted by one or more halo; and
$R^3$ is methyl.

141. The compound of claim 140 wherein:
$R^1$ is hydrogen;
$R^2$ is $CH_2F$; and
$R^3$ is methyl.

142. The compound of claim 139 wherein:
$R^1$ is $CH_2F$;
$R^2$ is hydrogen; and
$R^3$ is methyl.

143. The compound of claim 139 wherein:
$R^1$ is hydrogen;
$R^2$ is hydrogen; and
$R^3$ is $CH_2F$.

144. The compound of claim 139 wherein:
$R^1$ is hydrogen;
$R^2$ is methoxymethyl; and
$R^3$ is methyl.

145. The compound of claim 139 wherein:
$R^1$ is methoxymethyl;
$R^2$ is hydrogen; and
$R^3$ is methyl.

146. The compound of claim 139 wherein:
$R^1$ is hydrogen;
$R^2$ is hydrogen; and
$R^3$ is methoxymethyl.

147. The compound of claim 118 wherein the compound is the E isomer.

148. The compound of claim 147 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by one or more halo or alkoxy.

149. The compound of claim 148 wherein:
$R^1$ is selected from the group consisting of hydrogen, halo, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.

150. The compound of claim 148 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.

151. The compound of claim 148 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and $R^3$ is $C_1$–$C_5$ alkyl, said $C_1$–$C_5$ alkyl optionally substituted by fluorine or alkoxy.

152. The compound of claim 148 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.

153. The compound of claim 148 wherein:
$R^1$ is hydrogen;
$R^2$ is selected from the group consisting of hydrogen, halo and $C_1$–$C_3$ alkyl; and
$R^3$ is $C_1$–$C_3$ alkyl.

154. The compound of claim 153 wherein:
$R^1$ is hydrogen;
$R^2$ is selected from the group consisting of hydrogen and halo; and
$R^3$ is $C_1$–$C_3$ alkyl.

155. The compound of claim 154 wherein:
$R^1$ is hydrogen;
$R^2$ selected from the group consisting of hydrogen and fluorine; and
$R^3$ is $C_1$–$C_3$ alkyl.

156. The compound of claim 155 wherein:
$R^1$ is hydrogen;
$R^2$ is selected from the group consisting of hydrogen and fluorine; and
$R^3$ is methyl.

157. The compound of claim 155 wherein:
$R^1$ is hydrogen;
$R^2$ is hydrogen; and
$R^3$ is methyl.

158. The compound of claim 156 wherein:
$R^1$ is hydrogen;
$R^2$ is fluorine; and
$R^3$ is methyl.

159. The compound of claim 148 wherein:
$R^1$ is halo;
$R^2$ is selected from the group consisting of hydrogen, halo and $C_1$–$C_3$ alkyl; and
$R^3$ is $C_1$–$C_3$ alkyl.

160. The compound of claim 159 wherein:
$R^1$ is halo;
$R^2$ is halo; and
$R^3$ is $C_1$–$C_3$ alkyl.

161. The compound of claim 160 wherein:
$R^1$ is fluorine;
$R^2$ is fluorine; and
$R^3$ is methyl.

162. The compound of claim 159 wherein:
$R^1$ is fluorine;
$R^2$ is selected from the group consisting of hydrogen and $C_1$–$C_3$ alkyl; and
$R^3$ is methyl.

163. The compound of claim 162 wherein:
$R^1$ is fluorine;
$R^2$ is hydrogen; and
$R^3$ is methyl.

164. The compound of claim 148 wherein:
$R^1$ is methyl;
$R^2$ is hydrogen; and
$R^3$ is methyl.

165. The compound of claim 148 wherein:
$R^1$ is hydrogen;
$R^2$ is methyl; and
$R^3$ is methyl.

166. The compound of claim 148 wherein:
$R^1$ is methyl;
$R^2$ is methyl; and
$R^3$ is methyl.

167. The compound of claim 147 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted by one or more alkoxy or halo.

168. The compound of claim 167 wherein:
$R^1$ is selected from the group consisting of hydrogen and fluorine;
$R^2$ is $C_1$–$C_3$ alkyl substituted by one or more halo; and
$R^3$ is methyl.

169. The compound of claim 168 wherein:
$R^1$ is hydrogen;
$R^2$ is $CH_2F$, and
$R^3$ is methyl.

170. The compound of claim 168 wherein:
$R^1$ is $CH_2F$;
$R^2$ is hydrogen; and
$R^3$ is methyl.

171. The compound of claim 167 wherein:
$R^1$ is hydrogen;
$R^2$ is hydrogen; and
$R^3$ is $CH_2F$.

172. The compound of claim 167 wherein;
$R^1$ is hydrogen;
$R^2$ is methoxymethyl; and
$R^3$ is methyl.

173. The compound of claim 167 wherein:
$R^1$ is methoxymethyl;
$R^2$ is hydrogen; and
$R^3$ is methyl.

174. The compound of claim 167 wherein:
$R^1$ is hydrogen;
$R^2$ is hydrogen; and
$R^3$ is methoxymethyl.

175. A pharmaceutical composition comprising at least one compound selected from the group consisting of:
(2S,5E)-2-amino-2-methyl-6-fluoro-7-[(1-iminoethyl) amino]-5-heptenoic acid;
(2R,5E)-2-amino-2-methyl-6-fluoro-7-[(1-iminoethyl) amino]-5-heptenoic acid;
(2R/S,5E)-2-amino-2-methyl-6-fluoro-7-[(1-iminoethyl) amino]-5-heptenoic acid
(2R/S,5E)-2-amino-2-methyl-5-fluoro-7-[(1-iminoethyl) amino]-5-heptenoic acid;

(2R/S,5Z)-2-amino-2-methyl-5-fluoro-7-[(1-iminoethyl)amino]-5-heptenoic acid;

(2R,5E)-2-amino-2-methyl-5-fluoro-7-[(1-iminoethyl)amino]-5-heptenoic acid;

(2S,5E)-2-amino-2-methyl-5-fluoro-7-[(1-iminoethyl)amino]-5-heptenoic acid;

(2S,5Z)-2-amino-2-methyl-5,6-difluoro-7-[(1-iminoethyl)amino]-5-heptenoic acid;

(2R,5Z)-2-amino-2-methyl-5,6-difluoro-7-[(1-iminoethyl)amino]-5-heptenoic acid;

(2R/S,5Z)-2-amino-2-methyl-5,6-difluoro-7-[(1-iminoethyl)amino]-5-heptenoic acid;

(2S,5Z)-2-amino-2-methyl-6-fluoro-7-[(1-iminoethyl)amino]-5-heptenoic acid;

(2S,5Z)-2-amino-2-methyl-7-[(1-iminoethyl)amino]-5-heptenoic acid;

(2S,5Z)-2-amino-2-methyl-7-[(1-iminoethyl)amino]-5-heptenoic acid;

(2R,5Z)-2-amino-2-methyl-7-[(1-iminoethyl)amino]-5-heptenoic acid;

(2R/S,5E)-2-amino-2-methyl-7-[(1-iminoethyl)amino]-5-heptenoic acid;

(2S-5E)-2-amino-2-ethyl-6-fluoro-7-[(1-iminoethyl)amino]-5-heptenoic acid;

(2S-5E)-2-amino-2-methoxymethyl-6-fluoro-7-[(1-iminoethyl)amino]-5-heptenoic acid;

(2S,5E)-2-amino-2-fluoromethyl-6-fluoro-7-[(1-iminoethyl)amino]-5-heptenoic acid;

(2S,5E)-2-amino-2,5-dimethyl-6-fluoro-7-[(1-iminoethyl)amino]-5-heptenoic acid;

(2S,5Z)-2-amino-5-fluoromethyl-2-methyl-6-fluoro-7-[(1-iminoethyl)amino]-5-heptenoic acid;

(2S,5E)-2-amino-2,6-dimethyl-5-fluoro-7-[(1-iminoethyl)amino]-5-heptenoic acid;

(2S,5Z)-2-amino-6-fluoromethyl-2-methyl-5-fluoro-7-[(1-iminoethyl)amino]-5-heptenoic acid;

(2S,5Z)-2-amino-2-ethyl-7-[(1-iminoethyl)amino]-5-heptenoic acid;

(2S,5Z)-2-amino-2-methoxymethyl-7-[(1-iminoethyl)amino]-5-heptenoic acid;

(2S,5Z)-2-amino-2-fluoromethyl-7-[(1-iminoethyl)amino]-5-heptenoic acid;

(2S,5Z)-2-amino-2,5-dimethyl-7-[(1-iminoethyl)amino]-5-heptenoic acid;

(2S,5E)-2-amino-5-fluoromethyl-2-methyl-7-[(1-iminoethyl)amino]-5-heptenoic acid;

(2S,5Z)-2-amino-2,6-dimethyl-7-[(1-iminoethyl)amino]-5-heptenoic acid;

(2S,5E)-2-amino-6-fluoromethyl-2-methyl-7-[(1-iminoethyl)amino]-5-heptenoic acid;

(2S,5E)-2-amino-2-methyl-6-fluoro-7-[(1-iminoethyl)amino]-5-heptenoic acid, dihydrochloride;

(2R,5E)-2-amino-2-methyl-6-fluoro-7-[(1-iminoethyl)amino]-5-heptenoic acid, dihydrochloride;

(2R/S,5E)-2-amino-2-methyl-6-fluoro-7-[(1-iminoethyl)amino]-5-heptenoic acid, dihydrochloride;

(2R/S,5E)-2-amino-2-methyl-5-fluoro-7-[(1-iminoethyl)amino]-5-heptenoic acid, dihydrochloride;

(2R/S,5Z)-2-amino-2-methyl-5-fluoro-7-[(1-iminoethyl)amino]-5-heptenoic acid, dihydrochloride;

(2R,5E)-2-amino-2-methyl-5-fluoro-7-[(1-iminoethyl)amino]-5-heptenoic acid, dihydrochloride;

(2S,5E)-2-amino-2-methyl-5-fluoro-7-[(1-iminoethyl)amino]-5-heptenoic acid, dihydrochloride;

(2S,5Z)-2-amino-2-methyl-5,6-difluoro-7-[(1-iminoethyl)amino]-5-heptenoic acid, dihydrochloride;

(2R,5Z)-2-amino-2-methyl-5,6-difluoro-7-[(1-iminoethyl)amino]-5-heptenoic acid, dihydrochloride;

(2R/S,5Z)-2-amino-2-methyl-5,6-difluoro-7-[(1-iminoethyl)amino]-5-heptenoic acid, dihydrochloride;

(2S,5Z)-2-amino-2-methyl-6-fluoro-7-[(1-iminoethyl)amino]-5-heptenoic acid, dihydrochloride;

(2S,5Z)-2-amino-2-methyl-7-[(1-iminoethyl)amino]-5-heptenoic acid, dihydrochloride;

(2S,5Z)-2-amino-2-methyl-7-[(1-iminoethyl)amino]-5-heptenoic acid, dihydrochloride;

(2R,5Z)-2-amino-2-methyl-7-[(1-iminoethyl)amino]-5-heptenoic acid, dihydrochloride;

(2R/S,5E)-2-amino-2-methyl-7-[(1-iminoethyl)amino]-5-heptenoic acid, dihydrochloride;

(2S,5E)-2-amino-2-ethyl-6-fluoro-7-[(1-iminoethyl)amino]-5-heptenoic acid, dihydrochloride;

(2S,5E)-2-amino-2-methoxymethyl-6-fluoro-7-[(1-iminoethyl)amino]-5-heptenoic acid, dihydrochloride;

(2S,5E)-2-amino-2-fluoromethyl-6-fluoro-7-[(1-iminoethyl)amino]-5-heptenoic acid, dihydrochloride;

(2S,5E)-2-amino-2,5-dimethyl-6-fluoro-7-[(1-iminoethyl)amino]-5-heptenoic acid, dihydrochloride;

(2S,5Z)-2-amino-5-fluoromethyl-2-methyl-6-fluoro-7-[(1-iminoethyl)amino]-5-heptenoic acid, dihydrochloride;

(2S,5E)-2-amino-2,6-dimethyl-5-fluoro-7-[(1-iminoethyl)amino]-5-heptenoic acid, dihydrochloride;

(2S,5Z)-2-amino-6-fluoromethyl-2-methyl-5-fluoro-7-[(1-iminoethyl)amino]-5-heptenoic acid, dihydrochloride;

(2S,5Z)-2-amino-2-ethyl-7-[(1-iminoethyl)amino]-5-heptenoic acid, dihydrochloride;

(2S,5Z)-2-amino-2-methoxymethyl-7-[(1-iminoethyl)amino]-5-heptenoic acid, dihydrochloride;

(2S,5Z)-2-amino-2-fluoromethyl-7-[(1-iminoethyl)amino]-5-heptenoic acid, dihydrochloride;

(2S,5Z)-2-amino-2,5-dimethyl-7-[(1-iminoethyl)amino]-5-heptenoic acid, dihydrochloride;

(2S,5E)-2-amino-5-fluoromethyl-2-methyl-7-[(1-iminoethyl)amino]-5-heptenoic acid, dihydrochloride;

(2S,5Z)-2-amino-2,6-dimethyl-7-[(1-iminoethyl)amino]-5-heptenoic acid, dihydrochloride;

(2S,5E)-2-amino-6-fluoromethyl-2-methyl-7-[(1-iminoethyl)amino]-5-heptenoic acid, dihydrochloride; and 176. A compound of Formula VII:

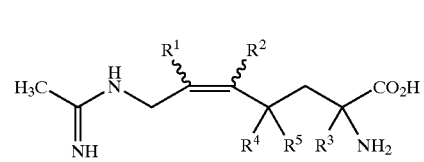

or a pharmaceutically acceptable salt thereof, wherein:
$R^1$ is selected from die group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and $R^5$ is selected from the group consisting of halo and $C_1$–$C_5$ alkyl, said $C_1$–$C_5$ alkyl optionally substituted by halo or alkoxy, said alkoxy optionally substituted by one or more halo.

177. The compound of claim 176 wherein;

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is selected from the group consisting of halo and $C_1$–$C_5$ alkyl, said $C_1$–$C_5$ alkyl optionally substituted by halo or alkoxy.

178. The compound of claim 176 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen and halo; and $R^5$ is selected from the group consisting of halo and $C_1$–$C_5$ alkyl, said $C_1$–$C_5$ alkyl optionally substituted by halo or alkoxy.

179. The compound of claim 177 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $C_1$–$C_5$ alkyl, said $C_1$–$C_5$ alkyl optionally substituted by halo or alkoxy, said alkoxy optionally substituted by one or more halo.

180. The compound of claim 179 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^1$ is $C_1$–$C_5$ alkyl, said $C_1$–$C_5$ alkyl optionally substituted by one or more halo.

181. The compound of claim 178 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is $C_1$–$C_5$ alkyl, said $C_1$–$C_5$ alkyl optionally substituted by halo or alkoxy, said alkoxy optionally substituted by one or more halo; and $R^5$ is halo.

182. The compound of claim 181 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is $C_1$–$C_5$ alkyl, said $C_1$–$C_5$ alkyl optionally substituted by halo or alkoxy, said alkoxy optionally substituted by one or more halo; and $R^5$ is fluorine.

183. The compound of claim 180 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by alkoxy, said alkoxy optionally substituted by one or more halo;

R⁴ is selected from the group consisting of hydrogen, halo and $C_1$–$C_5$ alkyl, said $C_1$–$C_5$ alkyl optionally substituted by halo or alkoxy; and R⁵ is $C_1$–$C_5$ alkyl substituted by halo.

184. The compound of claim 183 wherein:

R¹ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R² is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R³ is $C_1$–$C_5$ alkyl, said $C_1$–$C_5$ alkyl optionally substituted by alkoxy, said alkoxy optionally substituted by one or more halo;

R⁴ is selected from the group consisting of hydrogen, halo and $C_1$–$C_5$ alkyl, said $C_1$–$C_5$ alkyl optionally substituted by halo or alkoxy; and R⁵ is $CH_2F$.

185. The compound of claim 184 wherein:

R¹ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R² is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R³ is $C_1$–$C_5$ alkyl, said $C_1$–$C_5$ alkyl optionally substituted by halo or alkoxy, said alkoxy optionally substituted by one or more halo;

R⁴ is hydrogen; and

R⁵ is $CH_2F$.

186. The compound of claim 178 wherein:

R¹ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R² is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R³ is $C_1$–$C_5$ alkyl, said $C_1$–$C_5$ alkyl optionally substituted by halo or alkoxy, said alkoxy optionally substituted by one or more halo;

R⁴ is halo; and

R⁵ is halo.

187. The compound of claim 178 wherein:

R¹ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R² is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R³ is $C_1$–$C_5$ alkyl, said $C_1$–$C_5$ alkyl optionally substituted by halo or alkoxy, said alkoxy optionally substituted by one or more halo;

R⁴ is hydrogen; and

R⁵ is halo.

188. The compound of claim 187 wherein

R¹ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R² is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R³ is $C_1$–$C_5$ alkyl, said $C_1$–$C_5$ alkyl optionally substituted by halo or alkoxy, said alkoxy optionally substituted by one or more halo;

R⁴ is fluorine; and

R⁵ is fluorine.

189. The compound of claim 180 wherein:

R¹ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R² is selected from the group consisting of hydrogen, halo, and $C_1$–$C_5$ alkyl, Bald $C_1$–$C_5$ alkyl optionally substituted by halo or alkoxy, said alkoxy optionally substituted by one or more halo;

R³ is $C_1$–$C_5$ alkyl, said $C_1$–$C_5$ alkyl optionally substituted by halo or alkoxy, said alkoxy optionally substituted by one or more halo;

R⁴ is hydrogen; and

R⁵ is methyl.

190. A compound of Formula VIII:

or a pharmaceutically acceptable salt thereof, wherein:

R¹ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R² is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R³ is $C_1$–$C_5$ alkyl, said $C_1$–$C_5$ alkyl optionally substituted by halo or alkoxy, said alkoxy optionally substituted by one or more halo;

R⁴ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and R⁵ selected from the group consisting of halo and $C_1$–$C_5$ alkyl, said $C_1$–$C_5$ alkyl optionally substituted by halo or alkoxy, said alkoxy optionally substituted by one or more halo.

191. The compound of claim 190 wherein:

R¹ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

R² is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ selected from the group consisting of halo and $C_1$–$C_5$ alkyl, said $C_1$–$C_5$ alkyl optionally substituted by halo or alkoxy.

192. The compound of claim 190 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen and halo; and $R^5$ is selected from the group consisting of halo and $C_1$–$C_5$ alkyl, said $C_1$–$C_5$ alkyl optionally substituted by halo or alkoxy.

193. The compound of claim 191 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $C_1$–$C_5$ alkyl, said $C_1$–$C_5$ alkyl optionally substituted by halo or alkoxy, said alkoxy optionally substituted by one or more halo.

194. The compound of claim 193 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $C_1$–$C_5$ alkyl, said $C_1$–$C_5$ alkyl optionally substituted by one or more halo.

195. The compound of claim 192 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is $C_1$–$C_5$ alkyl, said $C_1$–$C_5$ alkyl optionally substituted by halo or alkoxy, said alkoxy optionally substituted by one or more halo; and $R^5$ is halo.

196. The compound of claim 195 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is $C_1$–$C_5$ alkyl, said $C_1$–$C_5$ alkyl optionally substituted by halo or alkoxy, said alkoxy optionally substituted by one or more halo; and $R^5$ is fluorine.

197. The compound of claim 194 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_3$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $C_1$–$C_5$ alkyl substituted by halo.

198. The compound of claim 197 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by alkoxy, said alkoxy optionally substituted by one or more halo;

$R^4$ is selected from the group consisting of hydrogen, halo and $C_1$–$C_5$ alkyl, said $C_1$–$C_5$ alkyl optionally substituted by halo or alkoxy; and $R^5$ is $CH_2F$.

199. The compound of claim 198 wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^3$ is C$_1$–C$_5$ alkyl, said C$_1$–C$_5$ alkyl optionally substituted by halo or alkoxy, said alkoxy optionally substituted by one or more halo;
R$^4$ is hydrogen; and
R$^5$ is CH$_2$F.
200. The compound of claim 192 wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^3$ is C$_1$–C$_5$ alkyl, said C$_1$–C$_5$ alkyl optionally substituted by halo or alkoxy, said alkoxy optionally substituted by one or more halo;
R$^1$ is halo; and
R$^5$ is halo.
201. The compound of claim 191 wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^3$ is C$_1$–C$_5$ alkyl, said C$_1$–C$_5$ alkyl optionally substituted by halo or alkoxy, said alkoxy optionally substituted by one or more halo;
R$^4$ is hydrogen; and
R$^5$ is halo.
202. The compound of claim 201 wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^3$ is C$_1$–C$_5$ alkyl, said C$_1$–C$_5$ alkyl optionally substituted by halo or alkoxy, said alkoxy optionally substituted by one or more halo;
R$^4$ is fluorine; and
R$^5$ is fluorine.
203. The compound of claim 194 wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^3$ is C$_1$–C$_5$ alkyl, said C$_1$–C$_5$ alkyl optionally substituted by halo or alkoxy, said alkoxy optionally substituted by one or more halo;
R$^4$ is hydrogen; and
R$^5$ is methyl.
204. A compound of Formula IX:

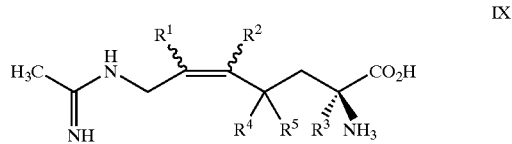

or a pharmaceutically acceptable salt thereof, wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^3$ is C$_1$–C$_5$ alkyl, said C$_1$–C$_5$ alkyl optionally substituted by halo or alkoxy, said alkoxy optionally substituted by one or more halo;
R$^4$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo; and
R$^5$ is selected from the group consisting of halo and C$_1$–C$_5$ alkyl, said C$_1$–C$_5$ alkyl optionally substituted by halo or alkoxy, said alkoxy optionally substituted by one or more halo.
205. The compound of claim 204 wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^3$ is C$_1$–C$_5$ alkyl, said C$_1$–C$_5$ alkyl optionally substituted by halo or alkoxy, said alkoxy optionally substituted by one or more halo;
R$^4$ is selected from the group consisting of hydrogen, halo and C$_1$–C$_5$ alkyl, said C$_1$–C$_5$ alkyl optionally substituted by halo or alkoxy; and
R$^5$ is selected from the group consisting of halo and C$_1$–C$_5$ alkyl, said C$_1$–C$_5$ alkyl optionally substituted by halo or alkoxy.
206. The compound of claim 204 wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^3$ is C$_1$–C$_5$ alkyl, said C$_1$–C$_5$ alkyl optionally substituted by halo or alkoxy, said alkoxy optionally substituted by one or more halo;

R$^4$ is selected from the group consisting of hydrogen and halo; and

R$^5$ is selected from the group consisting of halo and C$_1$–C$_5$ alkyl, said C$_1$–C$_5$ alkyl optionally substituted by halo or alkoxy.

207. The compound of claim 205 wherein:

R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or mare halo;

R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^3$ is C$_1$–C$_5$ alkyl, said C$_1$–C$_5$ alkyl optionally substituted by halo or alkoxy, said alkoxy optionally substituted by one or more halo;

R$^4$ is selected from the group consisting of hydrogen, halo and C$_1$–C$_5$ alkyl, said C$_1$–C$_5$ alkyl optionally substituted by halo or alkoxy; and R$^5$ is C$_1$–C$_5$ alkyl, said C$_1$–C$_5$ alkyl optionally substituted by halo or alkoxy, said alkoxy optionally substituted by one or more halo.

208. The compound of claim 207 wherein:

R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^3$ is C$_1$–C$_5$ alkyl, said C$_1$–C$_5$ alkyl optionally substituted by halo or alkoxy, said alkoxy optionally substituted by one or more halo;

R$^4$ is selected from the group consisting of hydrogen, halo and C$_1$–C$_5$ alkyl, said C$_1$–C$_5$ alkyl optionally substituted by halo or alkoxy; and R$^5$ is C$_1$–C$_5$ alkyl, said C$_1$–C$_5$ alkyl optionally substituted by one or more halo.

209. The compound of claim 204 wherein:

R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^3$ is C$_1$–C$_5$ alkyl, said C$_1$–C$_5$ alkyl optionally substituted by halo or alkoxy, said alkoxy optionally substituted by one or more halo;

R$^4$ is C$_1$–C$_5$ alkyl, said C$_1$–C$_5$ alkyl optionally substituted by halo or alkoxy, said alkoxy optionally substituted by one or more halo; and R$^5$ is halo.

210. The compound of claim 209 wherein:

R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^3$ is C$_1$–C$_5$ alkyl, said C$_1$–C$_5$ alkyl optionally substituted by halo or alkoxy, said alkoxy optionally substituted by one or more halo;

R$^4$ is C$_1$–C$_5$ alkyl, said C$_1$–C$_5$ alkyl optionally substituted by halo or alkoxy, said alkoxy optionally substituted by one or more halo; and R$^5$ is fluorine.

211. The compound of claim 208 wherein:

R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^3$ is C$_1$–C$_5$ alkyl, said C$_1$–C$_5$ alkyl optionally substituted by alkoxy, said alkoxy optionally substituted by one or more halo;

R$^4$ is selected from the group consisting of hydrogen, halo and C$_1$–C$_5$ alkyl, said C$_1$–C$_5$ alkyl optionally substituted by halo or alkoxy; and R$^5$ is C$_1$–C$_5$ alkyl substituted by halo.

212. The compound of claim 211 wherein:

R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^3$ is C$_1$–C$_5$ alkyl, said C$_1$–C$_5$ alkyl optionally substituted by alkoxy, said alkoxy optionally substituted by one or more halo;

R$^4$ is selected from the group consisting of hydrogen, halo and C$_1$–C$_5$ alkyl, said C$_1$–C$_5$ alkyl optionally substituted by halo or alkoxy; and R$^5$ is CH$_2$F.

213. The compound of claim 212 wherein:

R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^3$ is C$_1$–C$_5$ alkyl, said C$_1$–C$_5$ alkyl optionally substituted by halo or alkoxy, said alkoxy optionally substituted by one or more halo;

R$^4$ is hydrogen; and

R$^5$ is CH$_2$F.

214. The compound of claim 206 wherein:

R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is halo; and $R^5$ is halo.

215. The compound of claim 204 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is hydrogen; and $R^5$ is halo.

216. The compound of claim 215 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is fluorine; and $R^5$ is fluorine.

217. The compound of claim 208 wherein:

$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;

$R^2$ is selected from the group consisting of hydrogen, halo, and $C_1$–$C_5$ alkyl, said $C_1$–$C_3$ alkyl optionally substituted by halo or alkoxy, said alkoxy optionally substituted by one or more halo;

$R^3$ is $C_1$–$C_5$ alkyl, said $C_1$–$C_5$ alkyl optionally substituted by halo or alkoxy, said alkoxy optionally substituted by one or more halo;

$R^4$ is hydrogen; and $R^5$ is methyl.

* * * * *